US008143308B2

(12) United States Patent
Bruno et al.

(10) Patent No.: US 8,143,308 B2
(45) Date of Patent: Mar. 27, 2012

(54) SYNTHESIS OF OLIGO/POLY(CATECHINS) AND METHODS OF USE

(75) Inventors: Ferdinando F. Bruno, Andover, MA (US); Jayant Kumar, Westford, MA (US); Subhalakshmi Nagarajan, Dracut, MA (US); Susan J. Braunhut, Wellesley, MA (US); Ramaswamy Nagarajan, Dracut, MA (US); Lynne A. Samuelson, Marlborough, MA (US); Donna McIntosh, Chelmsford, MA (US); Klaudia Foley, Littleton, MA (US)

(73) Assignees: University of Massachusetts Lowell, Lowell, MA (US); The United States of America, as represented by the Secretary of the Army, Washington, DC (US)

( * ) Notice: Subject to any disclaimer, the term of this patent is extended or adjusted under 35 U.S.C. 154(b) by 818 days.

(21) Appl. No.: 11/978,540

(22) Filed: Oct. 29, 2007

(65) Prior Publication Data

US 2009/0170928 A1 Jul. 2, 2009

Related U.S. Application Data

(63) Continuation of application No. PCT/US2006/015872, filed on Apr. 27, 2006.

(60) Provisional application No. 60/675,822, filed on Apr. 28, 2005.

(51) Int. Cl.
*A61K 31/352* (2006.01)
*A61P 35/00* (2006.01)
*C07D 407/02* (2006.01)
*C12P 17/16* (2006.01)

(52) U.S. Cl. .......................... 514/456; 435/118; 549/399

(58) Field of Classification Search .................. None
See application file for complete search history.

(56) References Cited

U.S. PATENT DOCUMENTS

| | | | |
|---|---|---|---|
| 3,632,785 A | 1/1972 | Bornstein | |
| 5,136,060 A | 8/1992 | Holton | |
| 5,175,315 A | 12/1992 | Holton | |
| 5,229,526 A | 7/1993 | Holton | |
| 2002/0128493 A1* | 9/2002 | Romanczyk et al. | 549/399 |

FOREIGN PATENT DOCUMENTS

| | | |
|---|---|---|
| WO | WO 93/06079 | 4/1993 |
| WO | WO 01/18125 A1 | 3/2001 |
| WO | WO 2004/024070 A2 | 3/2004 |

OTHER PUBLICATIONS

Mejias et al., Macromol. Biosci., (2002), vol. 2, p. 24-32.*
Mitscher, L.A.; et al., "Chemoprotection: A Review of the Potential Therapeutic Antioxidant Properties of Green Tea (*Camellia sinensis*) and Certain of its Constituents," *Medicinal Research Reviews*, 17(4):327-365 (1997).
Goodin, M.G., et al., "Estrogen Receptor-Mediated Actions of Polyphenolic Catechins in Vivo and in Vitro"; *Toxicological Sciences*, 69:354-361 (2002).
Moyers, S.B., et al., "Green Tea Polyphenols and Cancer Chemoprevention: Multiple Mechanisms and Endpoints for Phase II Trials," *Nutrition Reviews*, 62(5):204-211 (May 2004).
Ahmad, N., et al., "Cutaneous Photochemoprotection by Green Tea: A Brief Review," *Skin Pharmacol Appl Skin Physiol*, 14:69-76 (2001).
Berger, S.J., et al., "Green Tea Constituent (−)-Epigallocatechin-3-gallate Inhibits Topoisomerase I Activity in Human Colon Carcinoma Cells," *Biochemical and Biophysical Research Communications*, 288:101-105 (2001).
Ji, B.T., et al., "Green Tea Consumption and the Risk of Pancreatic and Colorectal Cancers," *Int. J. Cancer*, 70:255-258 (1997).
Fujiki, H., et al., "Cancer Inhibition by Green Tea," *Mutation Research*, 402:307-310 (1998).
López-Lázaro, M., "Flavonoids as anticancer agents: Structure-Activity Relationship Study," *Curr. Med. Chem.—Anti-Cancer Agents*, 2:691-714 (2002).
Demeule, M., et al. "Green Tea Catechins as Novel Antitumor and Antiangiogenic Compounds," *Curr. Med. Chem.—Anti-Cancer Agents*, 2:441-463 (2002).
Suzuki, J., et al., "Catechins Attenuate Myocardial Cell Infiltration and Fibrosis but Do Not Prolong Graft survival in Murine Cardiac Allografts," *Transplanation Proc.*, 37:119-120 (2005).
Liu, S., et al., "Theaflavin Derivatives in Black Tea and Catechin Derivatives in Green Tea Inhibit HIV-1 Entry by Targeting gp41," *Biochimica et Biophysica Acta*, 1723:270-281 (2005).
Wolfram S., et al., "TEAVIGO™ (Epigallocatechin Gallate) Supplementation Prevents Obesity in Rodents by Reducing Adipose Tissue Mass," *Ann Nutr Metab.*, 49:54-63 (2005).
Kurisawa, M., et al., "Amplification of Antioxidant Activity and Xanthine Oxidase Inhibition of Catechin by Enzymatic Polymerization," *Biomacromol.*, 4(3):469-471 (May/Jun. 2003).
Mejias, L., et al., "New Polymers from Natural Phenols Using Horseradish or Soybean Peroxidase," *Macromol. Biosci.*, 2:24-32 (2002).
Kobayashi, S., et al., "Antioxidant having Cytostatic Activity and Useful for Suppressing Formation of Peroxylipids and DNA Polymerase Deactivation Comprising Polyphenol Polymer," Database WPI Week 200382, AN 2003-881864, XP-002401696 & JP 2003 138258, May 2003, Abstract.
Konya, M., et al., "Flavonoid Polymers Useful as Glucosyl-Transferase Inhibitors—Obtd. by treating Flavonoid(s) with Peroxidase," Database WPI Week 199440, AN 1994-322174, XP-002401697 & JP 06247959, Sep. 1994, Abstract.

(Continued)

*Primary Examiner* — Yong Chu
(74) *Attorney, Agent, or Firm* — Hamilton, Brook, Smith & Reynolds, P.C.

(57) ABSTRACT

A method for synthesizing a biocompatible, water-soluble oligo/polyflavanoid, includes polymerizing an optionally substituted flavanoid with a polymerization agent in the presence of a biocompatible polymerization solubilizer, thereby producing the biocompatible, soluble oligo/polyflavanoid. Also included is a biocompatible, soluble, oligo/polyflavanoid or a pharmaceutically acceptable salt, solvate, or complex thereof. Also included are methods of treating a subject for cancer, cardiac damage, viral infection, and obesity.

36 Claims, 13 Drawing Sheets

OTHER PUBLICATIONS

Liu, W., et al., "The Role of Template in the Enzymatic Synthesis of Conducting Polyaniline," *J. Am. Chem. Soc.*, 121:11345-11355 (1999).

Liu, W., et al., "Enzymatically Synthesized Conducting Polyaniline," *J. Am. Chem. Soc.*, 121:71-78 (1999).

Kurisawa, M., et al., "Laccase-Catalyzed Synthesis and Antioxidant Property of Poly(catechin)," *Macromol. Biosci.*, 3:758-764 (2003).

Pianetti, S., et al., "Green Tea Polyphenol Episgallocatechin-3 Gallate Inhibits Her-2/Neu Signaling, Proliferation, and Transformed Phenotype of Breast Cancer Cells," *Cancer Research*, 62:652-655 (2002).

Bruno, F.F., et al., "Novel Enzymatic Polyethylene Oxide-Polyphenol System for Ionic Conductivity," *Journal of Macromolecular Science*, A39(10):1061-1068 (2002).

Nagarajan, R., et al., "Manipulating DNA Conformation Using Intertwined Conducting Polymer Chains," *Macromolecules*, 34:3921-3927 (2001).

Bruno, F.F., et al., "Biomimetic Synthesis of Water Soluble Conductive Polypyrrole and Poly (3,4 ethylenedioxythiophene)," *Journal of Macromolecular Science, Pure and Appl.Chem.*, A40(12):1327-1333 (2003).

Kinjo, J., et al., "Activity-Guided Fractionation of Green Tea Extract with Antiproliferative Activity against Human Stomach Cancer Cells," *Biol. Pharm. Bull.*, 25(9):1238-1240 (2002).

Kozikowski, A.P., et al., "Studies in Polyphenol Chemistry and Bioactivity. 4. Synthesis of Trimeric, Tetrameric, Pentameric, and Higher Oligomeric Epicatechin-Derived Procyanidins Having All-4β,8-Interflavan Connectivity and Their Inhibition of Cancer Cell Growth through Cell Cycle Arrest," *J. Org. Chem.*, 68(5):1641-1658 (2003).

Notification of Transmittal of the International Search Report or the Declaration, International Search Report and Written Opinion of the International Searching Authority in International Application No. PCT/US2006/015872, 16 pages, mailed Mar. 8, 2007.

Notification of Transmittal of International Preliminary Report on Patentability and International Preliminary Report on Patentability in International Application No. PCT/US2006/015872, 9 pages, mailed Oct. 30, 2007.

Braunhut, S.J., et al., "Detection of Apoptosis and drug Resistance of Human Breast Cancer Cells to Taxane Treatments Using Quartz Crystal Microbalance Biosensor Technology" Assay and Drug Development Technologies, 3(1): 77-88 (2005).

Guillory, J. Keith, "Generation of Polymorphs, Hydrates, Solvates, and Amorphous Solids," In *Polymorphism in Pharmaceutical Solids*, H.G. Brittain, eds. (Marcel Dekker, Inc.), pp. 183-226 (1999).

Holton, R.A. et al., "First Total Synthesis of Taxo. 2. Completion of the C and D Rings," *J. Am. Chem. Soc.*, 116(4), 1599-1600 (1994).

Holton, R.A. et al., "First Total Synthesis of Taxol. 1. Functionalization of the B Ring," *J. Am. Chem. Soc.*, 116(4), 1597-1598, (1994).

Kozikowski, A.P., et al., "Studies in Polyphenol Chemistry and Bioactivity.4.[1] Synthesis of Trimeric, Tetrameric, Pentameric, and Higher Oligomeric Epicatechin-Derived Procyanidins Having A11-4β,8-Interflaven Connectivity and Their Inhibition of Cancer Cell Growth Through Cell Cycle Arrest[1]," *J. Org. Chem.*, 68: 1641-1658 (2003).

Nagarajan, S., et al., "Bioctalytically Oligomerized Epicatechin with Potent and Specific Anti-Proliferative Activity for Human Breast Cancer Cells," *Molecules*, 13: 2704-2716 (2008).

Vippagunta, S.R., et al. "Crystalline Solids," *Advanced Drug Delivery Reviews*, 48: 3-26 (2001).

Vorononikova, E., et al., "Retinoids and TIMP1 Prevent Radiation-Induced Apoptosis of Vascular Endothelial Cells" *Rad. Res.* 161,174-184 (2004).

\* cited by examiner

PVPA

SPS

PEO

SYNTHESIS OF OLIGO/POLY(CATECHINS) AND METHODS OF USE

RELATED APPLICATIONS PARAGRAPH

This application is a continuation of International Application No. PCT/US2006/015872, which designated the United States and was filed on Apr. 27, 2006, published in English, which claims the benefit of U.S. Provisional Application No. 60/675,822, filed on Apr. 28, 2005. The entire teachings of the above application are incorporated herein by reference.

GOVERNMENT SUPPORT

The invention was supported, in whole or in part, by a grant DAAD 16-01-C-0011 from the Nanomaterials Science Team, U.S Army RDECOM Natick Soldier Center. The Government has certain rights in the invention.

BACKGROUND OF THE INVENTION

Natural products in green tea have attracted a great deal of attention because of anti-oxidant and anti-cancer activity ("Chemoprotection: A Review of the potential therapeutic antioxidant properties of green tea (Camellia sinensis) and certain of its constituents" Mitscher, L. A.; Jung, M.; Shankel, D.; Dou, J. H.; Steele, L.; Pillai, S. P Medicinal Research Reviews, 17(4), 327, 1997). The anti-oxidant and anti-cancer activity is believed to be due to flavonoids or catechin phenolic antioxidants. The major catechins in green tea are (−)-epicatechin, (+)-catechin, (−)-catechin, (−)-epicatechin gallate, (−)-epigallocatechin gallate (EGCG) and (−)-epigallocatechin.

Recent studies have revealed that the naturally occurring catechins can inhibit some forms of breast cancer cell proliferation ("Estrogen receptor-mediated actions of polyphenolic catechins in vivo and in vitro" Goodin, M G.; Fertuck, K. C.; Zacharewski T. R.; Rosengren, R. J" Toxicological sciences, 69(2), 354, 2002) and tumor growth and prevent recurrence in some forms of Stage I-II breast cancer in women (Green tea polyphenols and cancer chemoprevention: multiple mechanisms and endpoints for Phase II Trials Moyers, S. B.; Kumar, N. B. Nutrition reviews, 62(5), 204, 2004).

Naturally occurring green tea catechins have also been used as chemopreventive agents for skin cancer ("Cutaneous photochemoprotection by green tea: A brief review" Ahmad, N.; Mukhtar, H. Skin Pharmacol Appl Skin Physiol, 14(2), 69, 2001), against colon cancer ("Green tea constituent (−)-epigallocatechin-3-gallate inhibits topoisomerase I activity in human colon carcinoma cells" Berger, S. J.; Gupta, S.; Belfi, C. A.; Gosky, D. M.; Mukhtar, H Biochemical and Biophysical Research Communications, 288(1), 101, 2001) and are believed to reduce the risk of cancer of the pancreas, rectum ("Green tea consumption and the risk of pancreatic and colorectal cancers" Ji, B. T.; Chow, W. H.; Hsing, A. W.; McLaughlin, J. K.; Dai. Q.; Gao, Y. T.; Blot, W. J.; Fraumeni, J. F Jr Int. J. Cancer, 70(3), 255, 1997) and lungs ("Cancer inhibition by green tea" Fujiki, H.; Suganuma, M.; Okabe, S.; Sueoka, N.; Komori, A.; Sueoka, E.; Kozu, T.; Tada, Y.; Suga, K.; Imai, K.; Nakachi, Kei Mutation Research, 402, 307, 1998). These flavonoids have also found to possess other desirable properties such as anti-inflammatory, antiallergic, antithrombotic and antiviral properties ("Flavonoids as anticancer agents: Structure-Activity Relationship study" Lopez-Lazaro, M.; Curr. Med. Chem.—Anti-Cancer Agents, 2, 691, 2002).

In particular, EGCG has been shown to have pleotrophic effects in the inhibition of tumor angiogenesis and the prevention of cancer metastasis by interfering with proteases, urokinase and matrix metalloproteinase (MMP) activation, as well as direct inhibition of MMP secretion by tumor cells (Demeule, M., Michaud-Levesque, J., Annabi, B., Gingras, D., Boivin, D., Jodoin, J. Lamy, S., Bertrand, Y. and Beliveau, R. "Green Tea Catechins as Novel Antitumor and Antiangiogenic Compounds" Curr. Med. Chem.—Anti-Cancer Agents, 2002, 2, 441-463).

Naturally occurring flavanoids have also been evaluated for effects against cardiac damage, viral infection, and obesity (Suzuki J, Ogawa M, Sagesaka Y M, Isobe M. 2005. Catechins attenuate myocardial cell infiltration and fibrosis but do not prolong graft survival in murine cardiac allografts. Transplant Proc. January-February; 37(1):119-20; Liu S, Lu H, Zhao Q, He Y, Niu J, Debnath A K, Wu S, Jiang S. 2005. Theaflavin derivatives in black tea and catechin derivatives in green tea inhibit HIV-1 entry by targeting gp41. Biochim Biophys Acta. April 6; Wolfram S, Raederstorff D, Wang Y, Teixeira S R, Elste V, Weber P. 2005. TEAVIGO (Epigallocatechin Gallate) Supplementation Prevents Obesity in Rodents by Reducing Adipose Tissue Mass. Ann Nutr Metab. 49(1):54-63).

However, there are major disadvantages to the use of naturally occurring flavanoids such as EGCG. For example, it is known to be highly unstable in the vehicles used to solubilize it, such as ethanol or dimethyl sulfoxide (DMSO), losing activity within hours. Moreover, EGCG must typically be used at concentrations of 5-40 µg/mL to maintain activity, and is typically not at doses of 0.1 µg/mL.

Oligomerization of catechins has been reported to significantly enhance their anti-oxidant activity (Kurisawa, M.; Chung, J. E.; Kim, Y. J.; Uyama, H; Kobayashi, S. "Amplification of antioxidant activity and Xanthine Oxidase Inhibition of Catechin by enzymatic polymerization" Biomacromol., 2003, 4(3), 469-471). However these oligomerized forms of catechins are partly insoluble, which limits effective delivery into biological systems. Moreover, without purification from their reaction mixtures, they can be incompatible with biological systems. As the need for new and effective pharmaceuticals continues to grow, there is also concern over the environmental impact of toxic starting materials, intermediates, byproducts, solvents, and the like in the synthesis of new pharmaceuticals, which can also impair the biocompatibility, requiring additional purification.

Therefore, there is a need in the art for new methods of synthesizing biocompatible, soluble catechins that have improved biological activity. Moreover there is a need for methods of synthesizing these agents that is simple and environmentally benign.

SUMMARY OF THE INVENTION

Disclosed are methods of synthesizing oligo/polyflavanoids that have increased anticancer activity compared to monoflavanoids. These oligo/polyflavanoids in general are biocompatible, are synthesized by biocompatible processes and are water-soluble. See Examples 1-7 for improved synthesis and Examples 8-13 for increased anticancer activity.

In one embodiment the present invention is a polymer comprising at least two repeat units independently selected from the group consisting of:

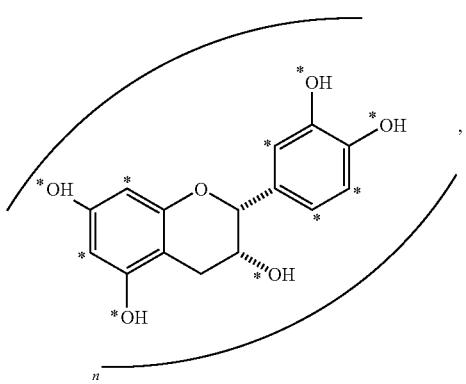

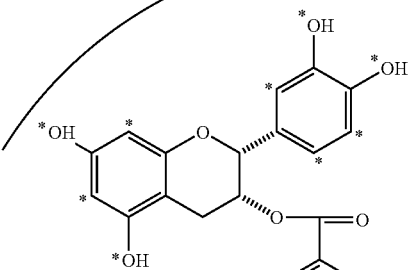

and

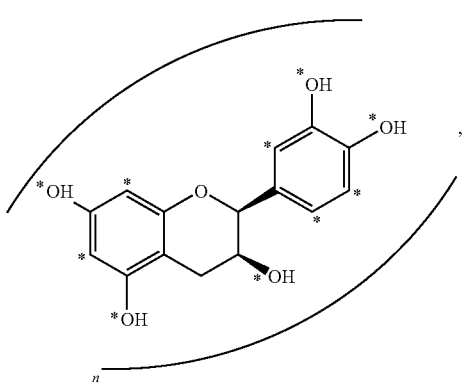

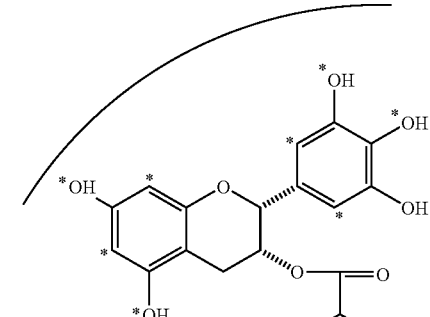

,

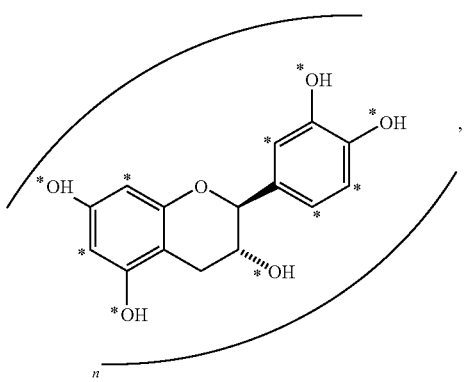

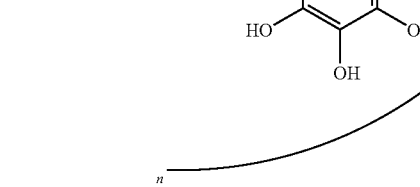

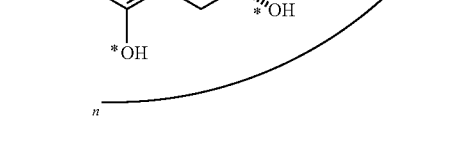

or a pharmaceutically acceptable salt thereof. Each repeat unit is independently optionally substituted with one or more substituents, and between one and four —H atoms in each repeat unit attached to the oxygen or carbon at each * are independently replaced by a polymer link. Each n is independently an integer from 0 to 170 inclusive, wherein the sum of all ns is an integer from 2 to 170 inclusive.

In another embodiment the present invention is a biocompatible composition comprising a biocompatible solvent and an oligo/polyflavanoid or a pharmaceutically acceptable salt, solvate, or complex thereof.

In another embodiment the present invention is a method for synthesizing a polymer comprising polymerizing an optionally substituted flavanoid, phenolic acid, hydroxycinnamic acid or phytochemical with a polymerization agent in the presence of a biocompatible polymerization solubilizer.

In another embodiment the present invention is a method for synthesizing a oligo/polyflavanoid comprising polymerizing a flavanoid with a polymerization agent in the presence of an amphiphile.

In another embodiment the present invention is a method for synthesizing a water-soluble oligo/polyflavanoid having a UV-visible spectrum including a peak between 350 and 450 nm comprising polymerizing a flavanoid with a polymerization agent in the presence of a polymerization solubilizer.

In another embodiment the present invention is a method of synthesizing a polymer comprising at least two repeat units independently selected from the group consisting of:

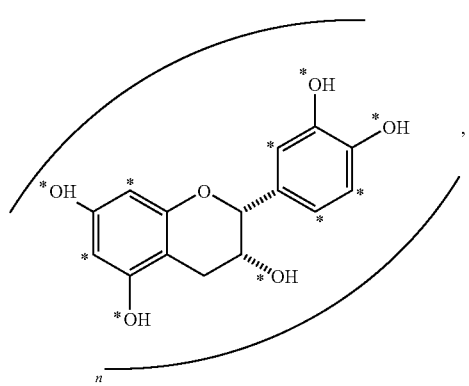

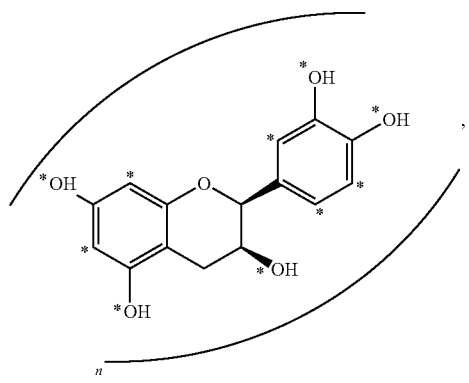

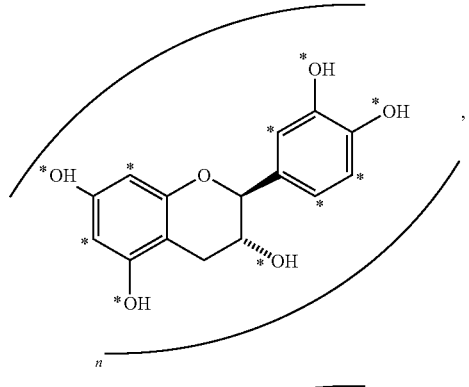

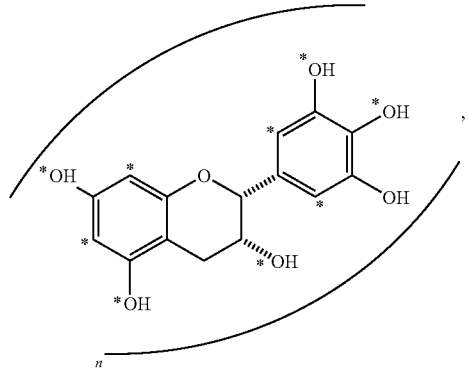

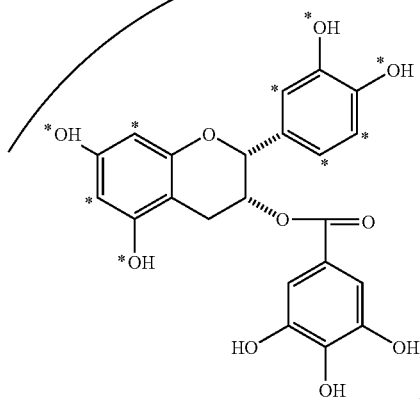

or a pharmaceutically acceptable salt thereof. Each repeat unit is independently optionally substituted with one or more substituents, and between one and four —H atoms in each repeat unit attached to the oxygen or carbon at each * are independently replaced by a polymer link. Each n is independently an integer from 0 to 170 inclusive, wherein the sum of all ns is an integer from 2 to 170 inclusive. The method comprises polymerizing the repeat unit with a polymerization agent in the presence of a polymerization solubilizer.

In another embodiment the present invention is a method of inhibiting the onset of or treating cancer in a subject in need thereof comprising administering to the subject a therapeutically effective amount of a polymer described herein.

In another embodiment the present invention is a method of treating cardiac damage in a subject in need thereof, comprising administering to the subject a therapeutically effective amount of a polymer described herein.

In another embodiment the present invention is a method of treating a viral infection in a subject in need thereof, comprising administering to the subject a therapeutically effective amount of a polymer described herein.

In another embodiment the present invention is a method of treating obesity in a subject in need thereof, comprising administering to the subject a therapeutically effective amount of a polymer described herein.

The disclosed oligo/polyflavanoids, complexes of oligo/polyflavanoids, methods of synthesis, and methods of treating cancer have numerous advantages. Solubility and biocompatibility problems associated with oligo/polyphenols, which has in the past greatly limited the commercial and clinical use of these polymers are addressed by the disclosed invention.

The disclosed oligo/polyflavanoids in general also show enhanced biological activity. For example, oligo/polyflavanoids prepared by the disclosed methods show anticancer activity against MCF-7 (human, low metastatic, +ER, breast cancer cells) and MDA-MB-231 (human, high metastatic, −ER, breast cells) in vitro. These oligo/polyflavanoids can be effective at a significantly lower dose (0.1 μg/mL) compared to the monomeric flavanoid EGCG, which only exhibited activity at doses between 1-40 μg/mL. Moreover, the oligo/polyflavanoids did not affect the proliferation of normal mammary epithelial cells (MCF12A cells), and thus may be capable of achieving a high therapeutic ratio. Further, the activity of the disclosed oligo/polyflavanoids can be more stable (up to 3 months) compared to EGCG which can lose activity within 1 hour of dissolving in solvent.

Moreover, the methods proposed here in general do not involve the use of toxic chemicals or solvents and hence there are typically no harmful by-products formed in the process. Enzymatic embodiments provide a simple, "one-pot" green reaction that can yield oligo/polyflavanoid products with potential pharmaceutical applications.

Additionally, the starting materials, intermediates and the products obtained are in general all biocompatible and therefore do not require any waste treatment. Further, the resulting oligo/polyflavanoids are typically biocompatible as-synthesized.

DETAILED DESCRIPTION OF THE INVENTION

Figure 1:
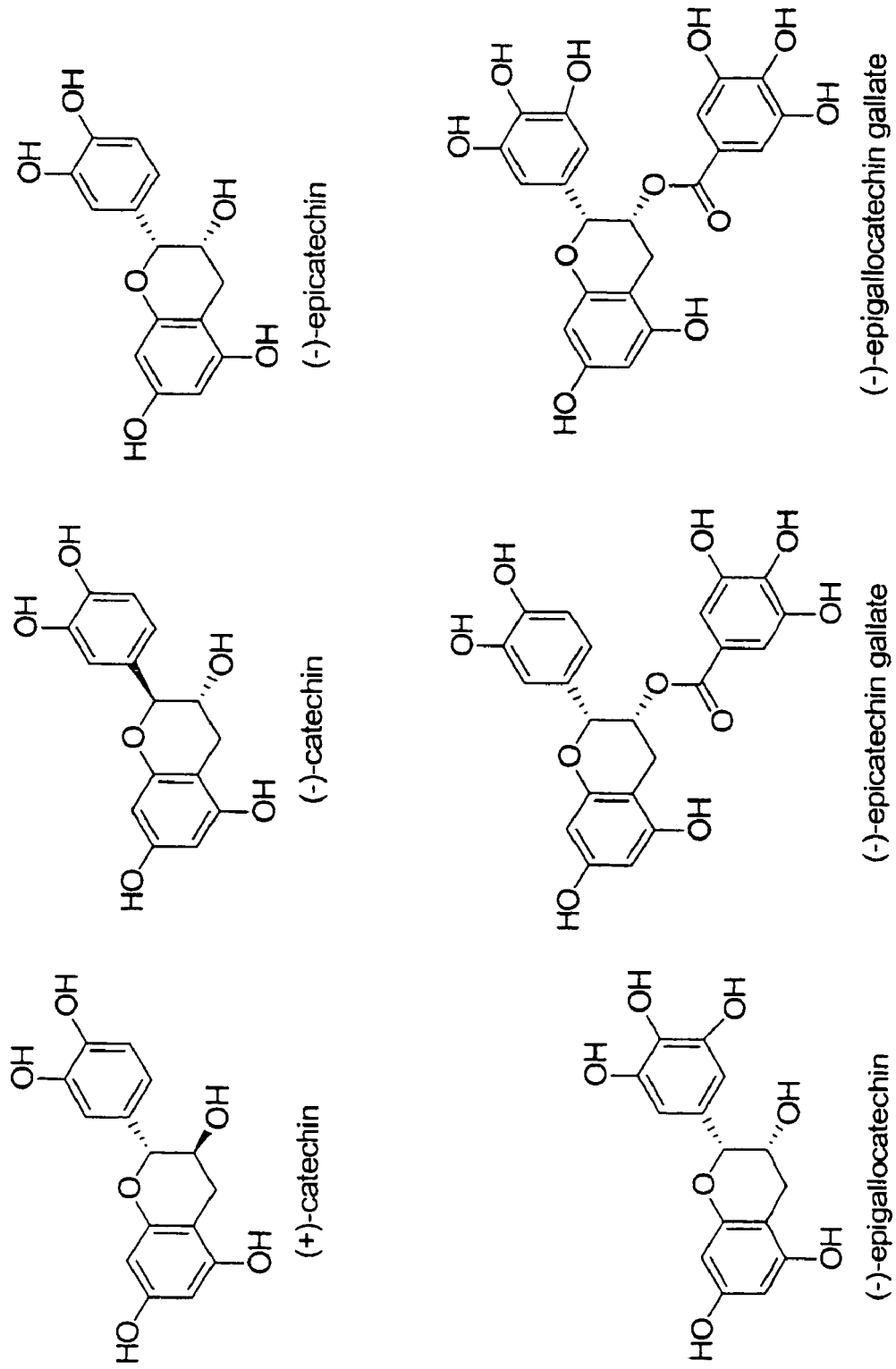
FIG. 1 shows the chemical structure of some naturally occurring green tea catechins.

A description of preferred embodiments of the invention follows.

The present invention relates in one embodiment to an enzymatic polymerization process of various flavonoids, in particular the stereoisomers of catechins in the presence of biocompatible templates like Polyethylene oxide (PEO), sulfonated polystyrene (SPS), or other templates such as sodium dodecylbenzene sulfonic acid (DBSA), or in mixed solvent systems such as water-ethanol mixtures to yield novel soluble oligo/poly(catechins). The oligo/poly(catechins) synthesized are stable and can be easily delivered into biological systems.

As used herein, the prefix "oligo" as in the term "oligoflavanoid" means molecules having two or more repeat units such as oligomers. For example, an oligoflavanoid can have from about 2 to about 9 repeating flavanoid units, typically from about 5 to about 9 repeating flavanoid units. As used herein, the prefix "poly" as in the term "polyflavanoid" means molecules having two or more repeat units such as polymers and oligomers. For example, a polyflavanoid can have from about 10 to about 1000 repeating flavanoid units, typically from about 10 to about 500 repeating flavanoid units, more typically from about 10 to about 170 repeating flavanoid units more typically from about 10 to about 50 repeating flavanoid units. Thus, as used herein, the prefix "oligo/poly" as in the term "oligo/polyflavanoid" means molecules having two or more repeat units such as polymers and oligomers. For example, an oligo/polyflavanoid can have from about 2 to about 1000 repeating flavanoid units, typically from about 5 to about 500 repeating flavanoid units, more typically from about 5 to about 170 repeating flavanoid units, more typically from about 5 to about 50 repeating flavanoid units. In some embodiments, the oligo/polyflavanoid has about 2 to about 170 repeating flavanoid units. In some embodiments, the oligo/polyflavanoids herein are oligoflavanoids. In some embodiments, the oligo/polyflavanoids herein are polyflavanoids.

As used herein, a "flavanoid" includes naturally occurring phenols that are commonly termed flavanoids and unnatural isomers or optionally substituted variations thereof. For example, flavanoids can be selected from optionally substituted catechin, quercitin, flavonone, isoflavone, chalcone, anthocyanidin, chrysin, primuletin, fisetin, naringin, hesperidin, prunin, daidzein, genistein, pelargonidin, cyaniding, delphinidin, or the like. In various embodiments, the flavanoid is selected from (−)-catechin, (−)-epicatechin, (−)-gallocatechin, (−)-catechin gallate, (−)-epigallocatechin, (−)-gallocatechin gallate, (−)-epicatechin gallate, (−)-epigallocatechin gallate, (+)-catechin, (+)-epicatechin, (+)-gallocatechin, (+)-catechin gallate, (+)-epigallocatechin, (+)-gallocatechin gallate, (+)-epicatechin gallate, and (+)-epigallocatechin gallate, whereby the oligo/polyflavanoid synthesized can be oligo/poly(−)-catechin, oligo/poly(−)-epicatechin, oligo/poly(−)-gallocatechin, oligo/poly(−)-catechin gallate, oligo/poly(−)-epigallocatechin, oligo/poly(−)-gallocatechin gallate, oligo/poly(−)-epicatechin gallate, oligo/poly(−)-epigallocatechin gallate, oligo/poly(+)-catechin, oligo/poly(+)-epicatechin, oligo/poly(+)-gallocatechin, oligo/poly(+)-catechin gallate, oligo/poly(+)-epigallocatechin, oligo/poly(+)-gallocatechin gallate, oligo/poly(+)-epicatechin gallate, or oligo/poly(+)-epigallocatechin gallate.

FIG. 1 shows the chemical structure of some naturally occurring green tea flavanoids.

In some embodiments, the flavanoid is (−)-catechin or (+)-catechin, whereby the biocompatible, soluble oligo/polyflavanoid is oligo/poly(−)-catechin or oligo/poly(+)-catechin. In particular embodiments, the flavanoid is (−)-epicatechin or (+)-epicatechin, whereby the biocompatible, soluble oligo/polyflavanoid is oligo/poly(−)-epicatechin or oligo/poly(+)-epicatechin.

In certain embodiment the present invention is a polymer (oligo/polyflavanoid) comprising at least two repeat units independently selected from the group consisting of:

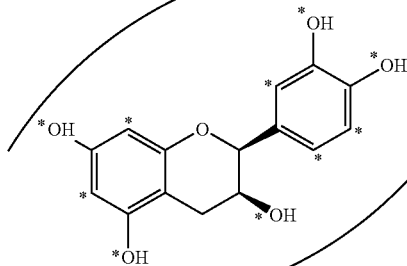

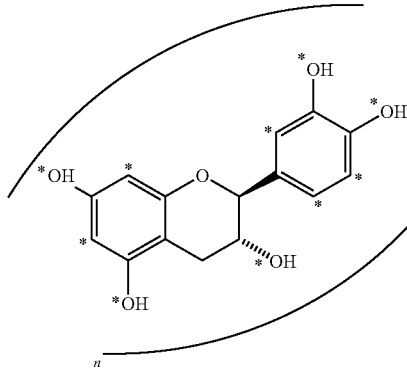

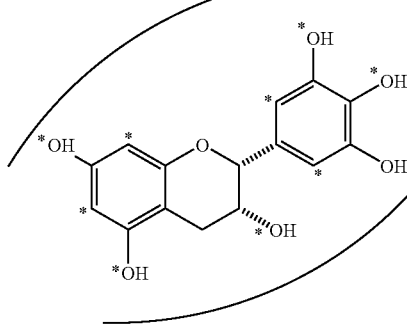

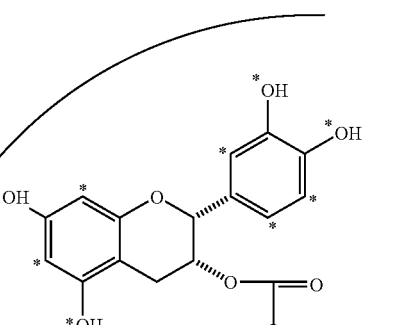

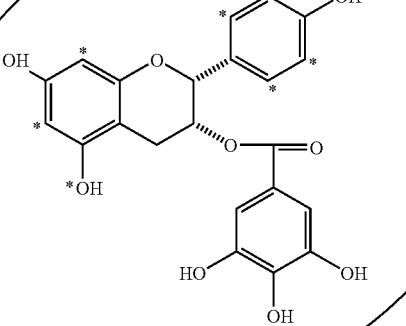

and

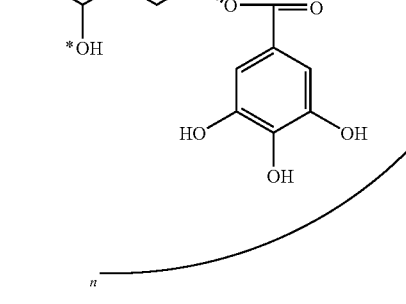

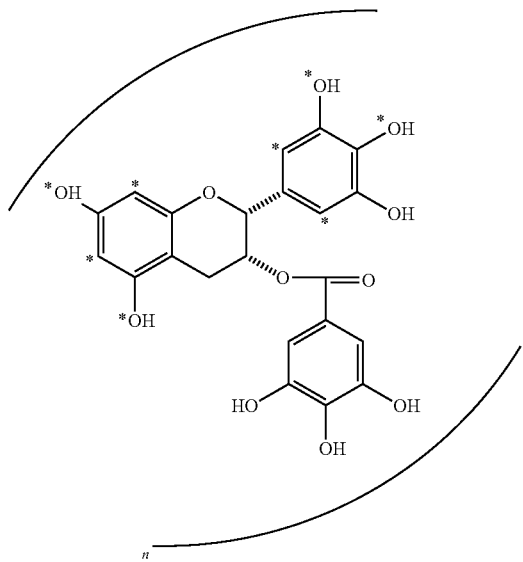

or a pharmaceutically acceptable salt thereof.

Each repeat unit is independently optionally substituted with one or more substituents, and between one and four —H atoms in each repeat unit attached to the oxygen or carbon at each * are independently replaced by a polymer link; in certain embodiments 2 —H atoms are replaced by a polymer link.

Each n is independently an integer from 0 to 170 inclusive, wherein the sum of all ns is an integer from 2 to 170 inclusive. In certain embodiments the sum of all ns is an integer from 10 to 170 inclusive.

In certain embodiments the polymer is a copolymer.

In certain embodiments the polymer is a copolymer wherein the repeat units are:

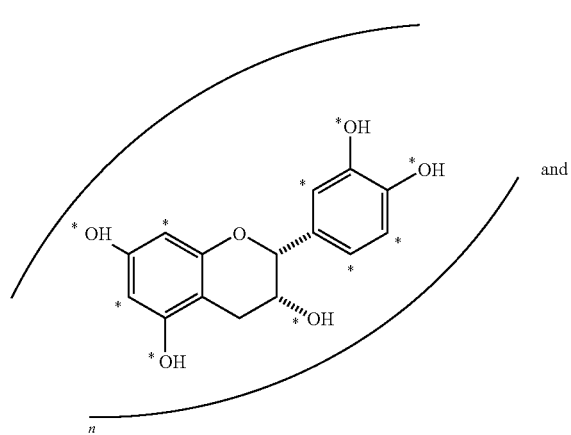

and

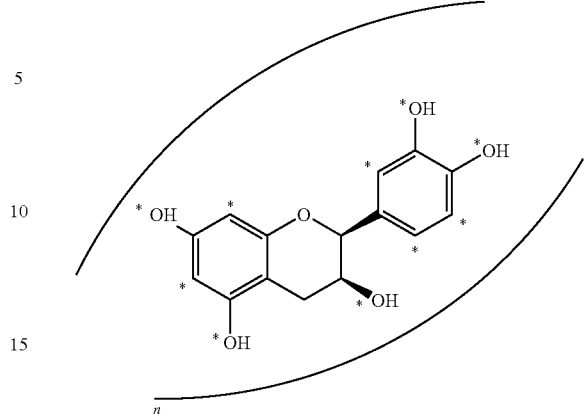

or a pharmaceutically acceptable salt thereof each repeat unit is independently optionally substituted with one or more substituents. n is as defined above.

In certain embodiments the polymer is a copolymer wherein the repeat units are:

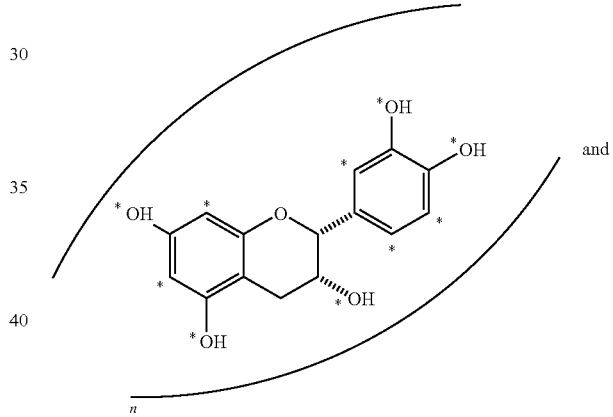

and

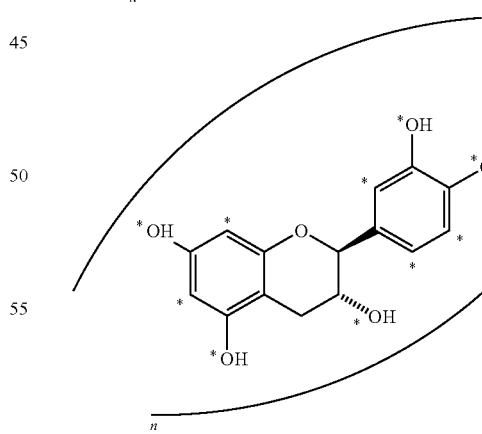

, or a pharmaceutically acceptable salt thereof. Each repeat unit is independently optionally substituted with one or more substituents. n is as defined above.

In certain embodiments the polymer is a copolymer wherein the repeat units are:

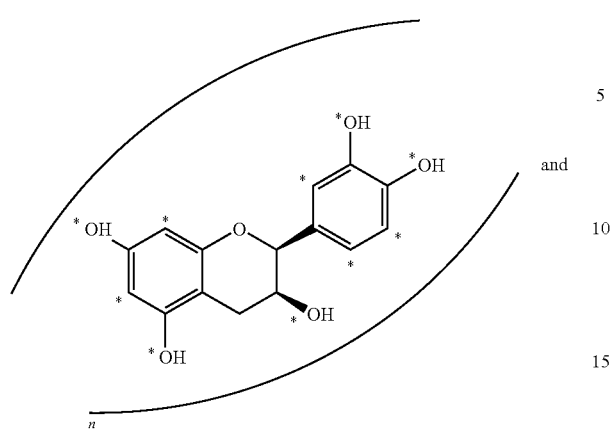
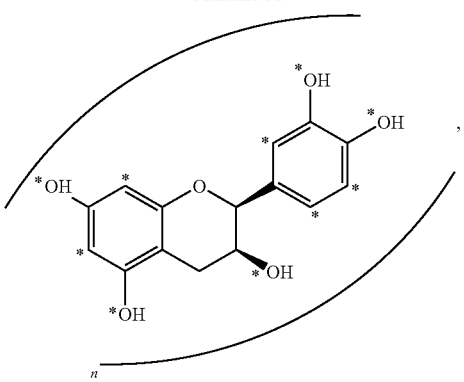
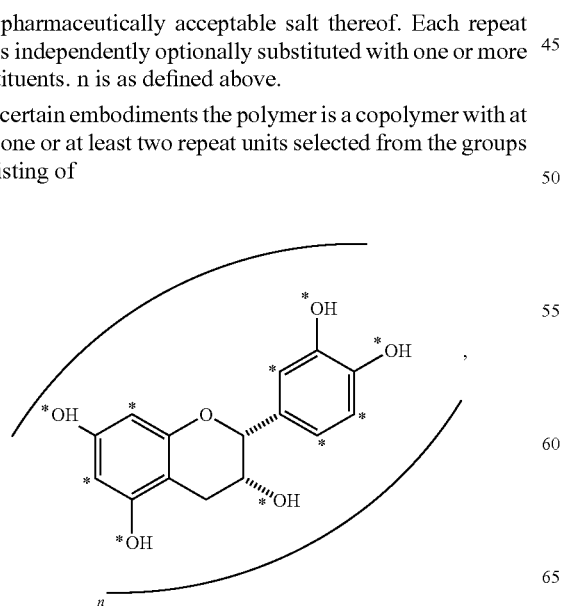
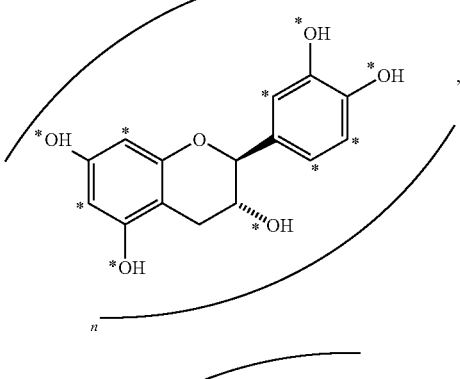
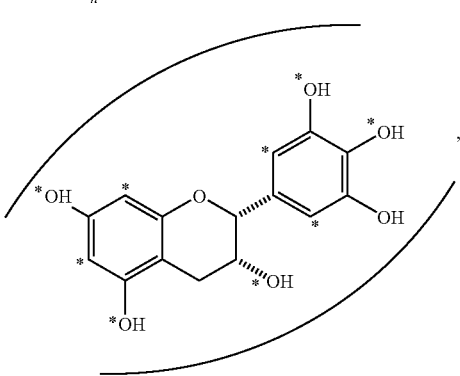
or a pharmaceutically acceptable salt thereof. Each repeat unit is independently optionally substituted with one or more substituents. n is as defined above.
In certain embodiments the polymer is a copolymer with at least one or at least two repeat units selected from the groups consisting of
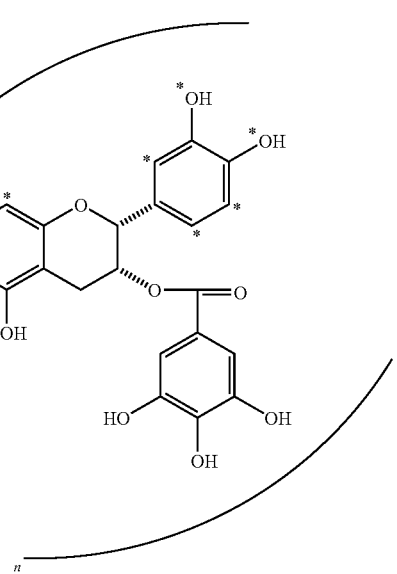

-continued

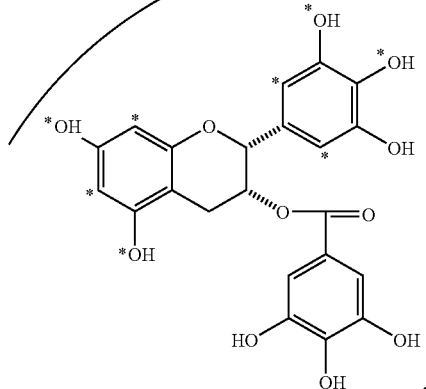

and a further repeat unit represented by:

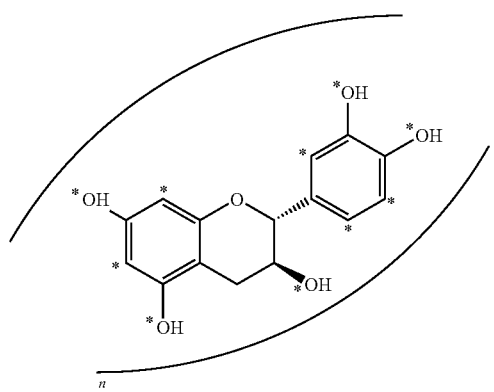

or a pharmaceutically acceptable salt thereof. Each repeat unit is independently optionally substituted with one or more substituents. n is as defined above.

In certain embodiments the polymer is a copolymer wherein the repeat units are:

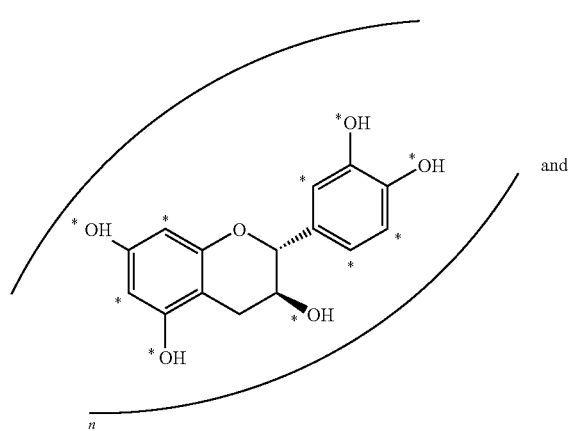

and

-continued

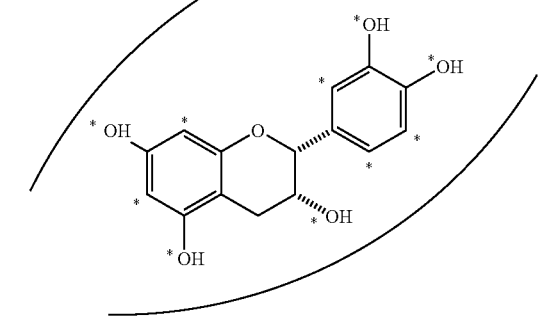

or a pharmaceutically acceptable salt thereof. Each repeat unit is independently optionally substituted with one or more substituents. n is as defined above.

In certain embodiments the polymer is a copolymer wherein the repeat units are:

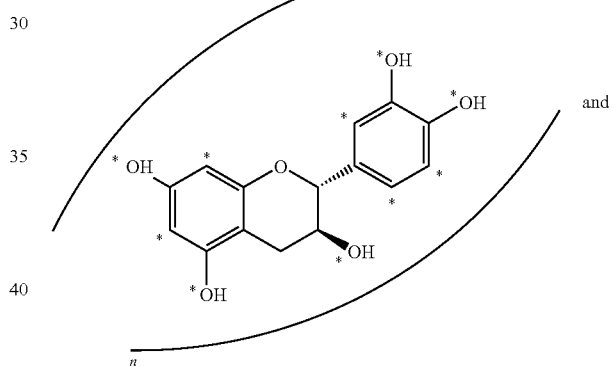

and

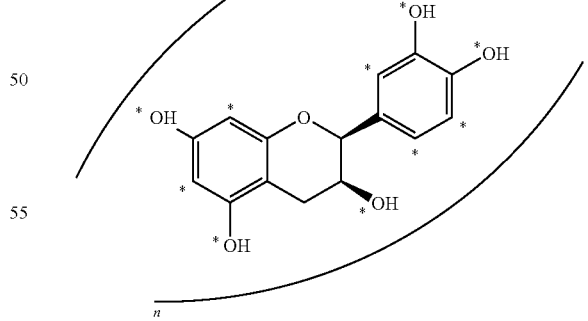

or a pharmaceutically acceptable salt thereof. Each repeat unit is independently optionally substituted with one or more substituents. n is as defined above.

In certain embodiments in the polymers of the present invention each repeat unit is represented by the following structural formula:

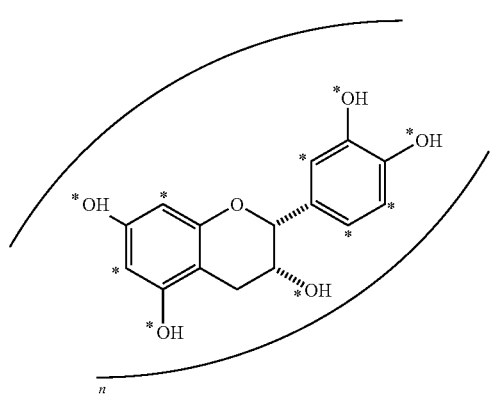
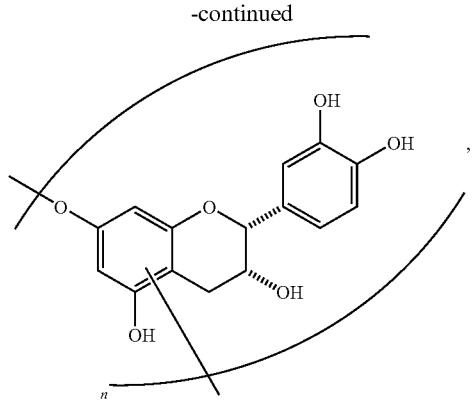
or a pharmaceutically acceptable salt thereof, wherein each repeat unit is independently optionally substituted with one or more substituents. n is as defined above.
In certain embodiments in the polymers of the present invention each repeat unit is independently selected from the group consisting of:
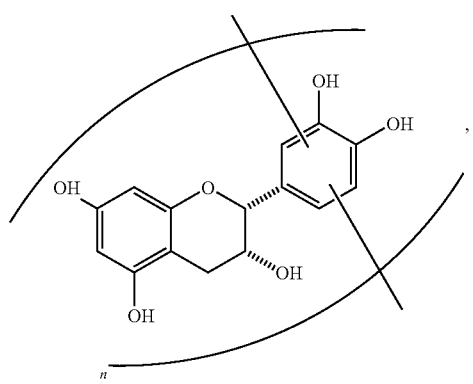
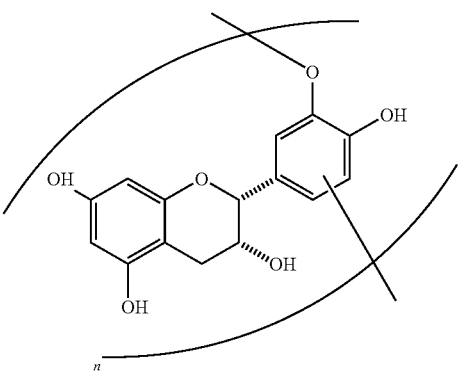
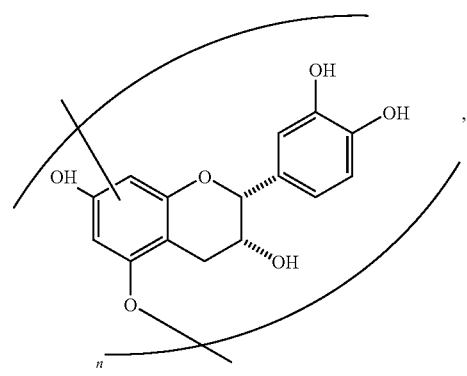
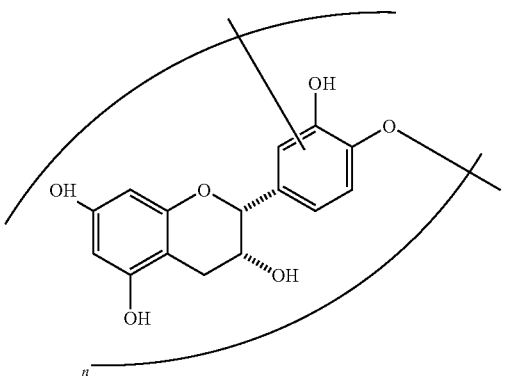
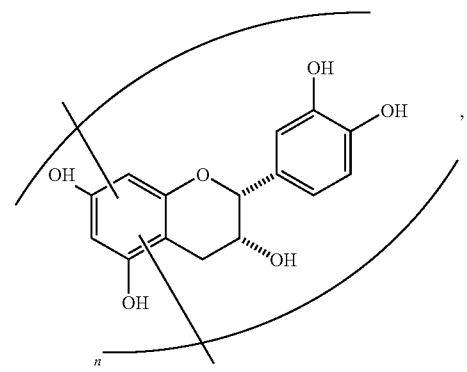
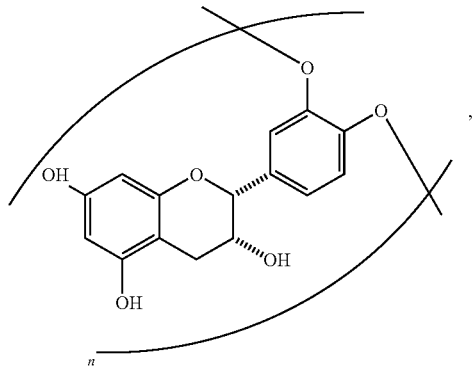

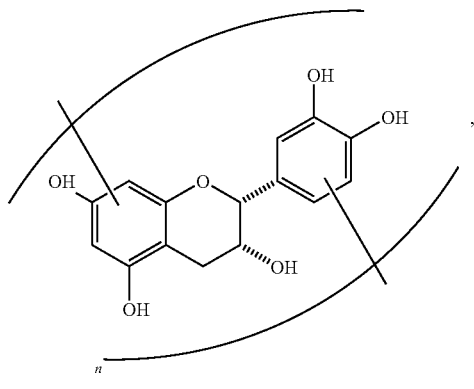
,
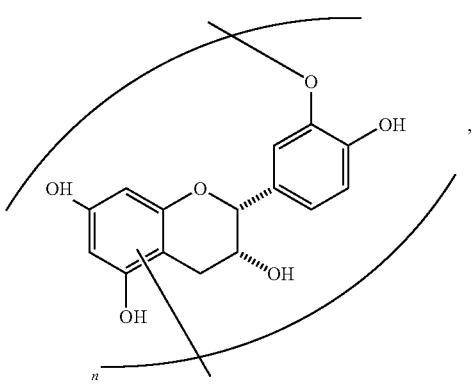
,
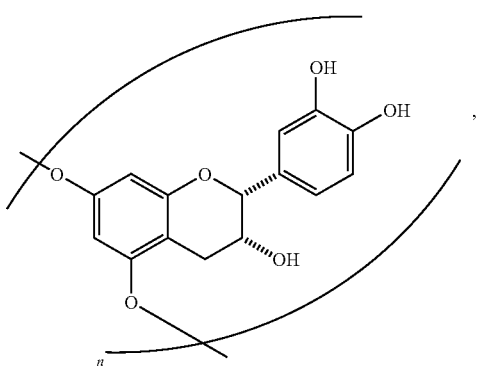
,
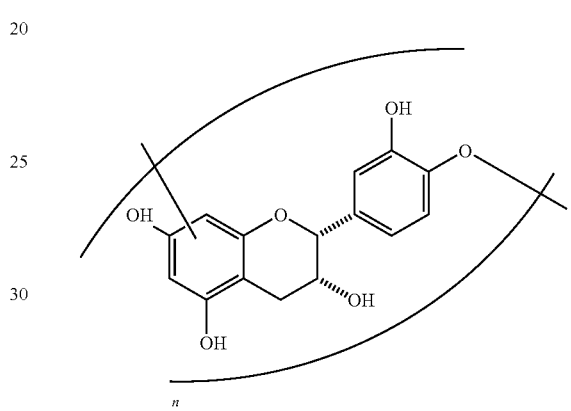
,
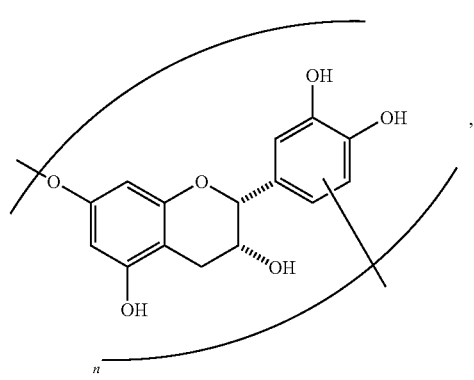
,
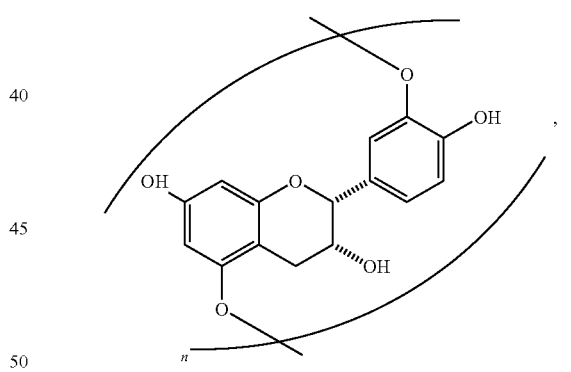
,
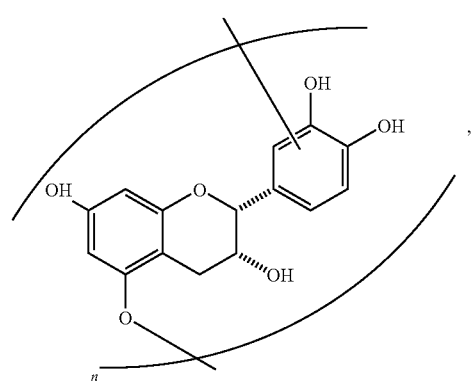
,
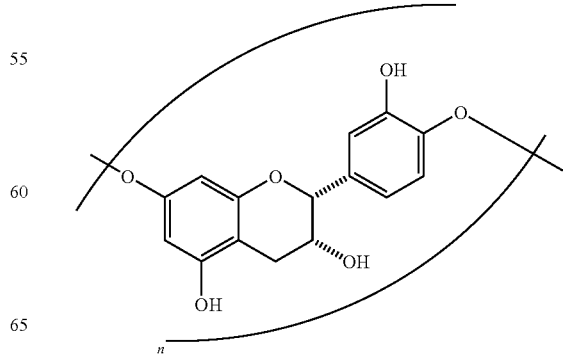
,

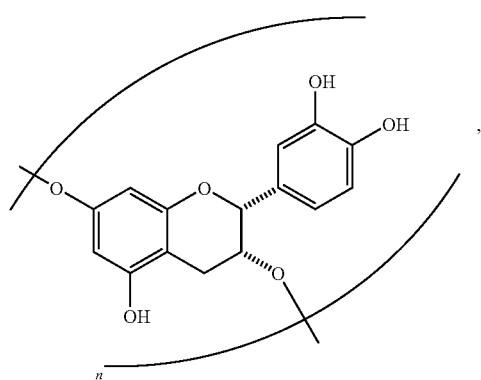
,
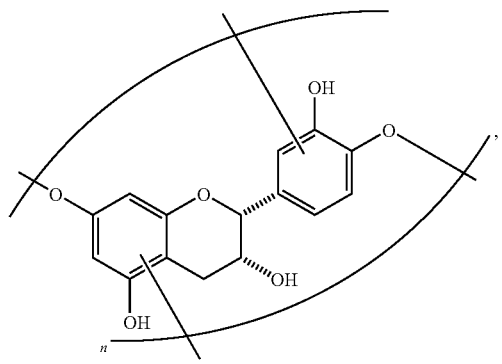
,
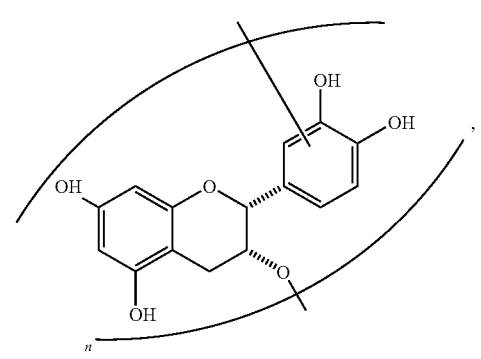
,
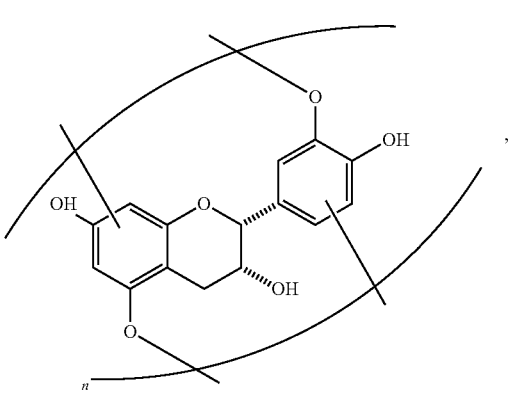
,
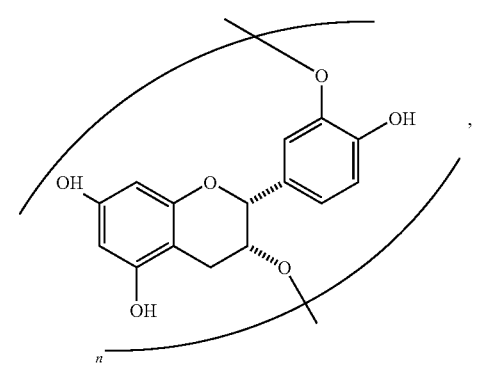
,
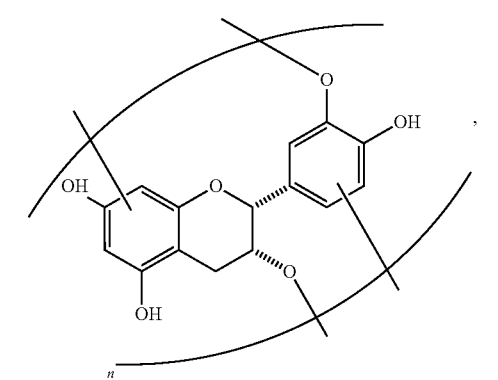
,
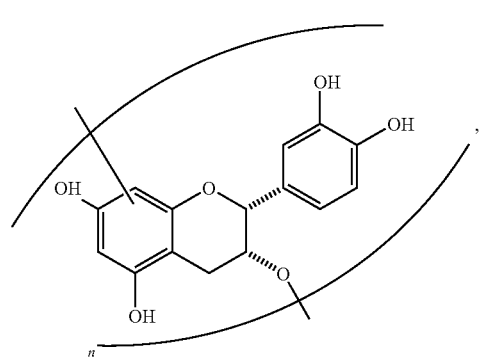
,
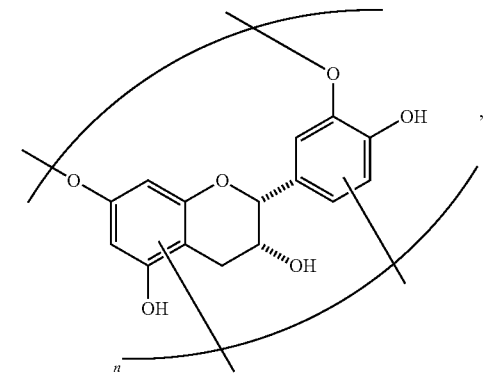
,

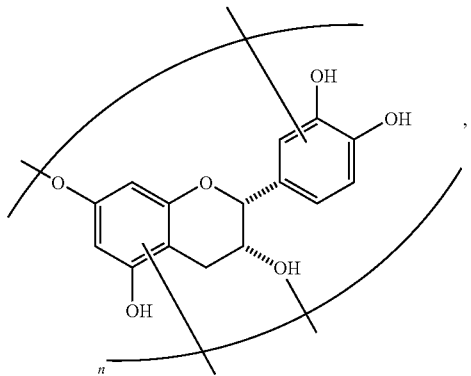
,

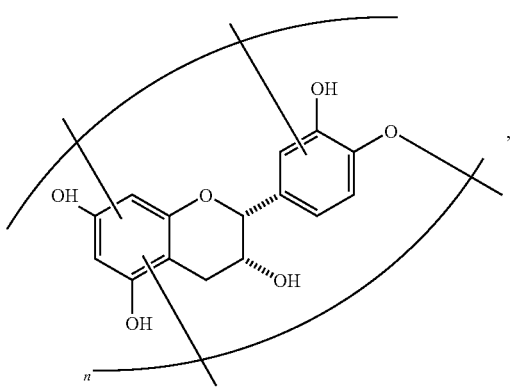
,

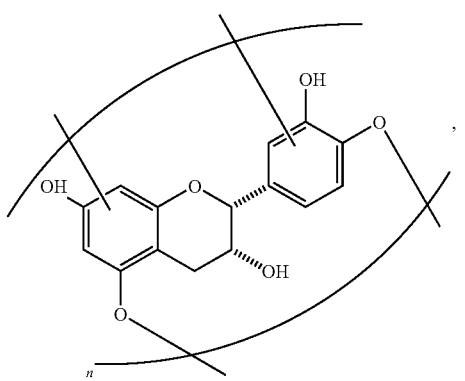
,

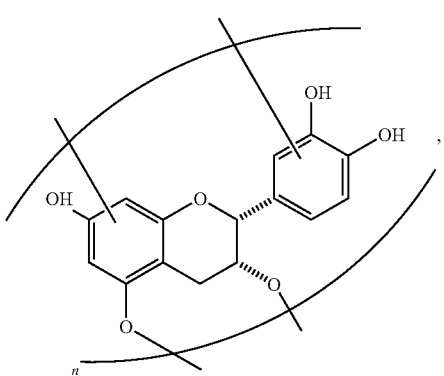
,

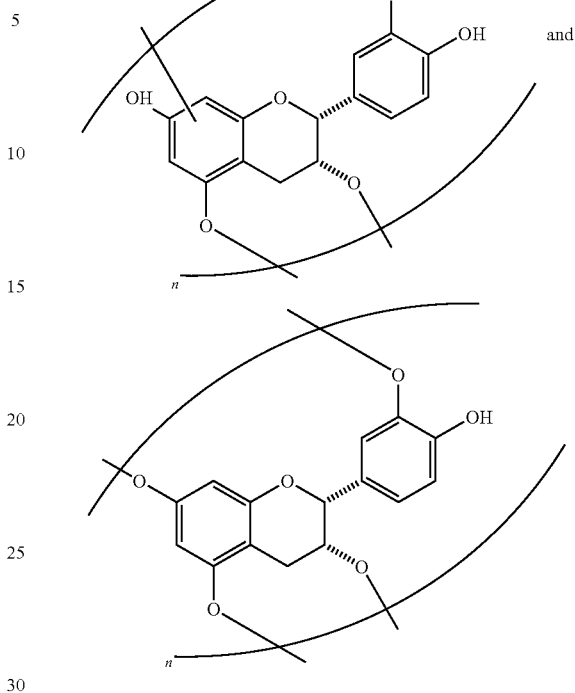

or a pharmaceutically acceptable salt thereof, wherein each repeat unit is independently optionally substituted with one or more substituents. n is as defined above.

In certain embodiments the polymers (oligo/polyflavanoids) of the present invention have a UV-visible spectrum including a peak between 350 and 450 nm.

In certain embodiments the polymers (oligo/polyflavanoids) of the present invention have a solubility in 1 mL of water of between 0.5 and 5 mg at room temperature.

In certain embodiments the polymers (oligo/polyflavanoids) of the present invention have a solubility in 1 mL of water of between 1 and 3 mg at room temperature.

In certain embodiments the polymers (oligo/polyflavanoids) of the present invention have an average molecular weight of between 3,000 and 50,000 Daltons.

In certain embodiments the polymers (oligo/polyflavanoids) of the present invention have an average molecular weight of between 10,000 and 50,000 Daltons.

In certain embodiments in the polymers (oligo/polyflavanoids) of the present invention the majority of the repeat units are the same enantiomer, whereby the polymer is chiral.

In certain embodiments in the polymers (oligo/polyflavanoids) of the present invention substantially all the repeat units of the polymer are the same enantiomer, whereby the oligo/polyflavanoid is chiral.

In certain embodiments in the polymers (oligo/polyflavanoids) of the present invention wherein all the repeat units of the polymer are the same enantiomer, whereby the oligo/polyflavanoid is chiral.

In certain embodiments in the polymers (oligo/polyflavanoids) of the present invention one or more repeat units are substituted with one or more substituents independently selected from —F, —Cl, —Br, —I, —CN, —NO$_2$, —OR$^a$, —C(O)R$^a$, —OC(O)R$^a$, —C(O)OR$^a$, —SR$^a$, —C(S)R$^a$, —OC(S)R$^a$, —C(S)OR$^a$, —C(O)SR$^a$, —C(S)SR$^a$, —S(O)R$^a$, SO$_2$R$^a$, —SO$_3$R$^a$, PO$_2$R$^a$R$^b$, —PO$_3$R$^a$R$^b$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), —C(NR$^c$)—N(R$^a$R$^b$), —NR$^d$—C(NR$^c$)—N(R$^a$R$^b$), —NR$^a$N(R$^a$R$^b$), —CR$^c$=CR$^a$R$^b$, —C≡CR$^a$, =O, =S, =CR$^a$R$^b$, =NR$^a$, =NOR$^a$, =NNR$^a$, optionally substituted alkyl, optionally substituted cycloalkyl, optionally substituted aliphatic, optionally substituted cycloaliphatic, optionally substituted heterocyclic, optionally substituted benzyl, optionally substituted aryl, and optionally substituted heteroaryl; wherein R$^a$-R$^d$ are each independently —H or an optionally substituted aliphatic, optionally substituted cycloaliphatic, optionally substituted heterocyclic, optionally substituted benzyl, optionally substituted aryl, or optionally substituted heteroaryl, or, —N(R$^a$R$^b$), taken together, is an optionally substituted heterocyclic group.

In certain embodiments in the polymers (oligo/polyflavanoids) of the present invention one or more repeat units are substituted with a biomolecule.

In certain embodiments in the polymers (oligo/polyflavanoids) of the present invention one or more repeat units are unsubstituted.

In certain embodiments in the polymers (oligo/polyflavanoids) of the present invention all repeat units are unsubstituted.

In various embodiments, the flavanoid monomer or monomers employed in the polymerization can be enantiomerically pure. As used herein, a sample of a compound that is "enantiomerically pure" can have a majority of one enantiomer of the compound, typically at least about 80% of one enantiomer of the compound, or more typically at least about 90%, 95%, 97%, 98%, 99%, 99.5%, or 99.9% one enantiomer of the compound.

In certain embodiment the stereochemistry of the flavanoid is retained in the oligo/polyflavanoid of the present invention.

In various embodiments, a plurality of optionally substituted flavanoids can be co-polymerized, or one or more optionally substituted flavanoids and an optionally substituted phenol can be copolymerized, whereby the biocompatible, soluble oligo/polyflavanoid is a co-oligo/polymer. A co-oligo/polymer can be made from a copolymerized mixture of monomers, which can lead to formation of a mixed or random co-oligo/polymer; or a co-oligo/polymer can be made by sequential addition of different monomers to the polymerization mixture, whereby a block co-oligo/polymer can be synthesized; or the like. In another example, polyethylene glycol chains (optionally terminated with carboxyl groups) can be attached to the flavanoid monomers using simple coupling chemistry or lipases. These functionalized flavanoids can be co-polymerized along with any substituted or unsubstituted flavanoid. can be carried through hydrolytic enzymes like lipases or using simple coupling chemistry. Examples of co-oligo/polymers include pegylated catechins copolymerized with catechins; random copolymers of different flavanoid monomers; alternating copolymers of different flavanoid monomers; block copolymers of different flavanoid monomers; and the like.

In various embodiments, the oligo/polyflavanoid can be chiral. In some embodiments, the oligo/polyflavanoid chirality can be due to retention of the stereochemistry of the flavanoid monomers. In some embodiments, the oligo/polyflavanoid chirality can be different from the stereochemistry of the flavanoid monomers.

Figure 2:
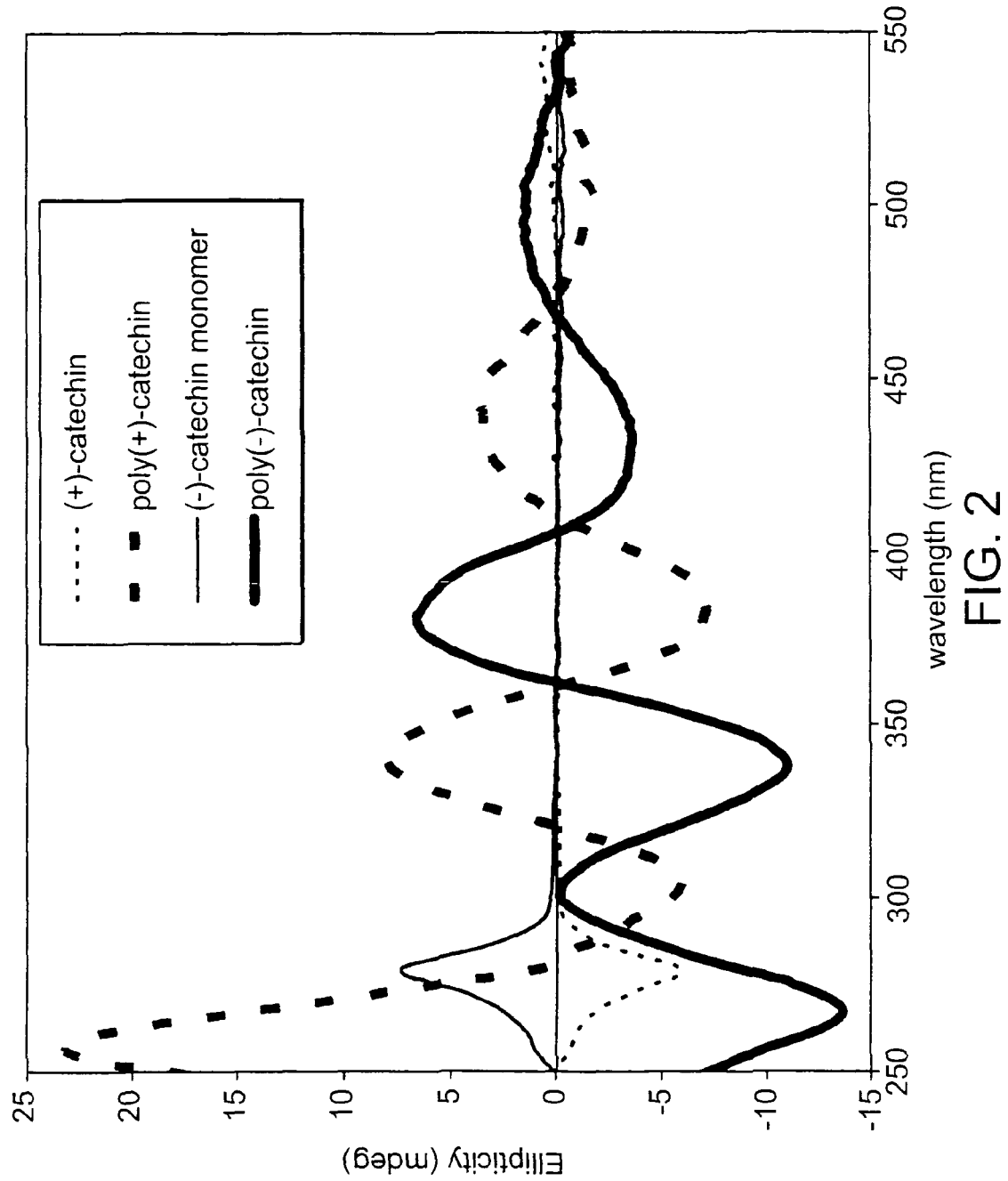
FIG. 2 is a circular dichroism spectrum of oligo/poly(+)-catechin and oligo/poly(−)-catechin. The polymerization of (+)-catechin and (−)-catechin leads to oligo/poly(+)-catechin and oligo/poly(−)-catechin, which have CD spectra that are near-mirror images of each other and correlate to their (+)-catechin and (−)-catechin monomers, respectively.

The chirality of the oligo/polyflavanoid product can be examined by methods that can distinguish chiral oligo/polymers, for example, by chiral chromatography, nuclear magnetic resonance, circular dichroism (CD) spectroscopy, or the like. For example FIG. 2 is a circular dichroism spectrum of oligo/poly(+)-catechin and oligo/poly(−)-catechin. The oligo/polymerization of (+)-catechin and (−)-catechin leads to oligo/poly(+)-catechin and oligo/poly(−)-catechin, which have CD spectra that are near-mirror images of each other and correlate to their (+)-catechin and (−)-catechin monomers, respectively.

In some embodiments, the invention is a biocompatible, soluble, chiral oligo/polyflavanoid or a pharmaceutically acceptable salt, solvate, or complex thereof, provided that the oligo/polyflavanoid is not a natural product.

In various embodiments, the flavanoid monomers and the oligo/polyflavanoids can be optionally substituted as described under suitable optional substituents, below. The oligo/polyflavanoids can be substituted as a result of being synthesized from substituted flavanoid monomers, or can be substituted after synthesis. For example, the biocompatible, water-soluble oligo/polyflavanoid can be substituted with a biomolecule or other substituent via standard coupling chemistry, via enzymatic coupling via enzymatic coupling, e.g., using hydrolytic enzymes such as lipases (*Candida antartica* lipase/*candida rugosa* lipase/porcine pancreatic lipase, or the like). In various other embodiments, the flavanoid monomers and the oligo/polyflavanoids are not substituted.

In certain embodiments the present invention is a biocompatible, soluble oligo/polyflavanoid or a pharmaceutically acceptable salt, solvate or complex thereof, wherein the oligopolyflavanoid is described herein and may be complexed with an amphiphile.

In certain embodiments the present invention is a biocompatible composition comprising a biocompatible solvent and an oligo/polyflavanoid or a pharmaceutically acceptable salt, solvate, or complex thereof. In certain embodiments the oligo/polyflavanoid is as described above.

In certain embodiments in the biocompatible composition of the present invention the oligo/polyflavanoid comprises repeat units selected from the group consisting of optionally substituted catechin, quercitin, flavonone, isoflavone, chalcone, anthocyanidin, chrysin, primuletin, fisetin, naringin, hesperidin, prunin, daidzein, genistein, pelargonidin, cyanidin and delphinidin.

In certain embodiments in the biocompatible composition of the present invention the oligo/polyflavanoid is selected from oligo/poly(−)-catechin, oligo/poly(−)-epicatechin, oligo/poly(−)-gallocatechin, oligo/poly(−)-catechin gallate, oligo/poly(−)-epigallocatechin, oligo/poly(−)-gallocatechin gallate, oligo/poly(−)-epicatechin gallate, oligo/poly(−)-epigallocatechin gallate, oligo/poly(+)-catechin, oligo/poly(+)-epicatechin, oligo/poly(+)-gallocatechin, oligo/poly(+)-catechin gallate, oligo/poly(+)-epigallocatechin, oligo/poly(+)-gallocatechin gallate, oligo/poly(+)-epicatechin gallate, and oligo/poly(+)-epigallocatechin gallate.

In certain embodiments in the biocompatible composition of the present invention the oligo/polyflavanoid is oligo/poly(−)-catechin or oligo/poly(+)-catechin.

In certain embodiments in the biocompatible composition of the present invention the oligo/polyflavanoid is oligo/poly(−)-epicatechin or oligo/poly(+)-epicatechin.

In certain embodiments in the biocompatible composition of the present invention the oligo/polyflavanoid is oligo/poly(−)-epicatechin.

In certain embodiments in the biocompatible composition of the present invention the biocompatible solvent is a water/ethanol mixture.

In certain embodiments in the biocompatible composition of the present invention the oligo/polyflavanoid is complexed with an amphiphile. In certain embodiments the amphiphile can be useful in solubilizing the polymer of the present invention.

In certain embodiments in the biocompatible composition of the present invention the amphiphile is selected from the group consisting of polyethylene oxide, sulfonated polystyrene, poly (vinyl phosphonic acid), sodium dodecyl benzenesulfonate, polyoxyethylene(10), isooctylphenyl ether (Triton X-100), p-toluenesulphonic acid monohydrate, deoxyribonucleic acid, ribonucleic acid, 1-palmitoly-2-oleoyl-sn-glycerol-3-phosphate, sodium octylsulfonate, 1-palmitoly-2-oleoyl-sn-glycero-3-phosphocholine, and benzoyl-L-tyrosine-p-nitroanilde.

In certain embodiments in the biocompatible composition of the present invention the amphiphile is biocompatible.

In certain embodiments in the biocompatible composition of the present invention the amphiphile is selected from the group consisting of polyethylene oxide, sulfonated polystyrene, poly (vinyl phosphonic acid), polyoxyethylene(10), deoxyribonucleic acid and ribonucleic acid.

In certain embodiments in the biocompatible composition of the present invention the amphiphile is selected from the group consisting of polyethylene oxide, sulfonated polystyrene and poly (vinyl phosphonic acid).

In certain embodiments in the biocompatible composition of the present invention the amphiphile is polyethylene oxide.

In various embodiments, the polymerization can be conducted electrochemically, e.g., the polymerization agent can be an electrode at an electrochemical potential that oxidatively polymerizes the flavanoid. Polymerization potentials with respect to the normal hydrogen electrode (NHE) can range from $-0.1V$ to $2.0V$, or more typically $-0.02V$ to $0.8$ V. In certain embodiments such polymerization will result in a deposition of the polymer on the electrode surface.

In various embodiments, the polymerization agent can be a catalyst or initiator whereby the polymerization can be conducted chemically. In various embodiments, the polymerization agent can be sodium persulfate, potassium persulfate, ammonium persulfate, ferric chloride, additional polymerization agents are hematin or hematin substituted with polyethylene glycol. "Pegylated" hematin has been used recently to polymerize anilines, phenols and styrenes as well as other monomers such as pyrroles, 3,4-ethylenedioxythiophene (EDOT) ("Biomimetic Synthesis of Water Soluble Conductive Polypyrrole and Poly (3,4 ethylenedioxythiophene)" Bruno, F. F., Nagarajan, R., Roy, S., Kumar, J., Samuelson, L. A., J. Macro. Sci., Pure and Appl. Chem. A40 (12), 1327-1333, 2003).

In various embodiments, the polymerization agent can be an enzyme whereby the polymerization can be conducted enzymatically. For example, in typical embodiments, the polymerization agent includes an oxido-reductase. Examples of oxido-reductases can include horseradish peroxidase (HRP) soybean peroxidase (SBP), lignin peroxidase (LiP), manganese peroxidase (MnP), laccases, or the like. In particular embodiments, the polymerization agent can be HRP in combination with hydrogen peroxide.

In certain embodiments the polymerization agent is a biocompatible polymerization agent selected from an oxido-reductase, hematin or modified hematin.

In certain embodiments the polymerization solubilizer is a material or combination of materials that help solubilize the monomers and polymeric products.

In certain embodiments the polymerization solubilizer is a material or combination of materials that help solubilizer the monomers and polymeric products.

In various embodiments, the biocompatible polymerization solubilizer can include a mixed solvent selected from water-ethanol, water-dimethyl sulfoxide, water-isopropyl alcohol, additional polymerization solubilizers include water-dimethyl formamide. In certain embodiments the biocompatible solubilizer is a mixed solvent selected from water-ethanol, water-dimethyl sulfoxide and water-isopropyl alcohol. In certain embodiments the biocompatible solubilizer is a mixed solvent selected from water-ethanol, and water-isopropyl alcohol. In certain embodiments the biocompatible solubilizer is a mixed solvent of water-ethanol. The mixed solvents can be in a ratio of water:organic solvent from about 1:99 to about 99:1, or in some embodiments, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5, or in particular embodiments, water:organic solvent in a ratio of about 90:10. In particular embodiments, the biocompatible polymerization solubilizer can be a water-ethanol mixture.

In various embodiments, the biocompatible polymerization solubilizer can include an amphiphile or a biocompatible organic amphiphile. As used herein, an amphiphile is a molecule including both an organic hydrophobic group and a hydrophilic group. Typical amphiphiles include organic electrolytes, polymeric electrolytes, surfactants, and the like. An amphiphile can be anionic or nonionic. Typically, the hydrophobic group is an optionally substituted aliphatic, aryl, heteroaryl, or non-aromatic heterocyclic group, or a combination thereof. Typically, the hydrophilic group can be a nonionic hydrophilic group (e.g., the oxygen atoms in polyethylene oxide) or can be a charged, typically anionic group, for example, a sulfate, a phosphate, a carboxylate, or the like. Many more examples of hydrophilic anionic groups include those anionic groups described as suitable optional substituents below. In some embodiments, the amphiphile can include or be substituted with optically active groups (e.g., chromophores, fluorophores, and the like), or in particular embodiments, the amphiphile can include or be substituted with electrically active groups. An amphiphile can also be optionally substituted as described further below in the section regarding optional substituents.

In various embodiments, the polymerization solubilizer includes an amphiphile that is a compound selected from polyethylene oxide, sulfonated polystyrene, poly (vinyl phosphonic acid) sodium dodecyl benzenesulfonate, polyoxyethylene(10), isooctylphenyl ether (Triton X-100), p-toluenesulphonic acid monohydrate, deoxyribonucleic acid, ribonucleic acid, 1-palmitoly-2-oleoyl-sn-glycerol-3-phosphate, sodium octylsulfonate, 1-palmitoly-2-oleoyl-sn-glycero-3-phosphocholine, and benzoyl-L-tyrosine-p-nitroanilde. In some embodiments, the polymerization solubilizer includes an amphiphile that is a compound selected from polyethylene oxide, sulfonated polystyrene, poly (vinyl phosphonic acid), and sodium dodecyl benzenesulfonate, or in some embodiments, polyoxyethylene(10), isooctylphenyl ether (Triton X-100), and p-toluenesulphonic acid monohydrate. In particular embodiments, the polymerization solubilizer is biocompatible and is selected from the group polyethylene oxide, sulfonated polystyrene, poly (vinyl phosphonic acid), polyoxyethylene(10), deoxyribonucleic acid and ribonucleic acid. In particular embodiments, the biocompatible polymerization solubilizer can be polyethylene oxide, sulfonated polystyrene or poly (vinyl phosphonic acid). In particular embodiments, the biocompatible polymerization solubilizer can be polyethylene oxide.

In certain embodiments the amphiphile is a template which helps in aligning the monomer through electrostatic interactions or hydrogen bonds, and in certain embodiments can produce water-soluble polymers.

Figure 3:
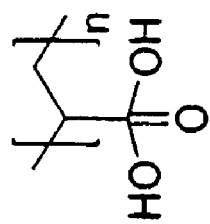
FIG. 3 depicts the chemical structures of some biocompatible polymerization solubilizers such as polyethylene oxide (PEO), sulfonated polystyrene (SPS), and poly(vinyl phosphonic acid) (PVPA).
Figure 3:
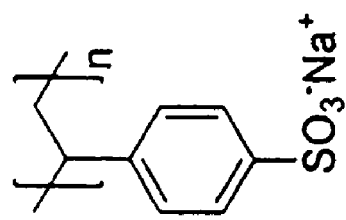
Figure 3:
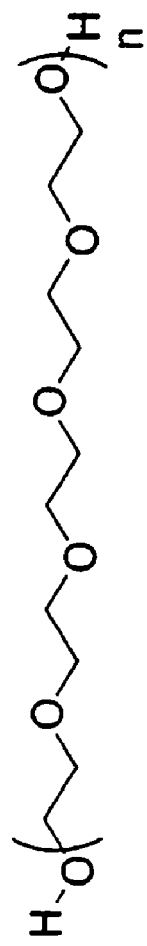

FIG. 3 depicts the chemical structures of some biocompatible polymerization solubilizers such as polyethylene oxide (PEO), sulfonated polystyrene (SPS), and poly(vinyl phosphonic acid) (PVPA).

In some embodiments, the biocompatible polymerization solubilizer consists essentially of a mixed solvent.

In some embodiments, the biocompatible polymerization solubilizer consists essentially of an amphiphile.

In various embodiments, the biocompatible polymerization solubilizer includes a mixed solvent and an amphiphile. In a preferred embodiment, the biocompatible polymerization solubilizer can be water-ethanol and polyethylene oxide.

In various preferred embodiments, the biocompatible polymerization solubilizer can be a water-ethanol mixture, and the polymerization agent can be HRP in combination with hydrogen peroxide. Typically, the flavanoid can be (−)-catechin or (+)-catechin, whereby the biocompatible, soluble oligo/polyflavanoid is oligo/poly(−)-catechin or oligo/poly (+)-catechin; or the flavanoid can be (−)-epicatechin or (+)-epicatechin, whereby the biocompatible, soluble oligo/polyflavanoid is oligo/poly(−)-epicatechin or oligo/poly(+)-epicatechin.

In some preferred embodiments, the biocompatible polymerization solubilizer can be polyethylene oxide, and the polymerization agent can be HRP in combination with hydrogen peroxide. Typically, the flavanoid can be (−)-catechin or (+)-catechin, whereby the biocompatible, soluble oligo/polyflavanoid is oligo/poly(−)-catechin or oligo/poly(+)-catechin; or the flavanoid can be (−)-epicatechin or (+)-epicatechin, whereby the biocompatible, soluble oligo/polyflavanoid is oligo/poly(−)-epicatechin or oligo/poly(+)-epicatechin.

In particular preferred embodiments, the biocompatible polymerization solubilizer can include both a water-ethanol mixture and polyethylene oxide, and the polymerization agent can be HRP in combination with hydrogen peroxide. Typically, the flavanoid can be (−)-catechin or (+)-catechin, whereby the biocompatible, soluble oligo/polyflavanoid is oligo/poly(−)-catechin or oligo/poly(+)-catechin; or the flavanoid can be (−)-epicatechin or (+)-epicatechin, whereby the biocompatible, soluble oligo/polyflavanoid is oligo/poly (−)-epicatechin or oligo/poly(+)-epicatechin.

In various embodiments, the flavanoid can be polymerized to form a complex comprising the oligo/polyflavanoid and an amphiphile.

In various embodiments, the flavanoid can be polymerized to form a complex comprising the biocompatible, water-soluble oligo/polyflavanoid and an organic amphiphile. Examples of complexes include oligo/polycatechin-polyethylene oxide, oligo/polycatechin-sulfonated polystyrene, oligo/polycatechin-DBSA, or the like. In a particular embodiment, the complex is oligo/polycatechin-polyethylene oxide.

In certain embodiments the present invention is method for synthesizing a polymer comprising polymerizing an optionally substituted flavanoid, phenolic acid, hydroxycinnamic acid or phytochemical with a polymerization agent in the presence of a biocompatible polymerization solubilizer. Wherein the oligo/polyflavanoid, the polymerization agent and the polymerization solubilizer are as described herein.

In certain embodiments of the present invention the phenolic acid is selected from the group consisting of gallic, Capsaicin, Ellagic, Rosmarinic and tannic acids, the phytochemical is selected from the group consisting of Damnacanthal, Digoxin and phytic acids and the hydroxycinnamic acid is selected from the group consisting of Chicoric acid, Coumarin, Scopoletin and Ferulic acid.

In certain embodiments of the present invention an optionally substituted flavanoid is polymerized to form an oligo/polyflavanoid. In certain embodiments of the present invention the flavanoid is selected from the group consisting of optionally substituted catechin, quercitin, flavonone, isoflavone, chalcone, anthocyanidin, chrysin, primuletin, fisetin, naringin, hesperidin, prunin, daidzein, genistein, pelargonidin, cyanidin, delphinidin, phenolic acid, phytochemical and hydroxycinnamic acid. In certain embodiments of the present invention the oligo/polyflavanoid is selected from oligo/poly(−)-catechin, oligo/poly(−)-epicatechin, oligo/poly(−)-gallocatechin, oligo/poly(−)-catechin gallate, oligo/poly(−)-epigallocatechin, oligo/poly(−)-gallocatechin gallate, oligo/poly(−)-epicatechin gallate, oligo/poly(−)-epigallocatechin gallate, oligo/poly(+)-catechin, oligo/poly(+)-epicatechin, oligo/poly(+)-gallocatechin, oligo/poly(+)-catechin gallate, oligo/poly(+)-epigallocatechin, oligo/poly(+)-gallocatechin gallate, oligo/poly(+)-epicatechin gallate, and oligo/poly(+)-epigallocatechin gallate. Wherein the oligo/polyflavanoid, the polymerization agent and the polymerization solubilizer are as described herein.

In certain embodiments the present invention is a method for synthesizing a oligo/polyflavanoid comprising polymerizing a flavanoid with a polymerization agent in the presence of an amphiphile. Wherein the oligo/polyflavanoid, the polymerization agent and the polymerization solubilizer are as described herein.

In certain embodiment the present invention is a method for synthesizing a water-soluble oligo/polyflavanoid having a UV-visible spectrum including a peak between 350 and 450 nm comprising polymerizing a flavanoid with a polymerization agent in the presence of a polymerization solubilizer.

In certain embodiments the present invention is a method of synthesizing a biocompatible, water-soluble oligo/polyflavanoid, comprising polymerizing an optionally substituted flavanoids with a polymerization agent in the presence of a biocompatible polymerization solubilizer, thereby producing the biocompatible, soluble oligo/polyflavanoid. Wherein the oligo/polyflavanoid, the polymerization agent and the polymerization solubilizer are as described herein.

In certain embodiments in the methods of the present invention the polymerization agent is a biocompatible catalyst. In certain embodiments in the methods of the present invention the catalyst is an oxido-reductase, hematin or hematin substituted with polyethylene glycol. In certain embodiments in the methods of the present invention the catalyst is horseradish peroxidase (HRP) soybean peroxidase (SBP), lignin peroxidase (LiP), manganese peroxidase (MnP), or a laccase.

In certain embodiments in the methods of the present invention the polymerization agent is HRP in combination with hydrogen peroxide. In certain embodiments in the methods of the present invention the polymerization agent is hematin in combination with hydrogen peroxide.

In certain embodiments in the methods of the present invention the polymerization agent is an electrode at an electrochemical potential that oxidatively polymerizes the flavanoid. In certain embodiments in the methods of the present invention the polymerization agent is sodium persulfate, potassium persulfate, ammonium persulfate, or ferric chloride.

In certain embodiments in the methods of the present invention the biocompatible polymerization solubilizer comprises a mixed solvent selected from water-ethanol, water-dimethyl sulfoxide and water-isopropyl alcohol. In certain embodiments in the methods of the present invention the biocompatible polymerization solubilizer is a water-ethanol mixture or a water-isopropyl alcohol mixture. In certain embodiments in the methods of the present invention the biocompatible polymerization solubilizer is a water-ethanol mixture. In certain embodiments in the methods of the present invention the biocompatible polymerization solubilizer is a water-ethanol mixture and the polymerization agent is HRP in combination with hydrogen peroxide.

In certain embodiments in the methods of the present invention the biocompatible polymerization solubilizer is a biocompatible organic amphiphile. In certain embodiments in the methods of the present invention the biocompatible polymerization solubilizer is a compound selected from the group consisting of polyethylene oxide, sulfonated polystyrene, poly (vinyl phosphonic acid), polyoxyethylene(10), deoxyribonucleic acid and ribonucleic acid. In certain embodiments in the methods of the present invention the biocompatible polymerization solubilizer is polyethylene oxide, sulfonated polystyrene or poly (vinyl phosphonic acid). In certain embodiments in the methods of the present invention the biocompatible polymerization solubilizer is polyethylene oxide. In certain embodiments in the methods of the present invention the biocompatible polymerization solubilizer is polyethylene oxide and a mixed solvent selected from water-ethanol, water-dimethyl sulfuoxide, and water-isopropyl alcohol. In certain embodiments in the methods of the present invention the biocompatible polymerization solubilizer is water-ethanol and polyethylene oxide.

In certain embodiments in the methods of the present invention the biocompatible polymerization solubilizer is water-ethanol and polyethylene oxide and the biocompatible polymerization solubilizer is polyethylene oxide. the polymerization agent is HRP in combination with hydrogen peroxide.

In certain embodiments in the methods of the present invention the biocompatible polymerization solubilizer is water-ethanol and polyethylene oxide and the polymerization agent is hematin in combination with hydrogen peroxide.

In certain embodiments in the methods of the present invention flavanoid is polymerized to form a complex comprising the oligo/polyflavanoid and a biocompatible organic amphiphile. In certain embodiments in the methods of the present invention the complex is oligo/polycatechin-polyethylene oxide.

In certain embodiments the oligo/polyflavanoids produced by the methods of the present invention have a UV-visible spectrum including a peak between 350 and 450 nm.

In certain embodiments the oligo/polyflavanoids produced by the methods of the present invention have a solubility in 1 mL of water of between 0.5 and 5 mg at room temperature.

In certain embodiments the oligo/polyflavanoids produced by the methods of the present invention have a solubility in 1 mL of water of between 1 and 3 mg at room temperature.

In certain embodiments the oligo/polyflavanoids produced by the methods of the present invention have an average molecular weight of between 3,000 and 50,000 Daltons.

In certain embodiments the oligo/polyflavanoids produced by the methods of the present invention have an average molecular weight of between 10,000 and 50,000 Daltons.

In certain embodiment the polymerization reactions of the present invention are carried out in a "one-step" reaction.

In certain embodiment the polymerization reactions of the present invention are carried out at between 20 and 37° C.

In certain embodiments the present invention is a method for synthesizing a oligo/polyflavanoid comprising polymerizing a flavanoid with a polymerization agent in the presence of an amphiphile. In certain embodiments the amphiphile is selected from polyethylene oxide, sulfonated polystyrene, poly (vinyl phosphonic acid), sodium dodecyl benzenesulfonate, polyoxyethylene(10), isoctylphenyl ether, p-toleunesulphonic acidmonohydrate, deoxyribonucleic acid, ribonucleic acid, 1-palmitoly-2-oleoyl-sn-glycerol-3-phosphate, sodium octylsulfonate, 1-palmitoly-2-oleoyl-sn-glycero-3-phosphocholine, and benzoyl-L-tyrosine-p-nitroanilde. In certain embodiments the amphiphile is a biocompatible organic amphiphile. In certain embodiments the amphiphile is a compound selected from the group consisting of polyethylene oxide, sulfonated polystyrene, poly (vinyl phosphonic acid), polyoxyethylene(10), deoxyribonucleic acid and ribonucleic acid. In certain embodiments the amphiphile is polyethylene oxide, sulfonated polystyrene or poly (vinyl phosphonic acid). In certain embodiments the amphiphile is polyethylene oxide. In certain embodiments this method is carried out in a mixed solvent selected from water-ethanol, water-dimethyl sulfuoxide, and water-isopropyl alcohol. In certain embodiments in this method the mixed solvent is water-ethanol and the amphiphile is polyethylene oxide. In certain embodiments in this method the reaction is carried out in the presence of a polymerization agent as described above.

In certain embodiments the present invention is a method for synthesizing a water-soluble oligo/polyflavanoid having a UV-visible spectrum including a peak between 350 and 450 nm comprising polymerizing a flavanoid with a polymerization agent in the presence of a polymerization solubilizer. The polymerization agents and polymerization solubilizer are as described above. In certain embodiments the oligo/polyflavanoids produced by the methods of the present invention have a solubility in 1 mL of water of between 0.5 and 5 mg at room temperature. In certain embodiments the oligo/polyflavanoids produced by the methods of the present invention have a solubility in 1 mL of water of between 1 and 3 mg at room temperature.

In certain embodiment the present invention is a method of synthesizing a polymer comprising at least two repeat units independently selected from the group consisting of:

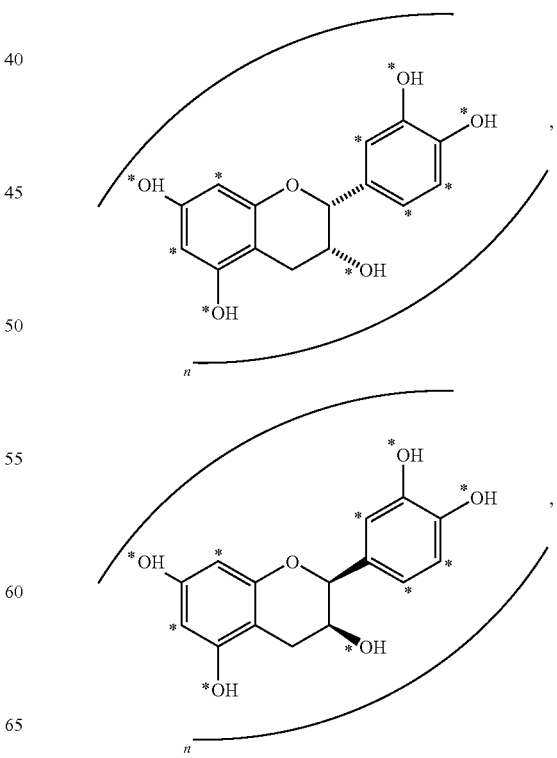

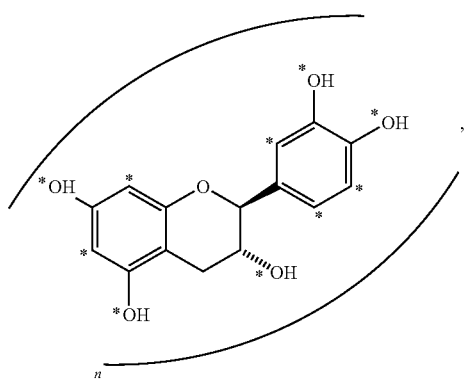

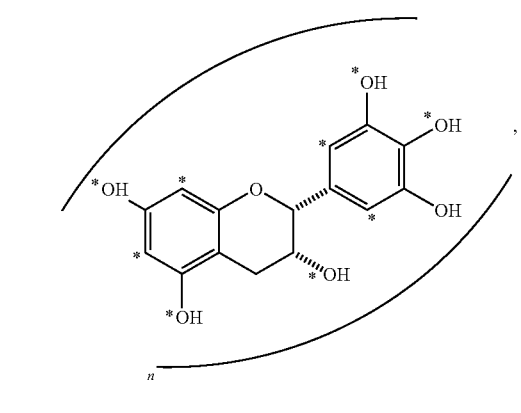

and

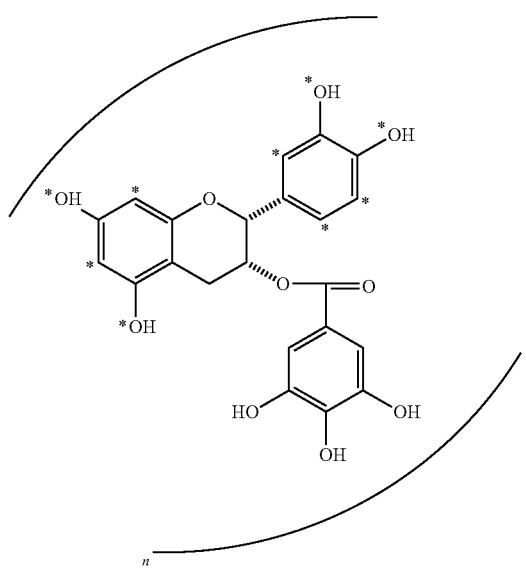

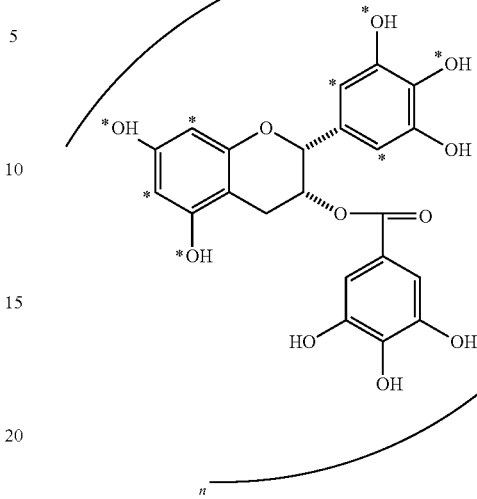

or a pharmaceutically acceptable salt thereof. Each repeat unit is independently optionally substituted with one or more substituents, and between one and four —H atoms in each repeat unit attached to the oxygen or carbon at each * are independently replaced by a polymer link. Each n is independently an integer from 0 to 170 inclusive, wherein the sum of all ns is an integer from 2 to 170 inclusive. The method comprises polymerizing the repeat unit with a polymerization agent in the presence of a polymerization solubilizer. The polymerization agents and polymerization solubilizer are as described above.

In various embodiments the present invention is a method for synthesizing a biocompatible, water-soluble oligo/polyflavanoid, includes polymerizing an optionally substituted flavanoid with a polymerization agent in the presence of a biocompatible polymerization solubilizer, thereby producing the biocompatible, soluble oligo/polyflavanoid.

In various embodiments, the invention is a biocompatible, soluble oligo/polyflavanoid or a pharmaceutically acceptable salt, solvate, or complex thereof, wherein the oligo/polyflavanoid is as described herein.

Various embodiments include a complex comprising a biocompatible, soluble, oligo/polyflavanoid or a pharmaceutically acceptable salt, or solvate complex and a biocompatible amphiphile. For example, a complex can include oligo/poly (−)-catechin, oligo/poly(+)-catechin, oligo/poly(−)-epicatechin, oligo/poly(+)-epicatechin, or the like complexed with polyethylene oxide or another biocompatible amphiphile.

In certain embodiments the present invention is a method of synthesizing oligo/polyflavanoids. In certain embodiments the methods use a biocompatible polymerization solubilizer. In certain embodiments a biocompatible solubilizer does not include non-biocompatible solvents, such as, for example, methanol (J. Org Chem, 2003, 68 1641-1658 and Biomacromolecules Vol 4, No. 3 2003, the entire contents of each of which are incorporated herein by reference). In certain embodiments the oligo/polyflavanoids produced by the methods of the present invention are soluble in water. In certain embodiments the flavanoid use to make the oligo/polyflavanoid is not (+)catechin. In certain embodiments the methods of the present invention are "one-step" reactions which are conducted at room temperature (20-37° C.) and ambient pressure. In certain embodiments the oligo/polyflavanoids produced by the methods of the present invention have an average molecular weight of between 1,000 and 100,000 Dalton, between 3,000 and 50,000 Dalton between 10,000 and 50,000 Dalton.

As used herein an average molecular weight is the total weight of all the polymer molecules in a sample divided by the total number of polymer molecules in a sample. Average molecular weigh is typically measured by Gel Permeation Chromatography (GPC).

In certain embodiments of the present invention the polymer produced by the methods described herein are linked C—C bonds or C—O—C bond. In certain embodiments the C—C bonds are typically between aromatic carbon atoms. In certain embodiments the oligo/polyflavanoids of the present invention have UV spectra which include peaks between 300 and 500 nm, typically between 350 and 450 nm.

As used herein "a polymer link" is a bond between two monomer units.

In certain embodiments hydrogen peroxide is used to initiate the reactions of the present invention. In certain embodiments the concentrations of hydrogen peroxide used to initiate the reaction can be in the range of 0.03% to 30%

In certain embodiments the amount of horseradish peroxidase used for the catalysis can be in the range of 0.1 mg to 4 mg.

Various embodiments include a complex comprising a biocompatible, soluble, oligo/polyflavanoid or a pharmaceutically acceptable salt, or solvate complex and a biocompatible amphiphile. For example, a complex can include oligo/poly(−)-catechin, oligo/poly(+)-catechin, oligo/poly(−)-epicatechin, oligo/poly(+)-epicatechin, or the like complexed with polyethylene oxide or another biocompatible amphiphile.

In some embodiments, a majority of the flavanoid repeat units of the chiral oligo/polyflavanoid are the same flavanoid enantiomer, whereby the oligo/polyflavanoid is chiral. In typical embodiments, substantially all the flavanoid repeat units are the same flavanoid enantiomer, or in particular embodiments, all the flavanoid repeat units of the oligo/polyflavanoid are the same flavanoid enantiomer.

As used herein, an aliphatic group is a straight chained, branched or cyclic non-aromatic hydrocarbon which is completely saturated or which contains one or more units of unsaturation. An alkyl group is a saturated aliphatic group. Typically, a straight chained or branched aliphatic group has from 1 to about 10 carbon atoms, preferably from 1 to about 4, and a cyclic aliphatic group has from 3 to about 10 carbon atoms, preferably from 3 to about 8. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. C1-C4 straight chained or branched alkyl or alkoxy groups or a C3-C8 cyclic alkyl or alkoxy group (preferably C1-C4 straight chained or branched alkyl or alkoxy group) are also referred to as a "lower alkyl" or "lower alkoxy" groups; such groups substituted with —F, —Cl, —Br, or —I are "lower haloalkyl" or "lower haloalkoxy" groups; a "lower hydroxyalkyl" is a lower alkyl substituted with —OH; and the like.

As used herein, an alkylene group is a linking alkyl chain represented by —(CH$_2$)$_n$—, wherein n is an integer from 1-10, preferably 1-4.

As used herein, the term "aryl" refers to C6-C14 carbocyclic aromatic groups such as phenyl, biphenyl, and the like. Aryl groups also include fused polycyclic aromatic ring systems in which a carbocyclic aromatic ring is fused to other aryl, cycloalkyl, or cycloaliphatic rings, such as naphthyl, pyrenyl, anthracyl, and the like.

As used herein, the term "heteroaryl" refers to 5-14 membered heteroaryl groups having 1 or more O, S, or N heteroatoms. Examples of heteroaryl groups include imidazolyl, isoimidazolyl, thienyl, furanyl, fluorenyl, pyridyl, pyrimidyl, pyranyl, pyrazolyl, pyrrolyl, pyrazinyl, thiazoyl, isothiazolyl, oxazolyl, isooxazolyl, 1,2,3-trizaolyl, 1,2,4-triazolyl, imidazolyl, thienyl, pyrimidinyl, quinazolinyl, indolyl, tetrazolyl, and the like. Heteroaryl groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazolyl, benzoisothiazolyl, benzooxazolyl, benzoisooxazolyl, benzimidazolyl, quinolinyl, isoquinolinyl and isoindolyl.

As used herein, a non-aromatic heterocyclic group includes non-aromatic carbocyclic rings which include one or more heteroatoms such as N, O, or S in the ring. The ring can be five, six, seven or eight-membered. Examples include oxazolinyl, thiazolinyl, oxazolidinyl, thiazolidinyl, tetrahydrofuranyl, tetrahydrothiophenyl, morpholino, thiomorpholino, pyrrolidinyl, piperazinyl, piperidinyl, thiazolidinyl, and the like.

As used herein, "optionally substituted" means that a compound is substituted or unsubstituted. Suitable optional substituents for a substitutable atom in alkyl, cycloalkyl, aliphatic, cycloaliphatic, heterocyclic, benzylic, aryl, or heteroaryl groups are those substituents that do not substantially interfere with the pharmaceutical activity of the oligo/polyflavanoids. A "substitutable atom" is an atom that has one or more valences or charges available to form one or more corresponding covalent or ionic bonds with a substituent. For example, a carbon atom with one valence available (e.g., —C(—H)=) can form a single bond to an alkyl group (e.g., —C(-alkyl)=), a carbon atom with two valences available (e.g., —C(H$_2$)—) can form one or two single bonds to one or two substituents (e.g., —C(alkyl)(H)—, —C(alkyl)(Br)—,) or a double bond to one substituent (e.g., —C(=O)—), and the like. Substitutions contemplated herein include only those substitutions that form stable compounds.

For example, suitable optional substituents for substitutable carbon atoms include —F, —Cl, —Br, —I, —CN, —NO$_2$, —OR$^a$, —C(O)R$^a$, —OC(O)R$^a$, —C(O)OR$^a$, —SR$^a$, —C(S)R$^a$, —OC(S)R$^a$, —C(S)OR$^a$, —C(O)SR$^a$, —C(S)SR$^a$, —S(O)R$^a$, —SO$_2$R$^a$, —SO$_3$R$^a$, —PO$_2$R$^a$R$^b$, —PO$_3$R$^a$R$^b$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), —C(NR$^c$)—N(R$^a$R$^b$), —NR$^d$—C(NR$^c$)—N(R$^a$R$^b$), —NR$^a$N(R$^a$R$^b$), —CR$^c$=CR$^a$R$^b$, —C≡CR$^a$, =O, =S, =CR$^a$R$^b$, =NR$^a$, =NOR$^a$, =NNR$^a$, optionally substituted alkyl, optionally substituted cycloalkyl, optionally substituted aliphatic, optionally substituted cycloaliphatic, optionally substituted heterocyclic, optionally substituted benzyl, optionally substituted aryl, and optionally substituted heteroaryl, wherein R$^a$-R$^d$ are each independently —H or an optionally substituted aliphatic, optionally substituted cycloaliphatic, optionally substituted heterocyclic, optionally substituted benzyl, optionally substituted aryl, or optionally substituted heteroaryl, or, —N(R$^a$R$^b$), taken together, is an optionally substituted heterocyclic group.

Suitable substituents for nitrogen atoms having two covalent bonds to other atoms include, for example, optionally substituted alkyl, optionally substituted cycloalkyl, optionally substituted aliphatic, optionally substituted cycloaliphatic, optionally substituted heterocyclic, optionally substituted benzyl, optionally substituted aryl, optionally substituted heteroaryl, —CN, —NO$_2$, —OR$^a$, —C(O)R$^a$, —OC(O)R$^a$, —C(O)OR$^a$, —SR$^a$, —S(O)R$^a$, —SO$_2$R$^a$, —SO$_3$R$^a$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), and the like.

A nitrogen-containing heteroaryl or non-aromatic heterocycle can be substituted with oxygen to form an N-oxide, e.g., as in a pyridyl N-oxide, piperidyl N-oxide, and the like. For example, in various embodiments, a ring nitrogen atom in a nitrogen-containing heterocyclic or heteroaryl group can be substituted to form an N-oxide.

Suitable substituents for nitrogen atoms having three covalent bonds to other atoms include —OH, alkyl, and alkoxy (preferably C1-C4 alkyl and alkoxy). Substituted ring nitrogen atoms that have three covalent bonds to other ring atoms are positively charged, which is balanced by counteranions such as chloride, bromide, fluoride, iodide, formate, acetate and the like. Examples of other suitable counteranions are provided in the section below directed to suitable pharmacologically acceptable salts.

As used herein, the term "biocompatible" means that the materials (e.g., compositions, carriers, diluents, complexes, reagents, salts, and the like) are capable of administration to or upon a subject, e.g., a mammal, with physiological side effects that can be tolerated such as nausea, dizziness or gastric upset, but no intolerable side effects, for example, poisoning and blindness associated with methanol ingestion in humans. The dosage and exposure for determining the physiological side effects are any toxicity test which are known in the art.

As used herein, the term "pharmaceutically acceptable" means that the materials (e.g., compositions, carriers, diluents, reagents, complexes, salts, and the like) are capable of administration to or upon a mammal with a minimum of undesirable physiological effects such as nausea, dizziness or gastric upset.

As used herein, the term "soluble" means that in various embodiments all of a sample can be dissolved into a biocompatible solvent such as water or a water-ethanol mixture or petroleum jelly at a temperature between about 20° C. and about 37° C. (ambient and physiological temperature). In some embodiments, essentially all of a soluble sample dissolves into the biocompatible solvent or solvent mixture between about 20° C. and about 37° C. In some embodiments, essentially all of a soluble sample dissolves into the biocompatible solvent at about 20° C. As used herein the term "water-soluble" means that between 0.01-20 mg of solid dissolves in 1 mL of water under ambient conditions at a temperature between about 20° C. and about 37° C., or between 0.1 and 10 mg, between 0.5 and 5 mg, or between 1 and 3 mg. In certain embodiments the sample is not-soluble in solvents, such as, water or water-ethanol mixtures, in certain embodiment the sample forms a colloidal suspension or emulsion in solvents such as water or water-ethanol.

Also included in the present invention are pharmaceutically acceptable salts of the oligo/polyflavanoids. These oligo/polyflavanoids can have one or more sufficiently acidic protons that can react with a suitable organic or inorganic base to form a base addition salt. When it is stated that a compound has a hydrogen atom bonded to an oxygen, nitrogen, or sulfur atom, it is contemplated that the compound also includes salts thereof where this hydrogen atom has been reacted with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like.

For example, pharmaceutically acceptable salts of the oligo/polyflavanoids can include those formed by the reaction of the oligo/polyflavanoids with one equivalent of a suitable base to form a monovalent salt (i.e., the compound has single negative charge that is balanced by a pharmaceutically acceptable counter cation, e.g., a monovalent cation) or with two equivalents of a suitable base to form a divalent salt (e.g., the compound has a two-electron negative charge that is balanced by two pharmaceutically acceptable counter cations, e.g., two pharmaceutically acceptable monovalent cations or a single pharmaceutically acceptable divalent cation). "Pharmaceutically acceptable" means that the cation is suitable for administration to a subject. Examples include Li$^+$, Na$^+$, K$^+$, Mg$^{2+}$, Ca$^{2+}$ and NR$_4^+$, wherein each R is independently hydrogen, an optionally substituted aliphatic group (e.g., a hydroxyalkyl group, aminoalkyl group or ammoniumalkyl group) or optionally substituted aryl group, or two R groups, taken together, form an optionally substituted non-aromatic heterocyclic ring optionally fused to an aromatic ring. Generally, the pharmaceutically acceptable cation is Li$^+$, Na$^+$, K$^+$, NH$_3$(C$_2$H$_5$OH)$^+$ or N(CH$_3$)$_3$(C$_2$H$_5$OH)$^+$.

Pharmaceutically acceptable salts of the oligo/polyflavanoids with a sufficiently basic group, such as an amine, can be formed by reaction of the oligo/polyflavanoids with an organic or inorganic acid to form an acid addition salt. Acids commonly employed to form acid addition salts from compounds with basic groups can include inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

It will also be understood that certain oligo/polyflavanoids can be obtained as different stereoisomers (e.g., diastereomers and enantiomers) and that the invention includes all isomeric forms and racemic mixtures of the disclosed compounds and methods of treating a subject with both pure isomers and mixtures thereof, including racemic mixtures. Stereoisomers can be separated and isolated using any suitable method, such as chromatography.

In certain embodiments the present invention is a method of treating a condition described herein in a subject in need thereof comprising administering to the subject a polymer (such as an oligo/polyflavanoid) or a biocompatible composition as described herein.

As used herein, a "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

In various embodiments, a subject can be obese, whereby the subject can be treated therapeutically. In some embodiments, the subject can be at risk of obesity, whereby the subject can be treated prophylactically. As used herein, "treating a subject with obesity," or similar terms, includes achieving, partially or substantially, one or more of the following: weight reduction, weight control, or improving a clinical symptom or indicator associated with obesity, for example, type 2 diabetes, hypertension, congestive heart failure, arteriosclerosis, or the like.

In various embodiments, a subject can have cancer, whereby the subject can be treated therapeutically. In some embodiments, the subject can be at risk of cancer, whereby the subject can be treated prophylactically. As used herein, "treating a subject with a cancer," or similar terms, includes achieving, partially or substantially, one or more of the following: arresting the growth or spread of a cancer, reducing the extent of a cancer (e.g., reducing size of a tumor or reducing the number of affected sites), inhibiting the growth rate of a cancer, and ameliorating or improving a clinical symptom or indicator associated with a cancer (such as tissue or serum components).

In various embodiments, cancer can include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

In some embodiments, cancer can include colon cancer, pancreatic cancer, melanoma, renal cancer, sarcoma, breast cancer, ovarian cancer, lung cancer. stomach cancer, bladder cancer and cervical cancer.

In some embodiments, the cancer can be breast cancer. In particular embodiments, the cancer can be colon cancer.

In some embodiments the cancer can be head, neck esophageal, tongue or pharyngeal cancer.

In various embodiments, a subject can be treated for cardiac damage. The cardiac damage can be caused by cardiac ischemia, e.g., associated with myocardial infarction; or inflammation, fibrosis, or cell infiltration of cardiac tissue; or immune rejection of cardiac tissue, e.g., cardiac damage to cardiac tissue transplanted into the subject as in allograft rejection. As used herein, "treating a subject with cardiac damage," or similar terms, includes achieving, partially or substantially, one or more of the following: arresting the progress of cardiac damage, reducing the extent of cardiac damage, reversing cardiac damage or suppressing cardiac damage so that natural healing processes may reverse cardiac damage, and ameliorating or improving a clinical symptom or indicator associated with cardiac damage. As used herein, "cardiac damage" includes effects on cardiac tissue such as scar tissue formation, cell death, immune rejection, cardiac muscle death, transplanted tissue rejection, or the like.

In various embodiments, a subject can be treated for a viral infection. Examples of viruses which can cause such infections include Picornavirus; Parvoviridae; Hepatitis virus; Papovavirus; Adenovirus; Herpesvirus, Poxvirus; Calicivirus; Arbovirus; Coronavirus; a Retrovirus; Rhabdovirus; Paramyxovirus; Orthomyxovirus; Arenavirus; human T-cell Lymphotrophic virus; human papillomavirus; and human immunodeficiency virus. In some embodiments, the viral infection can be caused by a virus selected from human immunodeficiency virus-1, human immunodeficiency virus-2, Cytomegalovirus, Epstein Barr Virus, Roseola Infantum, Varicella Zoster Virus, Herpes Zoster, Herpes Simplex Virus, and hepatitis virus. In particular embodiments, the viral infection can be caused by a virus selected from human immunodeficiency virus-1 and human immunodeficiency virus-2.

The oligo/polyflavanoids employed herein can be administered to a subject by any conventional method of drug administration, for example, orally in capsules, suspensions or tablets or by parenteral administration, or subcutaneously by topical administration. Parenteral administration can include, for example, systemic administration, such as by intramuscular, intravenous, subcutaneous, or intraperitoneal injection. In specific embodiments, oral, parenteral, or local administration are preferred modes of administration for treatment of cancer. Preferably, the mode of administration is intravenous.

A therapeutically effective amount of a oligo/polyflavanoid is a quantity in which a therapeutic effect can normally be achieved. The compounds of the method can be co-administered to the subject as a monotherapy, or as a combined therapy with other compounds, e.g., other anticancer compounds, either as part of the same pharmaceutical composition or, alternatively, as separate pharmaceutical compositions. When administered as separate pharmaceutical compositions, the different agents can be administered simultaneously or at different times.

The oligo/polyflavanoids employed herein can be administered to the subject in conjunction with an acceptable pharmaceutical carrier or diluent as part of a pharmaceutical composition for therapy. Formulation of the compound to be administered will vary according to the route of administration selected (e.g., solution, emulsion, capsule, and the like). Suitable pharmaceutically acceptable carriers may contain inert ingredients which do not unduly inhibit the biological activity of the compounds. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

EXEMPLIFICATION

Examples 1-7

Synthesis and Properties

A typical reaction for synthesizing a biocompatible, water-soluble oligo/polyflavanoid occurs in a solvent (e.g., aqueous media), typically buffered (e.g., at about pH 7) with typically only the flavanoid monomer (e.g., catechin), the biocompatible polymerization solubilizer (e.g., polyethylene oxide (PEO) and/or water-ethanol) and the polymerization agent (e.g., a catalytic amount of a peroxidase enzyme such as horseradish peroxidase (HRP) and hydrogen peroxide:

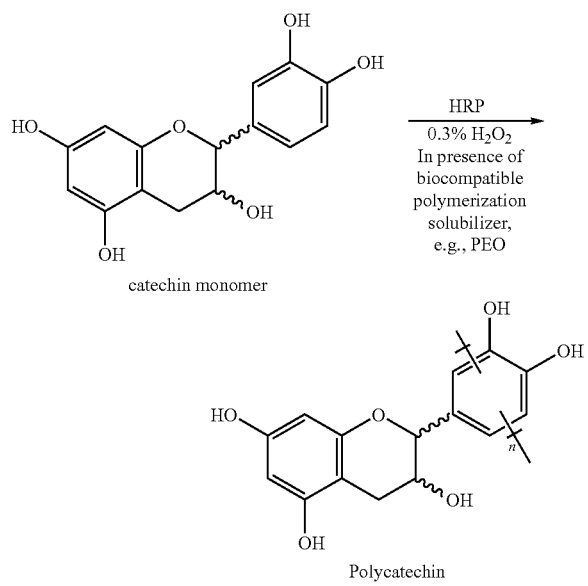

catechin monomer

Polycatechin

These reactions can typically be carried out as one-step, one pot reactions. The non-toxic nature of the process and aqueous solubility of the oligo/polycatechins facilitates ease of deliverability of these materials into biological systems. The use of a biocompatible polymerization solubilizer as a template also can allow one to tailor the nature of coupling of the monomers to obtain the desired products. Examples of polyelectrolyte templates as polymerization solubilizers in enzymatic synthesis of electrically conducting polymers has been studied extensively ("The Role of Template in the Enzymatic Synthesis of Conducting Polyaniline" W. Liu, A. L. Cholli, R. Nagarajan, J. Kumar, S. K. Tripathy, F. F. Bruno and L. Samuelson, J. Am. Chem. Soc. 121, 11345-11355, 1999. (b) "Enzymatically synthesized conducting polyaniline" W. Liu, J. Kumar, S. Tripathy, K. J. Senecal and L. Samuelson; J. Am. Chem. Soc., 121, 71, 1999). The polymerization solubilizers can help in improving the solubility and processability of the final polymer.

The product oligo/polyflavanoids can be characterized by $^1$H and $^{13}$C nuclear magnetic resonance (NMR), Fourier transform infrared spectroscopy (FT-IR), ultraviolet-visible spectroscopy, gel permeation chromatography, and other typical characterization techniques The presence of chiral centers in these flavonoids can indicate that the oligo/polyflavonoids obtained from them can exhibit interesting conformations/macro-asymmetry. Circular dichroism polarimetry can be used to study the stereochemical properties and secondary structure of the polymers. Initial studies indicated that these water-soluble catechins adopt a unique chirality/macro-asymmetry on polymerization. Further studies will help understand the chemical structure and achieve the distinctive configuration/conformation that can result in enhanced therapeutic/anti-oxidant/anti-cancer activity.

In certain embodiments it is likely that polymer links can be formed through any available aromatic ring carbon atom to form C—C bonds or through the hydroxy groups C—O—C as indicated throughout the specification.

Example 1

Biocompatible, Water-Soluble Oligo/Poly(+)-Catechin Synthesized in Presence of PEO A biocompatible polymerization solubilizer (13.41 μl of PEO) was dissolved in deionized water (10 mL) containing (+)-catechin (3.44 mM) at pH 7.0. This was followed by the addition of 4 mg of HRP as polymerization agent to this solution. The polymerization was initiated by the addition of 1021 μl of 0.3% hydrogen peroxide.

Example 2

Biocompatible, Water-Soluble Oligo/Poly(−)-Epicatechin Synthesized in Presence of PEO Polymerization of (−)-epicatechin in the presence of PEO catalyzed by HRP using hydrogen peroxide under ambient conditions. 13.41 μl of PEO was dissolved in deionized water (10 mL) at pH 7.0 for the polymerization of catechins. This was followed by the addition of 4 mg of HRP to this solution. The polymerization was initiated by the addition of 1021 μl of 0.3% hydrogen peroxide.

Figure 4:
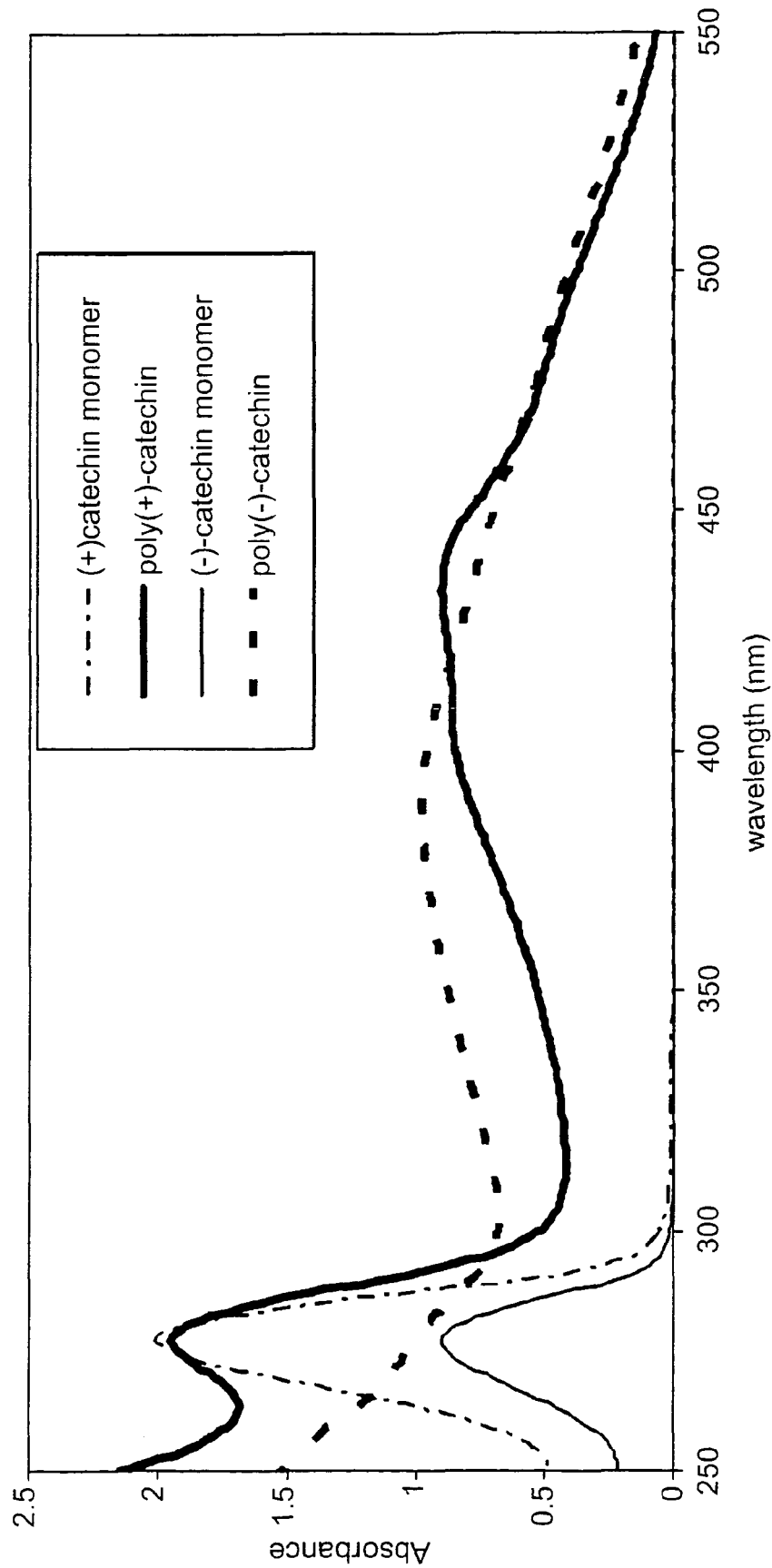
FIG. 4 is an ultra violet-visible (UV-Vis) absorption spectrum of Oligo/poly [(−) and (+)-catechin)]/PEO complex synthesized at pH 7 using HRP as a catalyst

FIG. 4 is an ultra violet-visible (UV-Vis) absorption spectrum of Oligo/poly [(−) and (+)-catechin)]/PEO complex synthesized at pH 7 using HRP as a catalyst Example 3

Biocompatible, Water-Soluble Oligo/Poly(−)-Catechin Synthesized in Presence of Ethanol:Water Polymerization of (−)-catechin in the presence of water-ethanol mixtures catalyzed by HRP using hydrogen peroxide under ambient conditions. 500 μl of ethanol was dissolved in deionized water (10 mL) at pH 7.0 for the polymerization of catechins (3.44 mM). 13.41 μl of PEO was dissolved in deionized water (10 mL) at pH 7.0 for the polymerization of catechins. This was followed by the addition of 4 mg of HRP to this solution. The polymerization was initiated by the addition of 1021 μl of 0.3% hydrogen peroxide.

Figure 5:
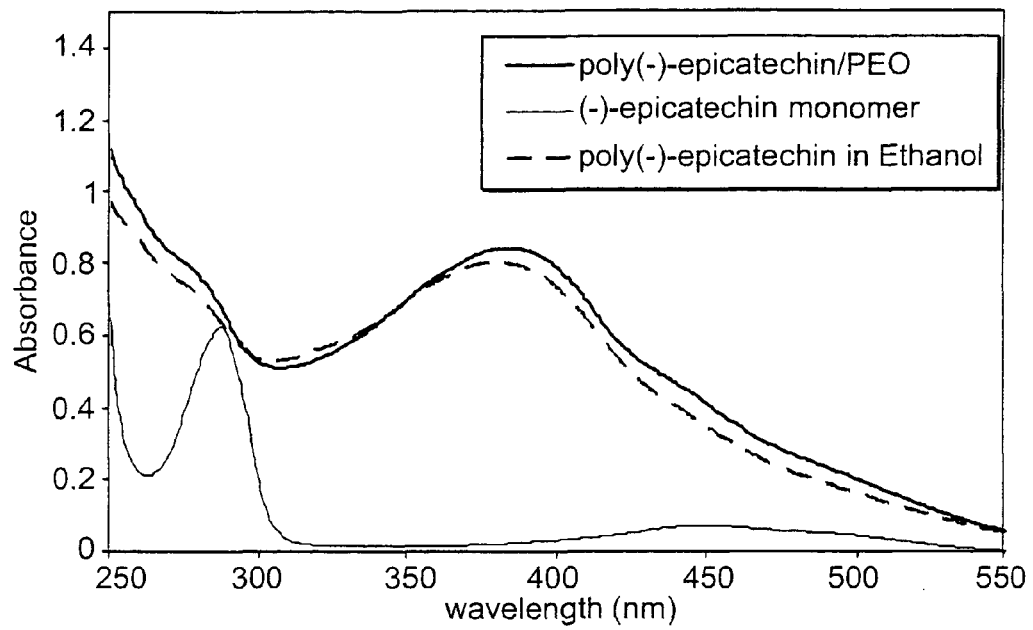
FIG. 5 is a UV-Vis absorption spectrum of oligo/poly(−) epicatechin using different biocompatible polymerization solubilizers.

FIG. 5 is a UV-Vis absorption spectrum of oligo/poly(−) epicatechin using different biocompatible polymerization solubilizers (ethanol:water or PEO)

Example 4

Biocompatible, Water-Soluble Oligo/Poly(−)-Epicatechin Synthesized in Presence of Organic Amphiphiles Polymerization of (−)-epicatechin in the presence of surfactants (organic amphiphiles DBSA, Triton X-100 and PTSA) catalyzed by HRP using hydrogen peroxide under ambient conditions. (−)-epicatechin (3.44 mM) and 4.3 mg of DBSA was dissolved in deionized water (10 mL) at pH 7.0. This was followed by the addition of 4 mg of HRP to this solution. The polymerization was initiated by the addition of 1021 µl of 0.3% hydrogen peroxide.

Figure 6:
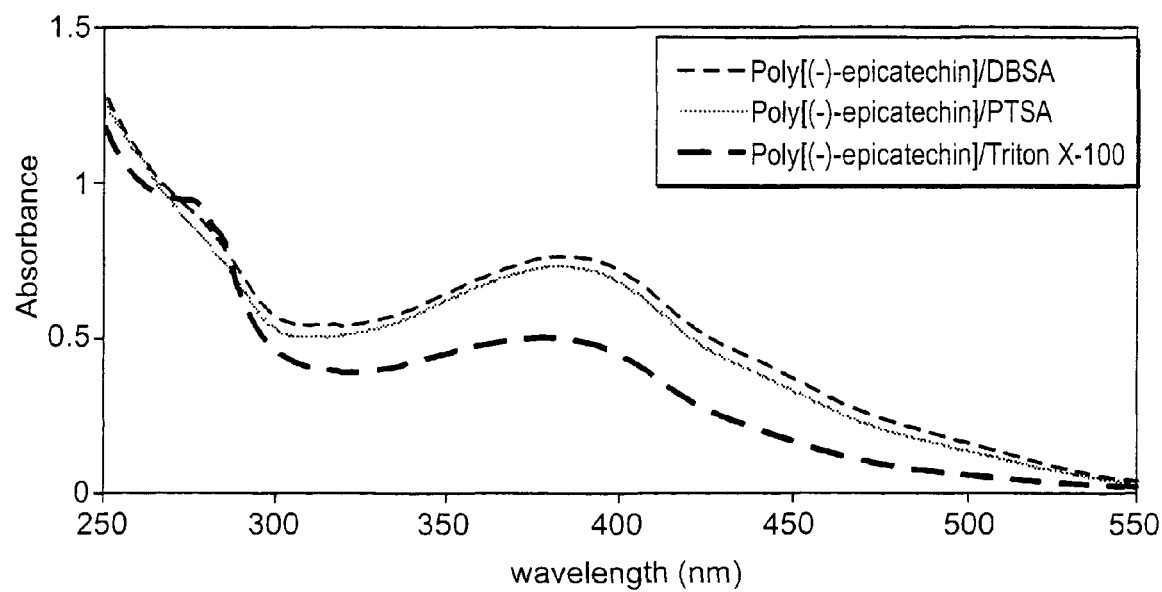
FIG. 6 is a UV-Vis absorption spectrum of oligo/poly(−)-epicatechin using different polymerization solubilizers (DBSA, Triton X-100 and PTSA).

FIG. 6 is a UV-Vis absorption spectrum of oligo/poly(−)-epicatechin using different polymerization solubilizers (DBSA, Triton X-100 and PTSA)

Example 5

Biocompatible, Water-Soluble Oligo/Poly(−)-Epicatechin Synthesized in Presence of Ethanol:Water Polymerization of (−)-epicatechin in the presence of water-ethanol mixtures catalyzed by HRP using hydrogen peroxide under ambient conditions. 500 µl of ethanol was dissolved in deionized water (10 mL) at pH 7.0 for the polymerization of (−)-epicatechin (3.44 mM). This was followed by the addition of 4 mg of HRP to this solution. The polymerization was initiated by the addition of 1021 µl of 0.3% hydrogen peroxide.

Example 6

Biocompatible, Water-Soluble Oligo/Poly(±)-Catechin Synthesized in Presence of PEO and SPS Polymerization of (±)-catechin in the presence of polyelectrolytic templates PEO and SPS catalyzed by HRP using hydrogen peroxide under ambient conditions. (±)-catechin (3.44 mM) and 13.41 µl of PEO was dissolved in deionized water (10 mL) at pH 7.0. This was followed by the addition of 4 mg of HRP to this solution. The polymerization was initiated by the addition of 1021 µl of 0.3% hydrogen peroxide.

Figure 7:
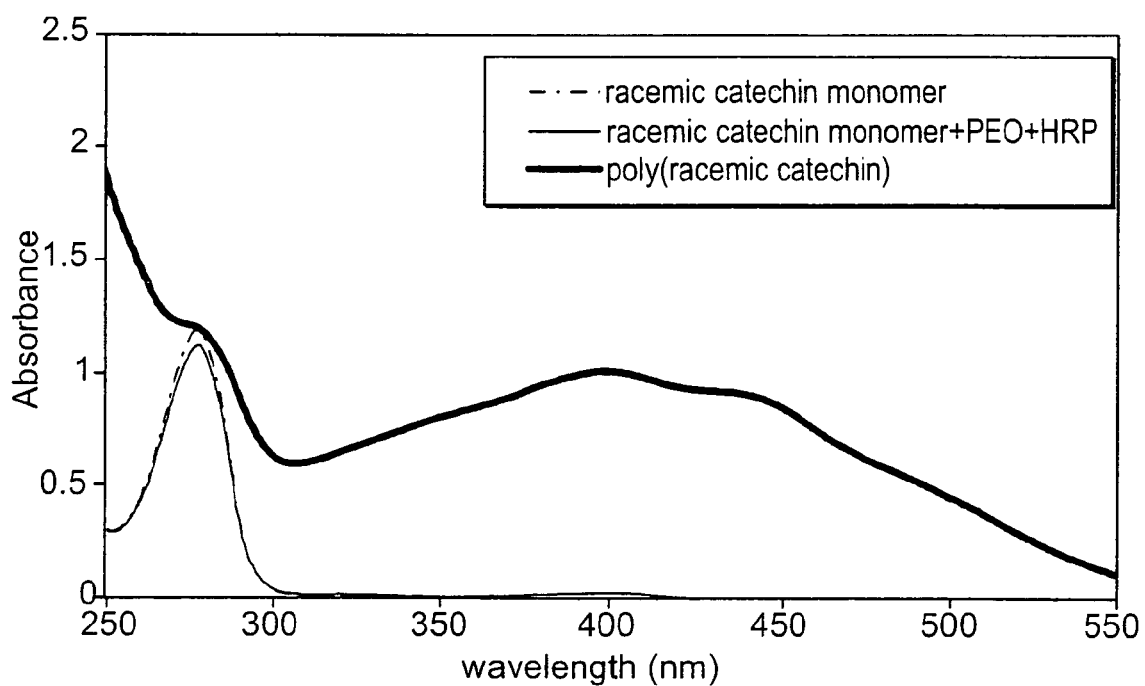
FIG. 7 is a UV-Vis absorption spectrum of mono- & oligo/poly racemic catechins synthesized using PEO.

FIG. 7 is a UV-Vis absorption spectrum of mono- & oligo/poly racemic catechins synthesized using PEO

Example 7

Biocompatible, Water-Soluble Oligo/Poly(±)-Catechin Synthesized in Presence of Non-Ionic Surfactants Polymerization of (±)-catechin in the presence of non-ionic surfactant Triton X-100 catalyzed by HRP using hydrogen peroxide under ambient conditions. (±)-catechin (3.44 mM) and Triton X-100 (0.3 mM) was dissolved in deionized water (10 mL) at pH 7.0. This was followed by the addition of 4 mg of HRP to this solution. The polymerization was initiated by the addition of 1021 µl of 0.3% hydrogen peroxide.

Examples 8-13

Biocompatible, Water-Soluble Oligo/Polyflavanoids Demonstrate Anticancer Activity The growth inhibitory effects and specificity of the oligo/polyflavanoids was evaluated for different types of human cancer cells and on normal cells. The oligo/polyflavanoids are found to have greater growth inhibitory effects & a higher specificity to cancer cells than monocatechins such as EGCG.

Four types of human cells, MCF-7 (HTB-22, low metastatic breast adenocarcinoma), MDA MB 231 (HTB-26, high metastatic breast adenocarcinoma), MCF12A (CRL#10782, normal mammary epithelial), and HT-29 (HTB-38, colon carcinoma) were obtained for use from the American Type Culture Collection (ATCC, Manassas, Va.). Stock cultures of MCF-7 cells were maintained in MEM with 10% Fetal Calf Serum, 1% fungizone, 1% GPS, NEAA, Sodium pyruvate and bovine insulin; MDA MB 231 in DMEM with 10% Calf Serum, 1% fungizone and 1% GPS; MCF12A cells in DMEM/F-12 with 10% Horse Serum, 20 ng/mL hEGF, 100 ng/mL cholera toxin, 500 ng/mL hydrocortisone and bovine insulin; HT-29 cells in McCoy's 5A with 10% Fetal Calf Serum 1% fungizone and 1% GPS. Cell cultures were incubated at 37° C., in a 5% $CO_2$ humidified atmosphere. This growth protocol for the various human cells followed the manufacturers recommendations.

Cells were plated in a multi-well assay plates (VWR, 29442-048). $T_0$ counts were taken after 24 hours, and cells were re-fed with or without treatments. Oligo/polyflavanoids and EGCG were solubilized immediately before use in ethanol, and then were added to the cell culture medium at indicated concentrations. Controls included treatment of cells in parallel triplicate wells with polyelectrolytes/solvents alone (PEO and/or ethanol). All treatments were performed in triplicates for each time point. Cells were harvested at each time point and washed with PBS (Gibco, 21600-069) and trypsinized (Gibco, 25300) for 15-20 minutes, and then were counted using a Beckman Coulter Z1 Series Particle Counter. Cell proliferation was expressed as percentage of control±SE. Cells not harvested were re-fed (with or without Tx) on days 6 and/or 9.

The cells were tested in proliferation assays using oligo/polycatechins at doses 0.1 to 5.0 µg/ml and monocatechin EGCG at doses of 0.1, 5.0, 9.2, and 40 µg/ml. Cell enumeration was conducted at $T_o$, and Days 3, 6, and 9, in triplicate per timepoint in replicate experiments. Statistical analysis was conducted using student T-test.

Example 8

Biocompatible, Water-Soluble Oligo/Polyflavanoids Demonstrate Anticancer Activity Against Colon Carcinoma Table 1 shows the effect on human HT-29 (HTB-38, colon carcinoma) cells treated with oligo/poly(−)-epicatechin (synthesized using water:ethanol as the biocompatible polymerization solubilizer). Data is expressed as percent growth inhibition of the cancer cells when compared to untreated cell growth in parallel. The colon cancer cells were inhibited from 32% at 0.1 micrograms/mL to 54% at 5 micrograms/mL. Therefore, oligo/poly(−)-epicatechin (water: ethanol) significantly inhibits the growth of colon cancer cells versus control.

TABLE 1

| oligo/poly(−)-epicatechi, micrograms/mL | Statistically significant growth inhibition |
|---|---|
| 0.1 | 32% |
| 0.5 | 32% |
| 1.0 | 57% |
| 5.0 | 54% |

Example 9

Figure 8:
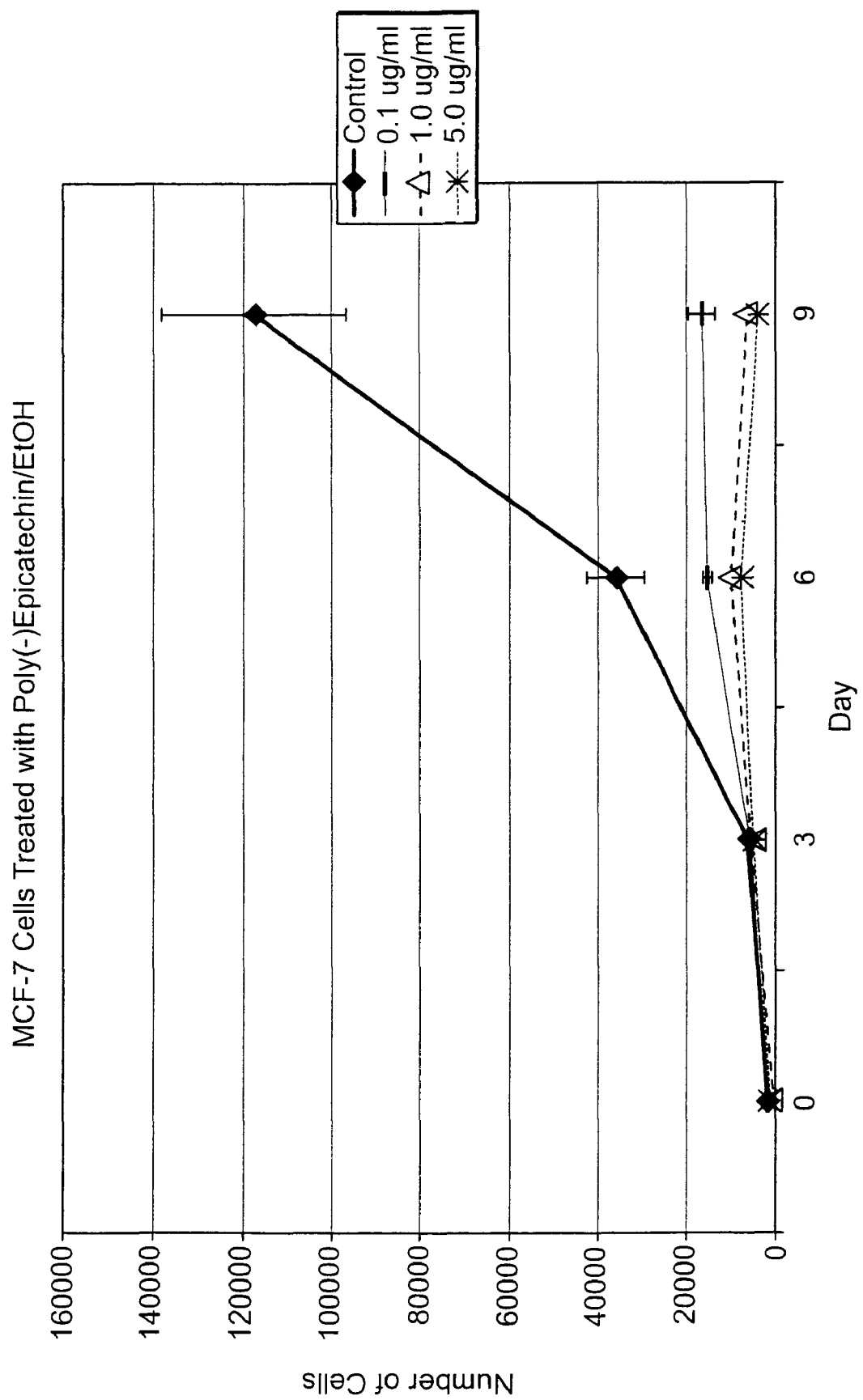
FIG. 8 is a graph of the significant treatment effect on human MCF-7 (HTB-22, low metastatic breast adenocarcinoma) cells treated with oligo/poly(−)-epicatechin (water: ethanol); oligo/poly(−)-epicatechin (water:ethanol) significantly inhibits the growth of low metastatic breast adenocarcinoma cells versus control.

Biocompatible, Water-Soluble Oligo/Polyflavanoids Demonstrate Anticancer Activity Against Low Metastatic Breast Adenocarcinoma FIG. 8 is a graph of the significant treatment effect on human (MCF-7 (HTB-22, low metastatic breast adenocarcinoma) cells treated with oligo/poly(−)-epicatechin (water: ethanol). Data is expressed as number of cells versus time in days. By Day 6, there was significant inhibition of the cancer cells at all dosage levels, compared to untreated cell growth in parallel. At Day 9, the 0.1 microgram/mL dose had only about 15% as many cells compare to control, while the 1.0 and 5.0 microgram/mL doses had only about 3% and about 6%, respectively, as many cells compare to control. Therefore, oligo/poly(−)-epicatechin (water:ethanol) significantly inhibits the growth of low metastatic breast adenocarcinoma cells versus control.

In another experiment under similar conditions, oligo(+) catechin/PEO also inhibited MCF-7 at 5.0 μg/ml. Only at high doses was EGCG effective (9.2 μg/ml).

Example 10

Figure 9:
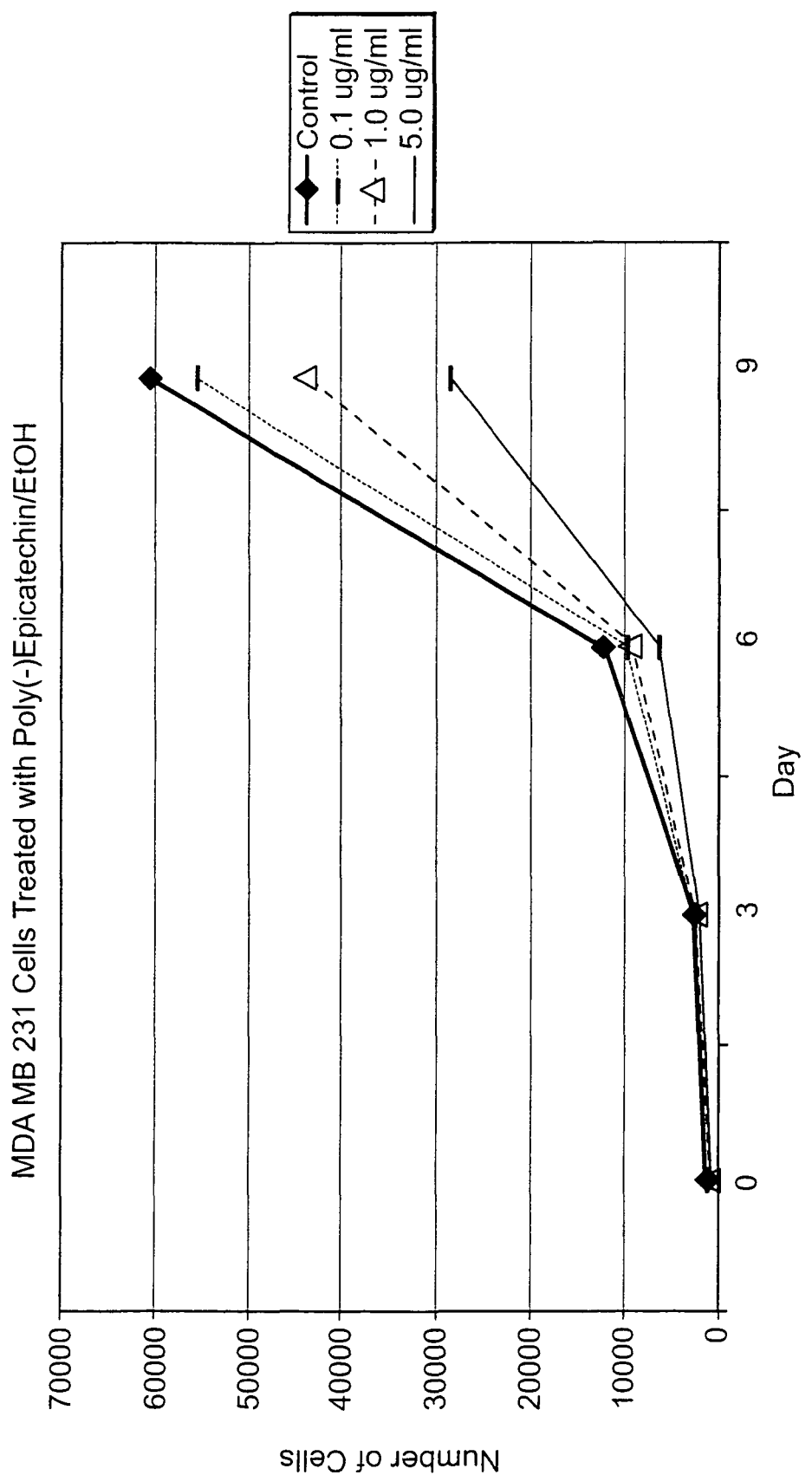
FIG. 9 is a graph of the significant treatment effect on human MDA MB 231 (HTB-26, high metastatic breast adenocarcinoma) cells treated with oligo/poly(−)-epicatechin (water: ethanol); oligo/poly(−)-epicatechin (water: ethanol) significantly inhibits the growth of high metastatic breast adenocarcinoma cells versus control.

Biocompatible, Water-Soluble Oligo/Polyflavanoids Demonstrate Anticancer Activity Against High Metastatic Breast Adenocarcinoma FIG. 9 is a graph of the significant treatment effect on human MDA MB 231 (HTB-26, high metastatic breast adenocarcinoma) cells treated with oligo/poly(−)-epicatechin (water:ethanol). Data is expressed as number of cells versus time in days. By Day 6, there was significant inhibition of the cancer cells at all dosage levels, compared to untreated cell growth in parallel. At Day 9, the 0.1 microgram/mL dose had only about 90% as many cells compare to control; the 1.0 microgram/mL dose had only about 70% as many cells compare to control; and the 5.0 microgram/mL dose had only about 45% as many cells compare to control. Therefore, oligo/poly(−)-epicatechin (water:ethanol) significantly inhibits the growth of high metastatic breast adenocarcinoma cells versus control.

Example 11

Figure 10:
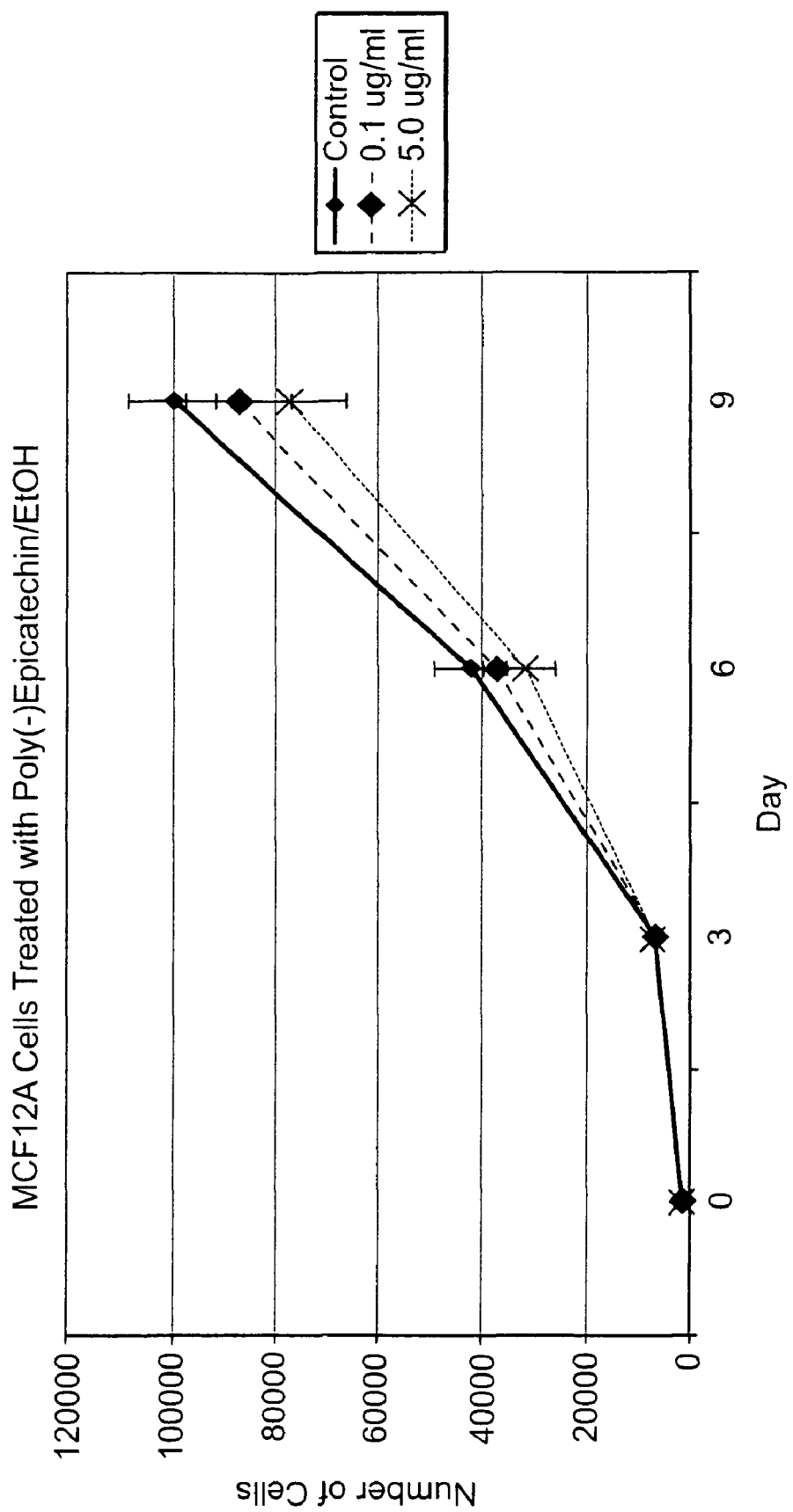
FIG. 10 is a graph of a control experiment showing that there was little or no significant inhibition of normal human MCF12A (CRL#10782, normal mammary epithelial) cells treated with oligo/poly(−)-epicatechin (water:ethanol); oligo/poly(−)-epicatechin (water:ethanol) was not observed to have a significant inhibitory effect on the growth of normal breast epithelial cells versus control.

Biocompatible, Water-Soluble Oligo/Polyflavanoids do not Inhibit Normal Cells FIG. 10 is a graph of a control experiment showing that there was little or no significant inhibition of normal human MCF12A (CRL#10782, normal mammary epithelial) cells treated with oligo/poly(−)-epicatechin (water:ethanol). Data is expressed as number of cells versus time in days. Through Day 9, there was no significant inhibition of the normal cells compared to untreated cell growth in parallel at the dosages tested. For example, at Day 9, the 0.1 microgram/mL dose had about 115% as many cells compare to control and the 5.0 microgram/mL dose had about 90% as many cells compare to control. Both values were within experimental error. Therefore, oligo/poly(−)-epicatechin (water:ethanol) was not observed to have a significant inhibitory effect on the growth of normal breast epithelial cells versus control.

In another experiment, under similar conditions, MCF-12A cells were inhibited by EGCG at 5.0 and 40 μg/ml doses. Of the oligo/polycatechins, only oligo/poly(+)catechin/PEO at 5.0 μg/ml was observed to inhibit the growth of normal cells.

Example 12

Figure 11:
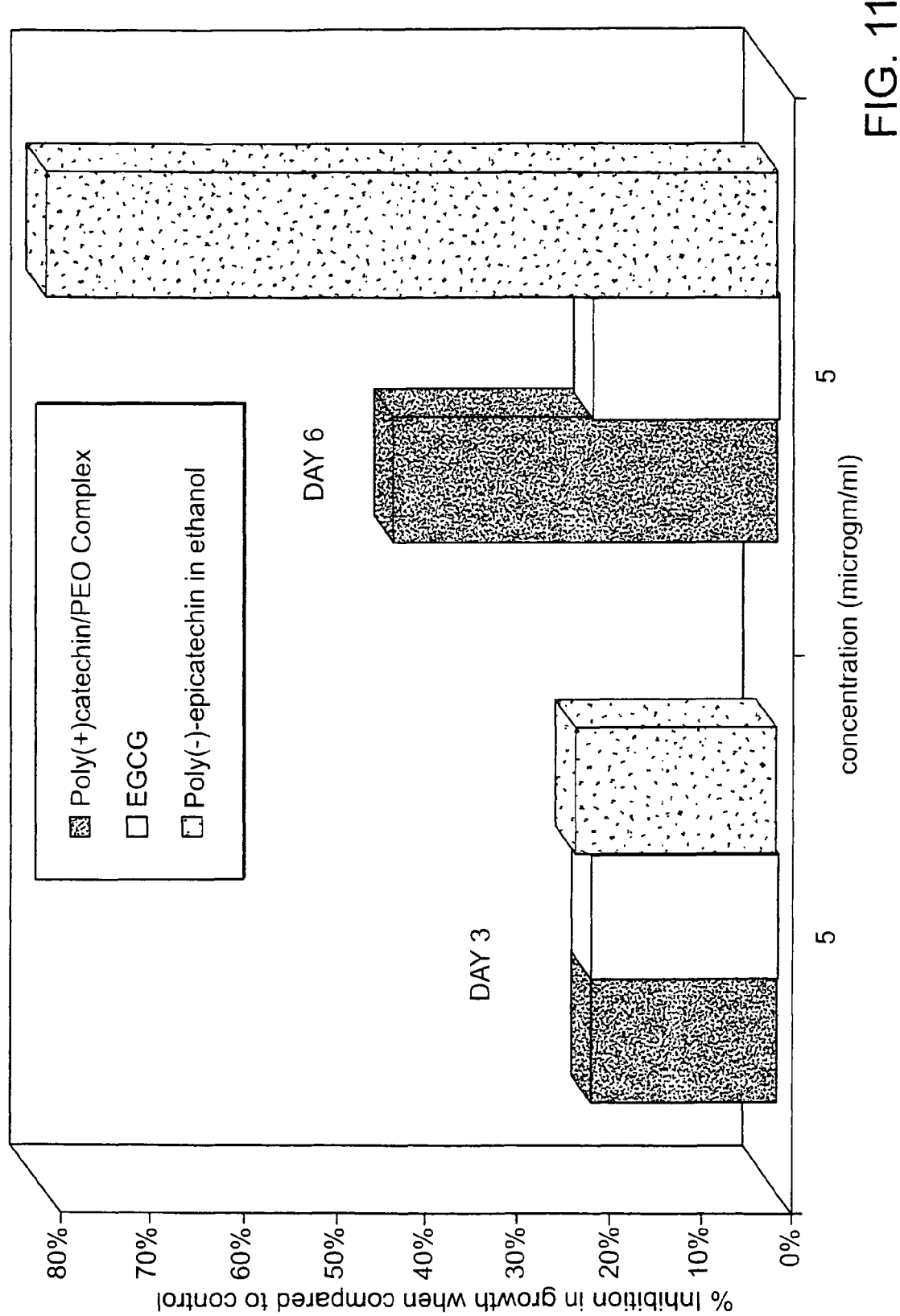
FIG. 11 is a bar graph of the treatment effect on human MDA MB 231 (HTB-26, high metastatic breast adenocarcinoma) cells treated with oligo/poly(+)-catechin (PEO) or oligo/poly(−)-epicatechin (water:ethanol) compared to monocatechin epigallocatechin gallate (EGCG); oligo/poly (+)-catechin (PEO) and oligo/poly(−)-epicatechin (water: ethanol) inhibit the growth of high metastatic breast adenocarcinoma cells to a greater extent than monocatechin EGCG.

Biocompatible, Water-Soluble Oligo/Polyflavanoids Exhibit Greater Anticancer Activity than Monocatechins FIG. 11 is a bar graph of the treatment effect on human MDA MB 231 (HTB-26, high metastatic breast adenocarcinoma) cells treated with oligo/poly(+)-catechin (PEO) or oligo/poly(−)-epicatechin (water: ethanol) compared to monocatechin epigallocatechin gallate (EGCG). All compounds were administered at a concentration of 5.0 micrograms/mL. Data is expressed as % inhibition of growth of cells at 3 and 6 days. At day 3, the oligo/poly(+)-catechin (PEO) inhibited cell growth about 2% more than oligo/poly (−)-epicatechin (water:ethanol) or EGCG. By Day 6, the oligo/poly(+)-catechin (PEO) inhibited cell growth about 60% more than EGCG, or was about 4 times more effective, while the oligo/poly(−)-epicatechin (water:ethanol) inhibited cell growth about 25% more than EGCG, or was over 2 times more effective. Therefore, oligo/poly(+)-catechin (PEO) and oligo/poly(−)-epicatechin (water: ethanol) inhibit the growth of high metastatic breast adenocarcinoma cells to a greater extent than monocatechin EGCG.

Example 13

Figure 12:
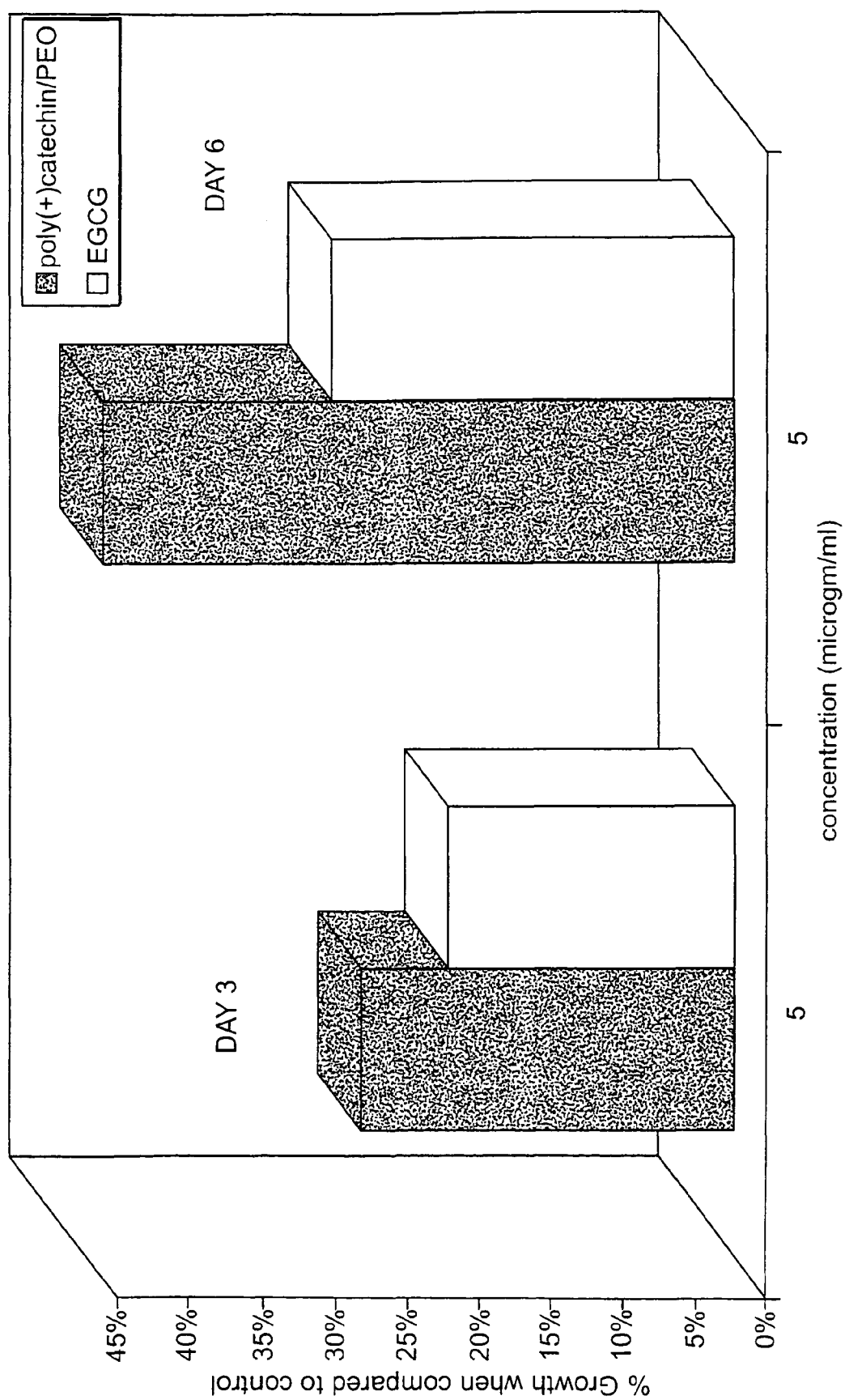
FIG. 12 is a bar graph of the treatment effect on human MDA MB 231 (HTB-26, high metastatic breast adenocarcinoma) cells treated with oligo/poly(+)-catechin (synthesized using polyethylene oxide, PEO, as the biocompatible polymerization solubilizer) compared to monocatechin epigallocatechin gallate (EGCG); oligo/poly(+)-catechin (PEO) inhibits the growth of high metastatic breast adenocarcinoma cells to a greater extent than monocatechin EGCG.

Biocompatible, Water-Soluble Oligo/Polyflavanoids Exhibit Greater Anticancer Activity than Monocatechins FIG. 12 is a bar graph of the treatment effect on human MDA MB 231 (HTB-26, high metastatic breast adenocarcinoma) cells treated with oligo/poly(+)-catechin (synthesized using polyethylene oxide, PEO, as the biocompatible polymerization solubilizer) compared to monocatechin epigallocatechin gallate (EGCG). Both compounds were administered at a concentration of 5.0 micrograms/mL. Data is expressed as % inhibition of growth of cells at 3 and 6 days. At day 3, the oligo/poly(+-catechin (PEO) inhibited cell growth about 5% more than EGCG. By Day 6, the oligo/poly (+)-catechin (PEO) inhibited cell growth about 15% more than EGCG. Therefore, oligo/poly(+)-catechin (PEO) inhibits the growth of high metastatic breast adenocarcinoma cells to a greater extent than monocatechin EGCG.

In another experiment under similar conditions, a 5.0 μg/ml dose of oligo(−) catechin/PEO, inhibited MDA-MB-231 cell more effectively than EGCG at the same dose.

Example 14

Biocompatible, Water-Soluble Oligo/Poly(+)-Catechin Synthesized in Presence of Hematin Polymerization of catechins in the presence of hematin was performed in ambient conditions. The monomer was dissolved in pH 7 buffer containing 5% ethanol. 2 mg of hematin was dissolved in high pH water and the pH brought down by the addition of hydrochloric acid. Hematin solution was added to the buffer solution containing the monomer and the polymerization was initiated by the addition of 1100 μl of 0.3% hydrogen peroxide. These polymers can also be synthesized using amphiphiles such as SPS and PEO.

Figure 13:
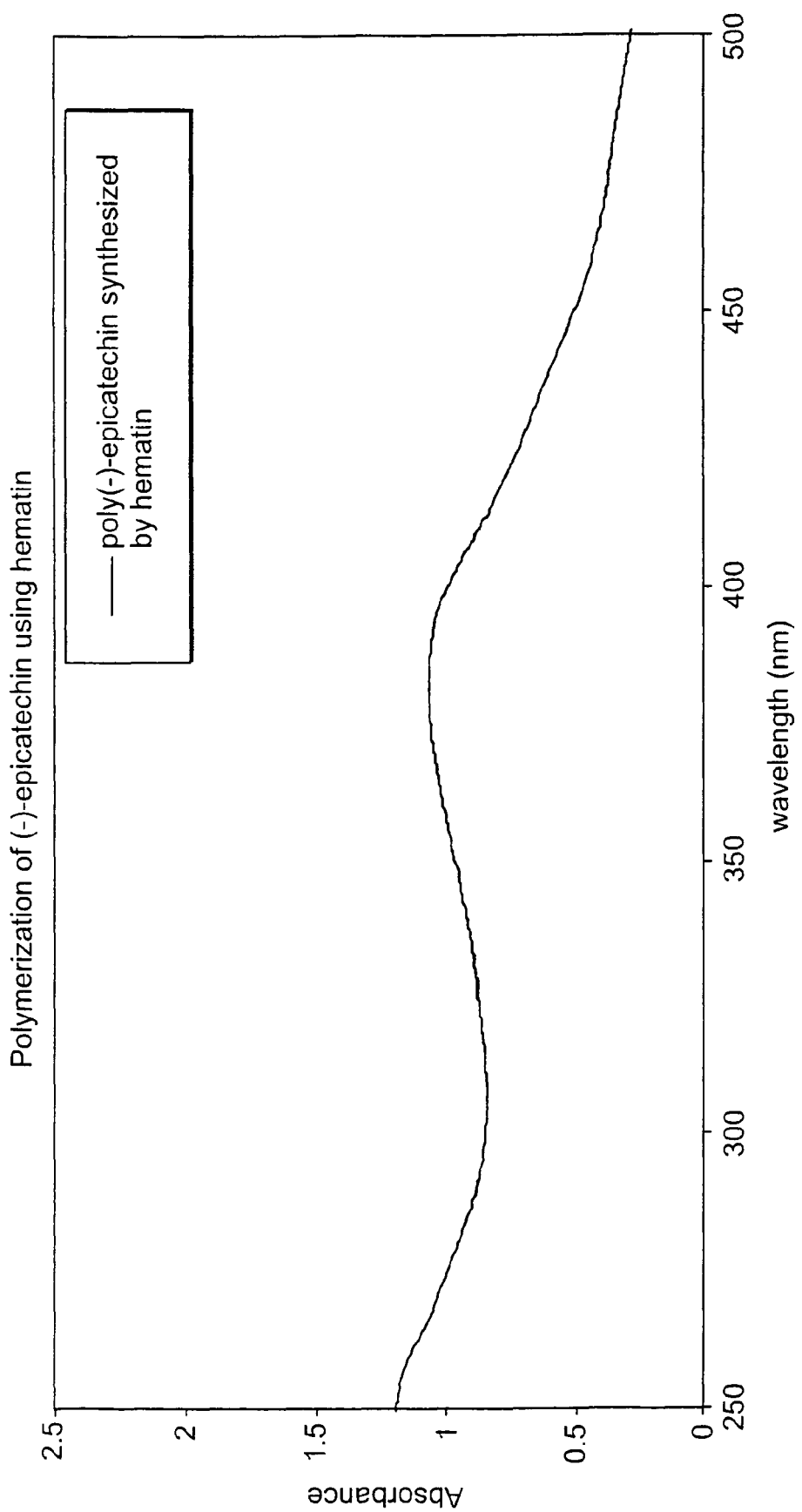
FIG. 13 is a UV-Visible spectra of poly(−)-epicatechin synthesized using hematin as a catalyst.
Figure 14:
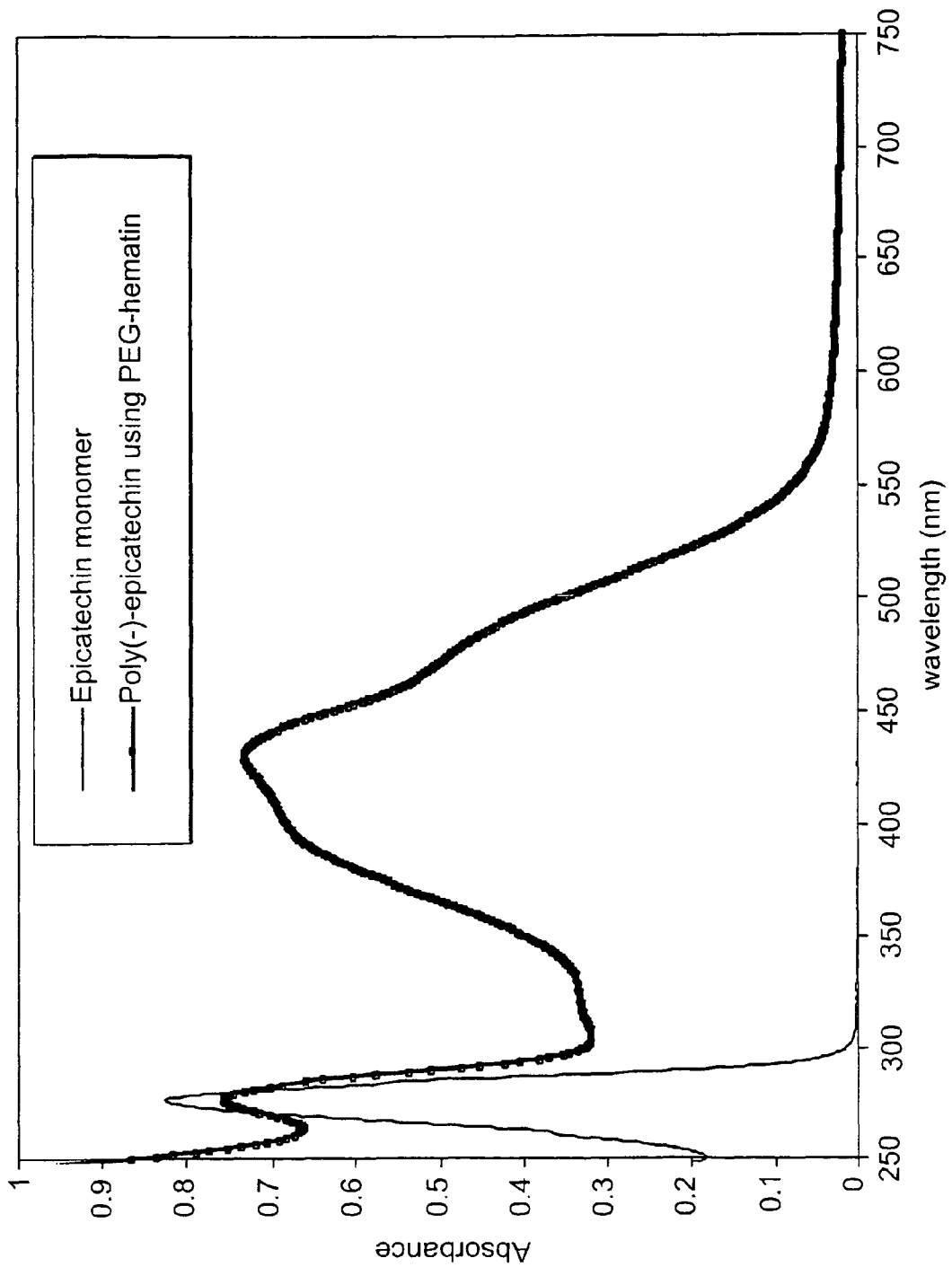
FIG. 14 is a UV-Visible spectra of poly(−)-epicatechin synthesized using pegylated hematin as a catalyst.

FIG. 13 is a UV-Vis absorption spectrum of poly-(-)epicatechin synthesized using hematin FIG. 14 is a UV-Vis absorption spectrum of poly-(-)epicatechin synthesized using pegylated hematin.

While this invention has been particularly shown and described with references to preferred embodiments thereof, it will be understood by those skilled in the art that various changes in form and details may be made therein without departing from the scope of the invention encompassed by the appended claims.

The entire teachings of each reference cited herein are incorporated by reference in their entirety.

What is claimed is:

1. A polymer comprising at least two repeat units independently selected from the group consisting of:

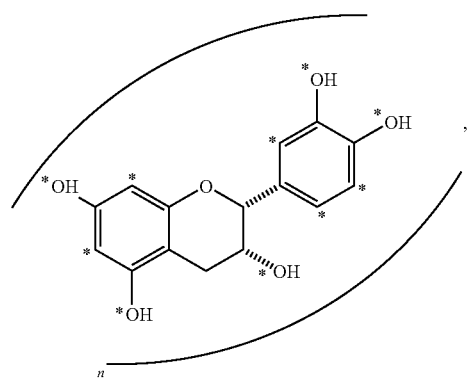

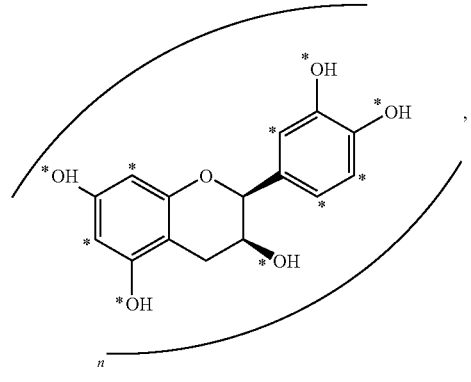

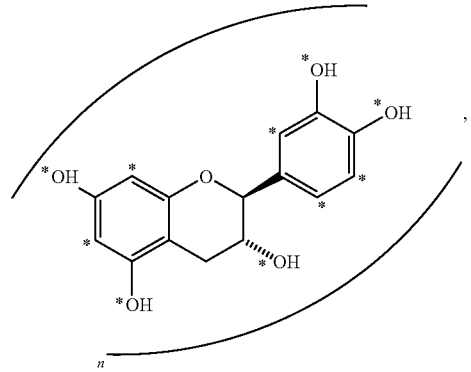

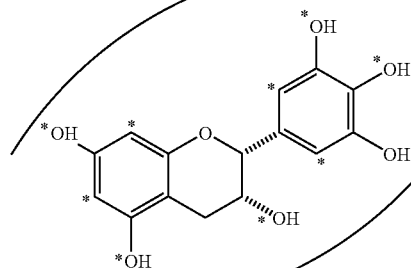

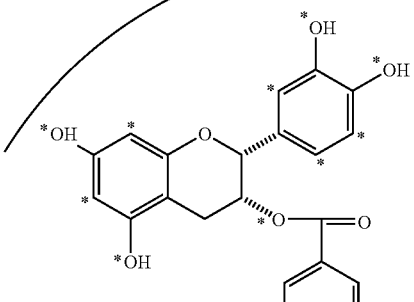

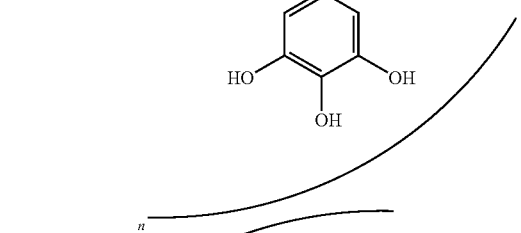

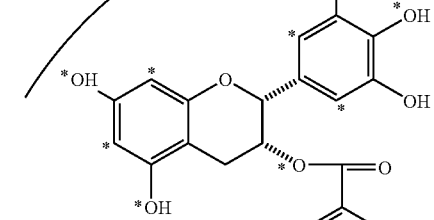

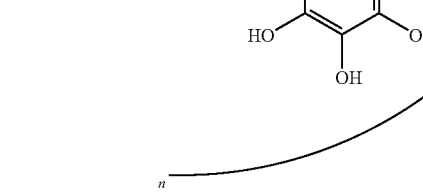

or a pharmaceutically acceptable salt thereof;
wherein:
each repeat unit is independently optionally substituted with one or more substituents;
between one and four —H atoms in each repeat unit attached to the oxygen or carbon at each * are independently replaced by a polymer link; and
each n is independently an integer from 0 to 170 inclusive, wherein the sum of all ns is an integer from 2 to 170 inclusive, and wherein the polymer is formed by polymerizing the repeat unit in the presence of an oxido-reductase, hydrogen peroxide, and a polymerization solubilizer that includes ethanol and water.

2. The polymer of claim 1, wherein the sum of all ns is an integer from 10 to 170 inclusive.

3. The polymer of claim 2, wherein the polymer is a copolymer.

4. The polymer of claim 3, wherein the repeat units are:

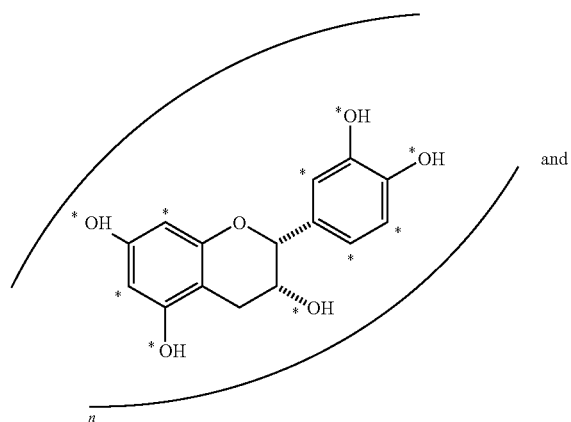

and

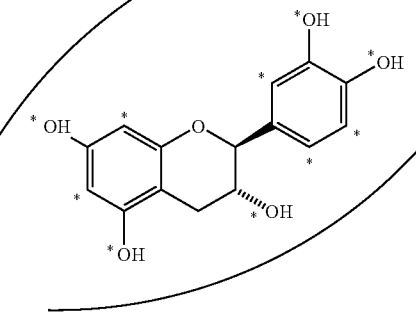

or a pharmaceutically acceptable salt thereof;
wherein:
each repeat unit is independently optionally substituted with one or more substituents.

5. The polymer of claim 3, wherein the repeat units are:

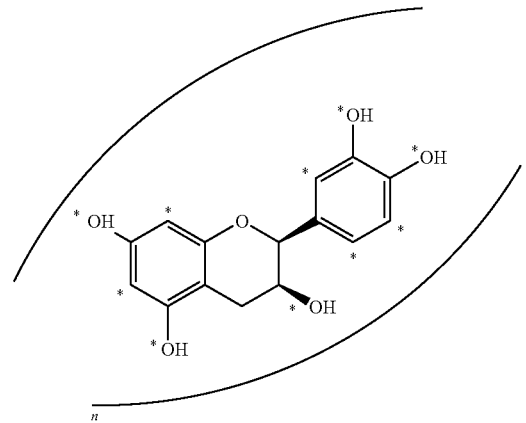

and

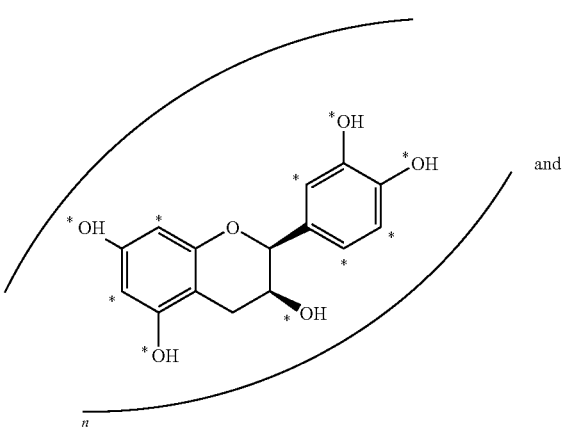

or a pharmaceutically acceptable salt thereof;
wherein:
each repeat unit is independently optionally substituted with one or more substituents.

6. The polymer of claim 3, wherein the repeat units are:

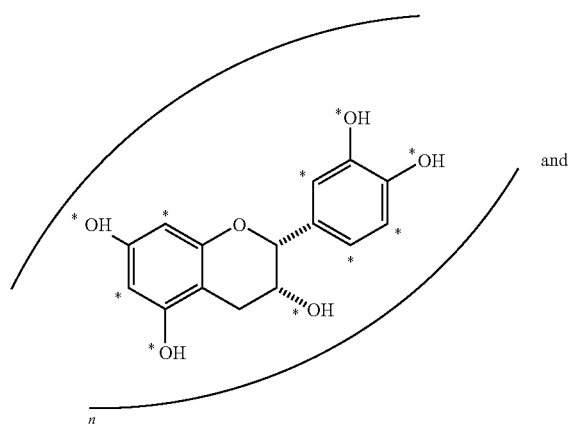

and

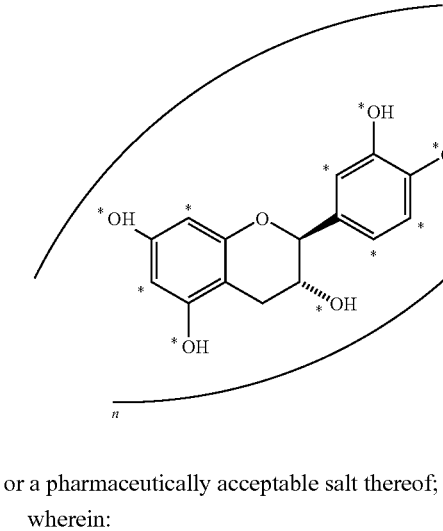

or a pharmaceutically acceptable salt thereof;
wherein:
each repeat unit is independently optionally substituted with one or more substituents.

7. The polymer of claim 3, wherein the copolymer further comprises the repeat unit:

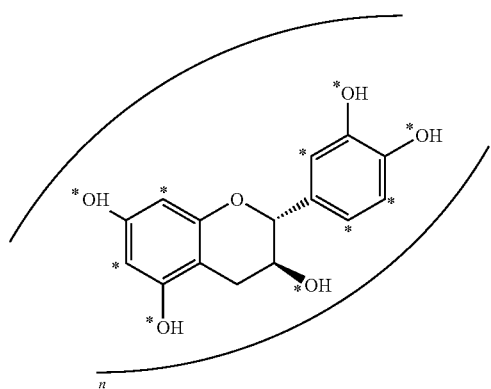

or a pharmaceutically acceptable salt thereof;
wherein:
each repeat unit is independently optionally substituted with one or more substituents.

8. The polymer of claim 7, wherein the repeat units are:

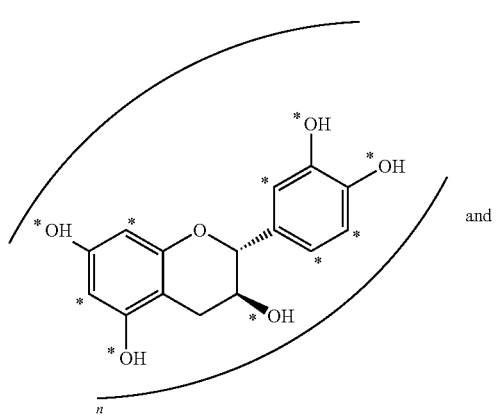

or a pharmaceutically acceptable salt thereof;
wherein:
each repeat unit is independently optionally substituted with one or more substituents.

9. The polymer of claim 7, wherein the repeat units are:

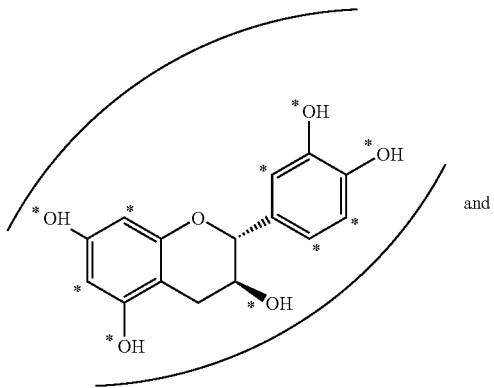

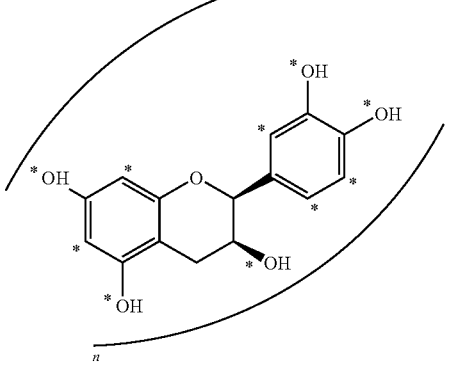

or a pharmaceutically acceptable salt thereof;
wherein:
each repeat unit is independently optionally substituted with one or more substituents.

10. The polymer of claim 2, wherein each repeat unit is represented by the following structural formula:

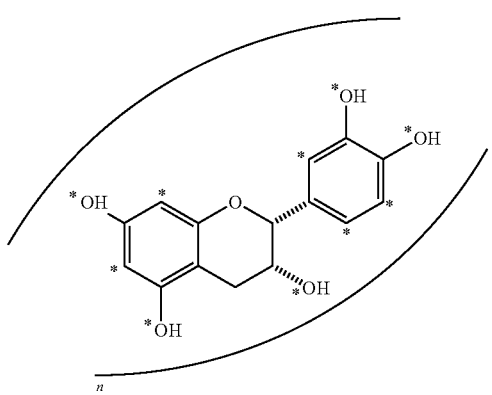

or a pharmaceutically acceptable salt thereof, wherein each repeat unit is independently optionally substituted with one or more substituents.

11. The polymer of claim 10, wherein each repeat unit is independently selected from the group consisting of:

53
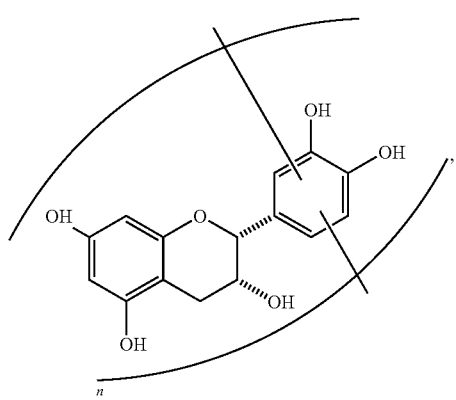
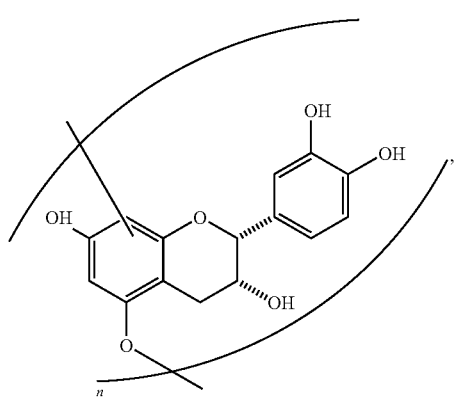
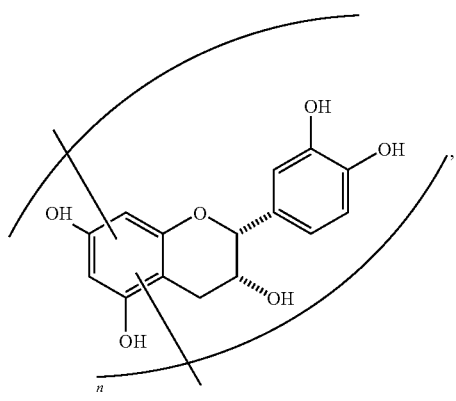
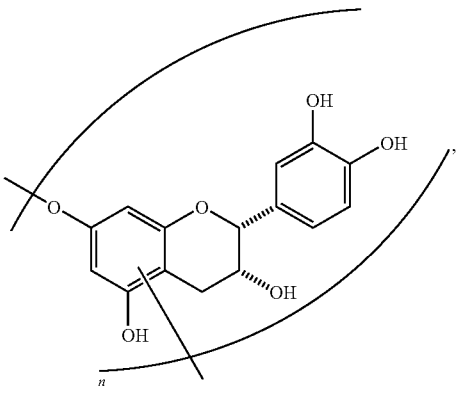
54
-continued
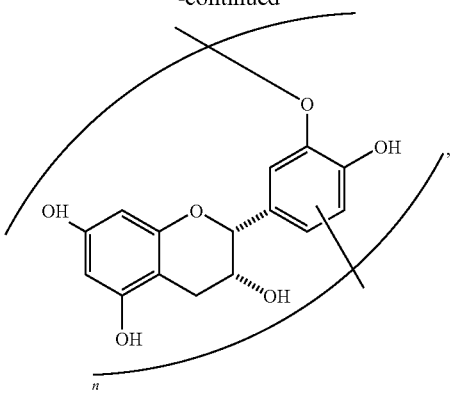
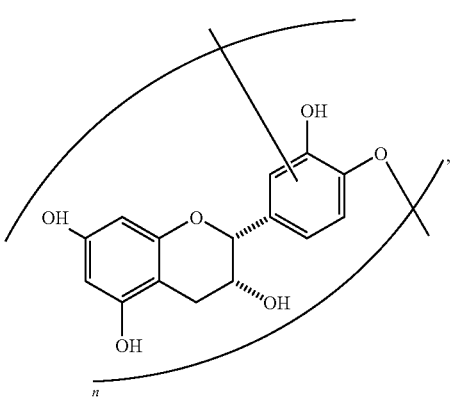
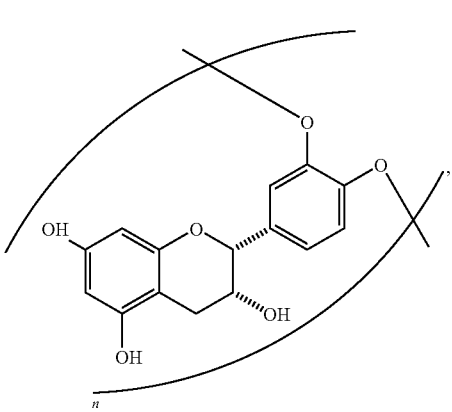
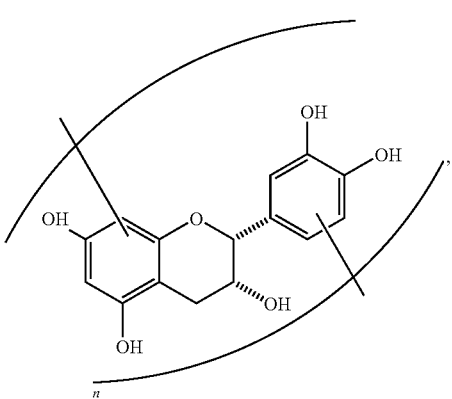

55
-continued
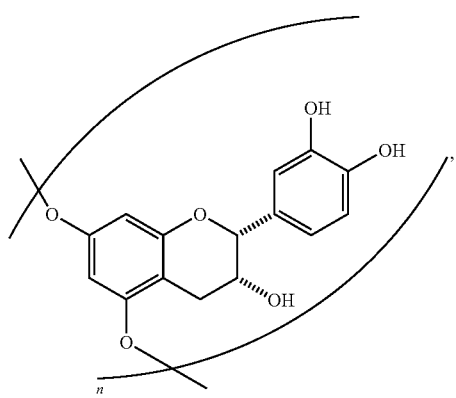
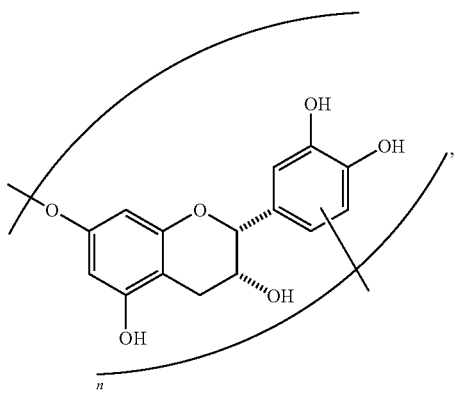
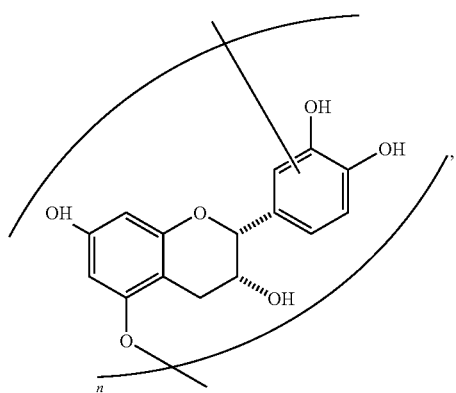
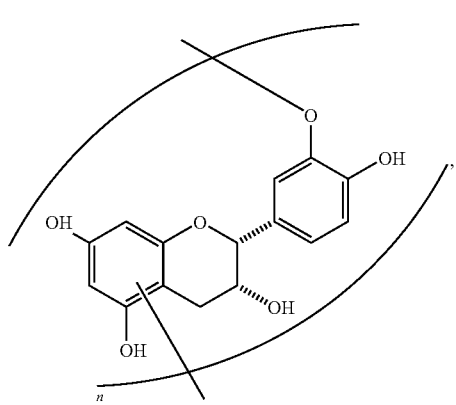
56
-continued
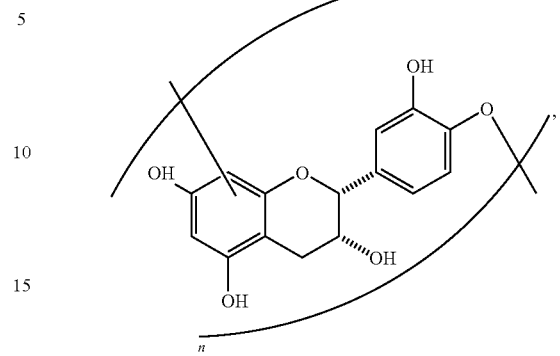
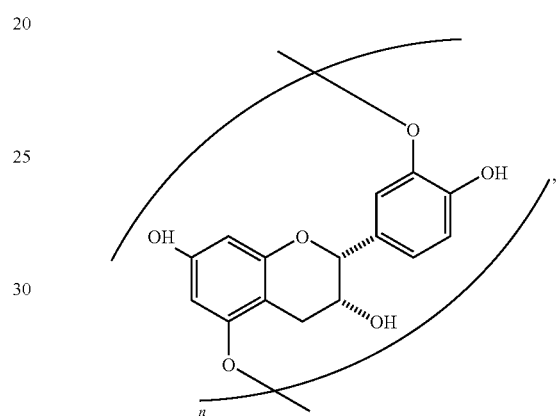
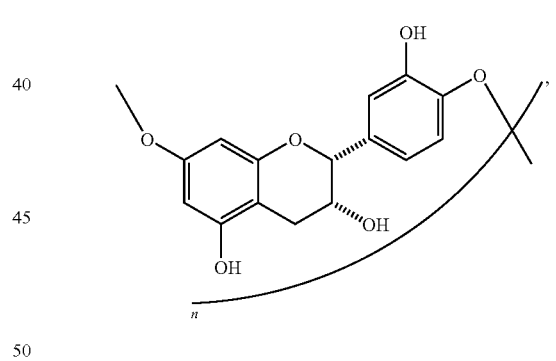
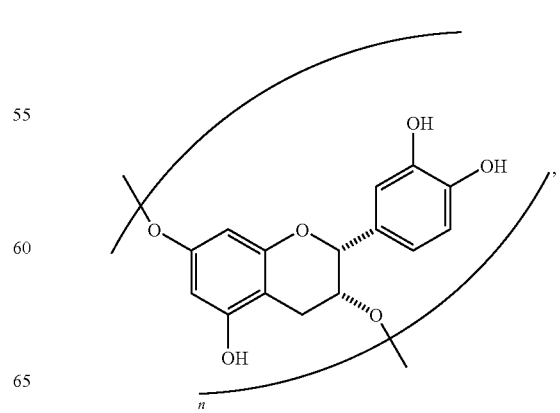

57
-continued
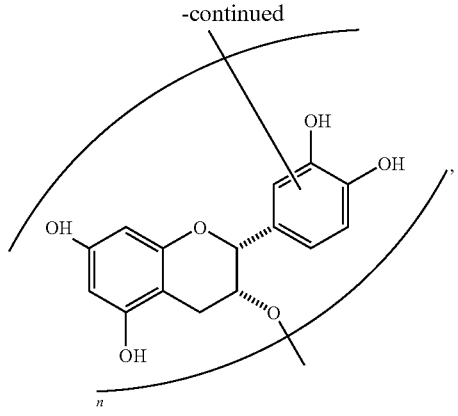
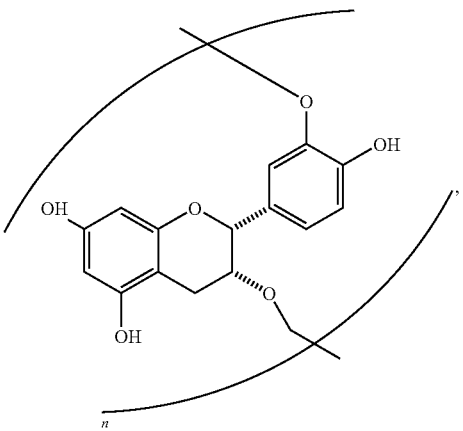
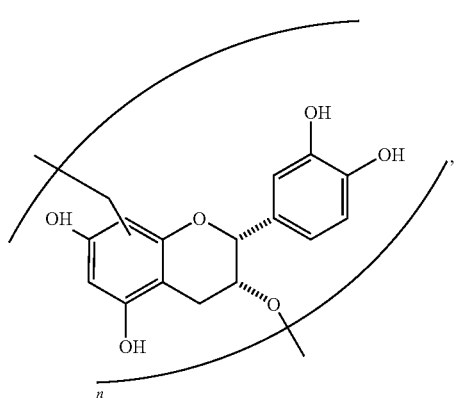
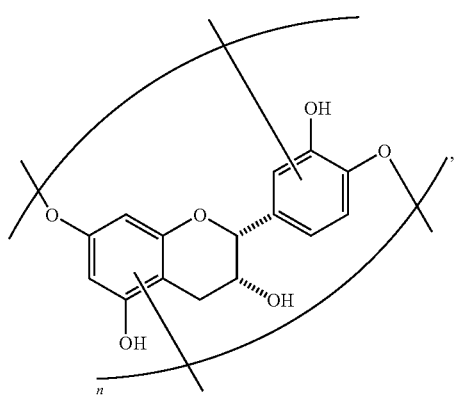
58
-continued
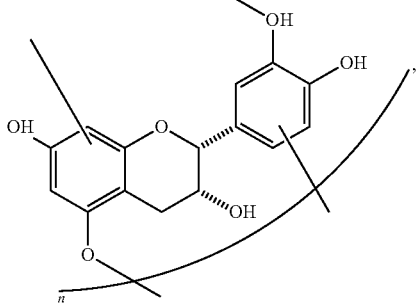
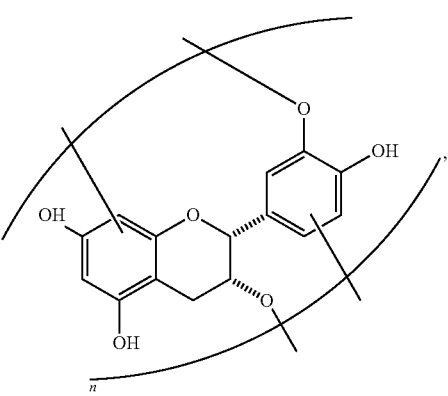
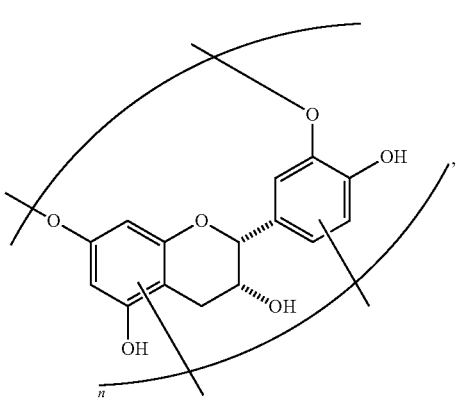
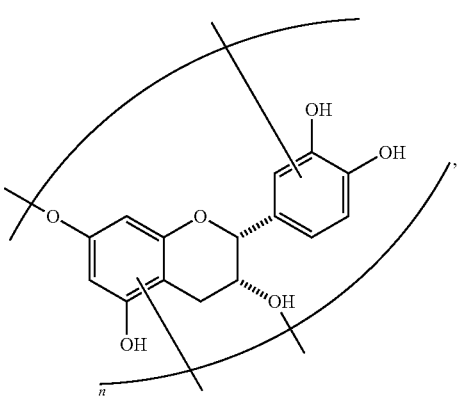

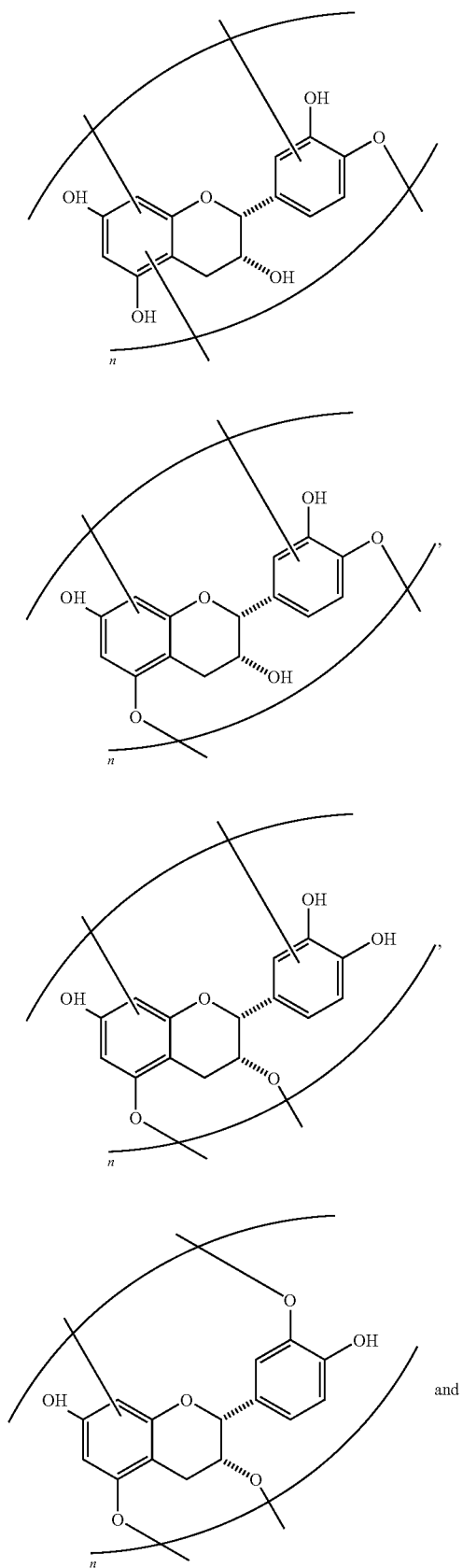

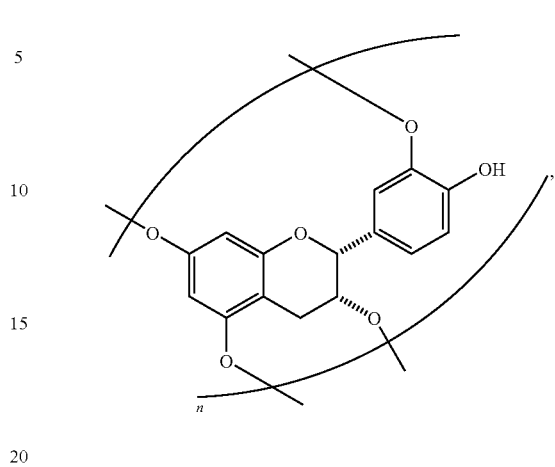

or a pharmaceutically acceptable salt thereof, wherein each repeat unit is independently optionally substituted with one or more substituents.

12. The polymer of claim 2, having a UV-visible spectrum including a peak between 350 and 450 nm.

13. The polymer of claim 2, wherein the polymer has a solubility in 1 mL of water of between 0.5 and 5 mg at room temperature.

14. The polymer of claim 13, wherein the polymer has a solubility in 1 mL of water of between 1 and 3 mg at room temperature.

15. The polymer of claim 2, wherein the polymer has an average molecular weight of between 3,000 and 50,000 Daltons.

16. The polymer of claim 15, wherein the polymer has an average molecular weight of between 10,000 and 50,000 Daltons.

17. The polymer of claim 2, wherein a majority of the repeat units are the same enantiomer, whereby the polymer is chiral.

18. The polymer of claim 17, wherein substantially all the repeat units of the polymer are the same enantiomer, whereby the oligo/polyflavanoid is chiral.

19. The polymer of claim 18, wherein all the repeat units of the polymer are the same enantiomer, whereby the oligo/polyflavanoid is chiral.

20. The polymer of claim 2, wherein one or more repeat units are substituted with one or more substituents independently selected from —F, —Cl, —Br, —I, —CN, —NO$_2$, —OR$^a$, —C(O)R$^a$, —OC(O)R$^a$, —C(O)OR$^a$, —SR$^a$, —C(S)R$^a$, —OC(S)R$^a$, —C(S)OR$^a$, —C(O)SR$^a$, —C(S) SR$^a$, —S(O)R$^a$, —SO$_2$R$^a$, —SO$_3$R$^a$, —PO$_2$R$^a$R$^b$, —PO$_3$R$^a$R$^b$, —N(R$^a$R$^b$), —C(O)N(R$^a$R$^b$), —C(O) NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), —C(NR$^c$)—N(R$^a$R$^b$), —NR$^d$—C(NR$^c$)—N(R$^a$R$^b$), —NR$^a$N(R$^a$R$^b$), —CR$^c$=CR$^a$R$^b$, —C≡CR$^a$, =O, =S, =CR$^a$R$^b$, =NR$^a$, =NOR$^a$, =NNR$^a$, optionally substituted alkyl, optionally substituted cycloalkyl, optionally substituted aliphatic, optionally substituted cycloaliphatic, optionally substituted heterocyclic, optionally substituted benzyl, optionally substituted aryl, and optionally substituted heteroaryl; wherein $R^a$-$R^d$ are each independently —H or an optionally substituted aliphatic, optionally substituted cycloaliphatic, optionally substituted heterocyclic, optionally substituted benzyl, optionally substituted aryl, or optionally substituted heteroaryl, or, —N($R^a R^b$), taken together, is an optionally substituted heterocyclic group.

21. The polymer of claim 2, wherein one or more repeat units are unsubstituted.

22. The polymer of claim 21, wherein all repeat units are unsubstituted.

23. A biocompatible composition comprising a biocompatible solvent and an oligo/polyflavanoid or a pharmaceutically acceptable salt, solvate, or complex thereof wherein the oligo/polyflavanoid is formed by polymerizing a repeat unit in the presence of an oxido-reductase, hydrogen peroxide, and a polymerization solubilizer that includes ethanol and water.

24. The biocompatible composition of claim 23, wherein the oligo/polyflavanoid comprises repeat units selected from the group consisting of optionally substituted catechin, quercitin, flavonone, isoflavone, chalcone, anthocyanidin, chrysin, primuletin, fisetin, naringin, hesperidin, prunin, daidzein, genistein, pelargonidin, cyanidin and delphinidin.

25. The biocompatible composition of claim 24, wherein the oligo/polyflavanoid is selected from oligo/poly(−)-catechin, oligo/poly(−)-epicatechin, oligo/poly(−)-gallocatechin, oligo/poly(−)-catechin gallate, oligo/poly(−)-epigallocatechin, oligo/poly(−)-gallocatechin gallate, oligo/poly(−)-epicatechin gallate, oligo/poly(−)-epigallocatechin gallate, oligo/poly(+)-catechin, oligo/poly(+)-epicatechin, oligo/poly(+)-gallocatechin, oligo/poly(+)-catechin gallate, oligo/poly(+)-epigallocatechin, oligo/poly(+)-gallocatechin gallate, oligo/poly(+)-epicatechin gallate, and oligo/poly(+)-epigallocatechin gallate.

26. The biocompatible composition of claim 25, wherein the oligo/polyflavanoid is oligo/poly(−)-catechin or oligo/poly(+)-catechin.

27. The biocompatible composition of claim 25, wherein the oligo/polyflavanoid is oligo/poly(−)-epicatechin or oligo/poly(+)-epicatechin.

28. The biocompatible composition of claim 25, wherein the oligo/polyflavanoid is oligo/poly(−)-epicatechin.

29. The biocompatible composition of claim 25, wherein the oligo/polyflavanoid is complexed with an amphiphile.

30. The biocompatible composition of claim 29, wherein the amphiphile is selected from the group consisting of polyethylene oxide, sulfonated polystyrene, poly (vinyl phosphonic acid) sodium dodecyl benzenesulfonate, polyoxyethylene (10), isooctylphenyl ether (Triton X-100), p-toluenesulphonic acid monohydrate, deoxyribonucleic acid, ribonucleic acid, 1-palmitoly-2-oleoyl-sn-glycerol-3-phosphate, sodium octylsulfonate, 1-palmitoly-2-oleoyl-sn-glycero-3-phosphocholine, and benzoyl-L-tyrosine-p-nitroanilde.

31. The biocompatible composition of claim 29, wherein the amphiphile is biocompatible.

32. The biocompatible composition of claim 31, wherein the amphiphile is selected from the group consisting of polyethylene oxide, sulfonated polystyrene, poly (vinyl phosphonic acid), polyoxyethylene(10), deoxyribonucleic acid and ribonucleic acid.

33. The biocompatible composition of claim 32, wherein the amphiphile is polyethylene oxide.

34. A method of synthesizing a polymer comprising at least two repeat units independently selected from the group consisting of:

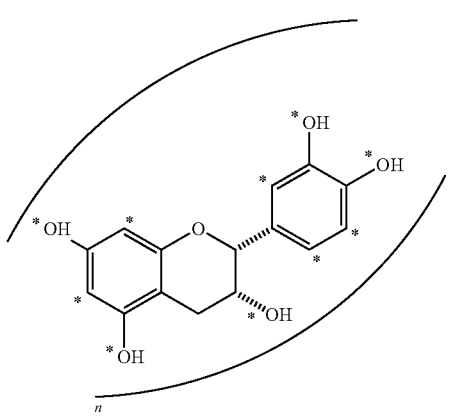

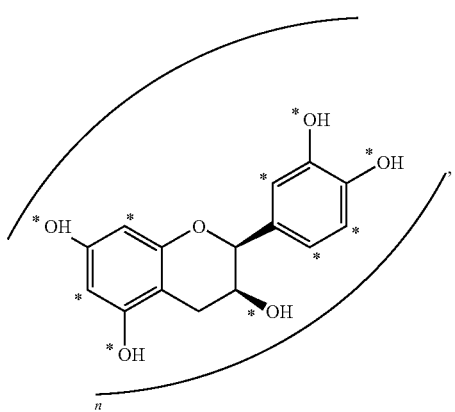

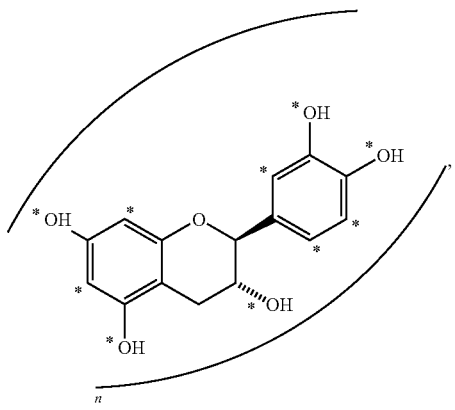

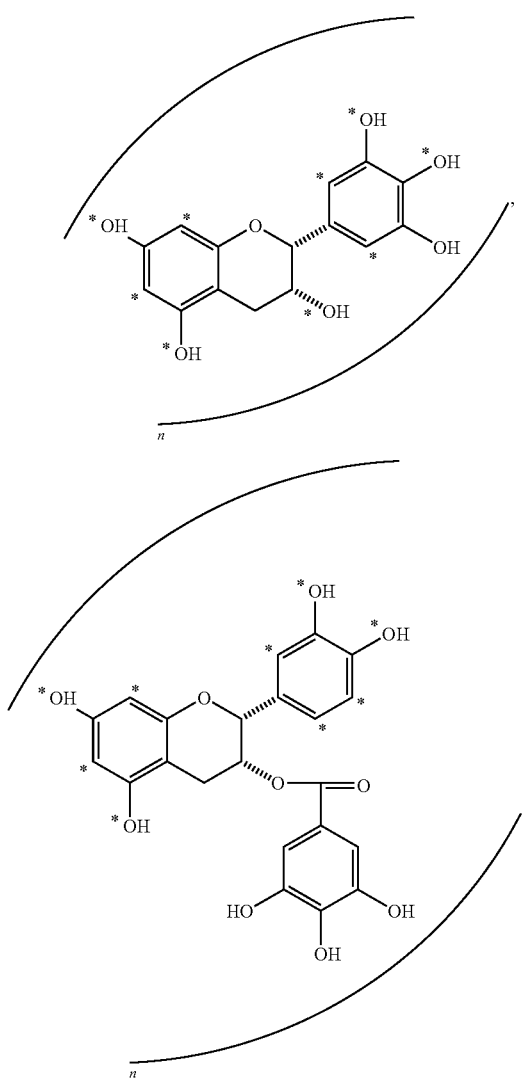

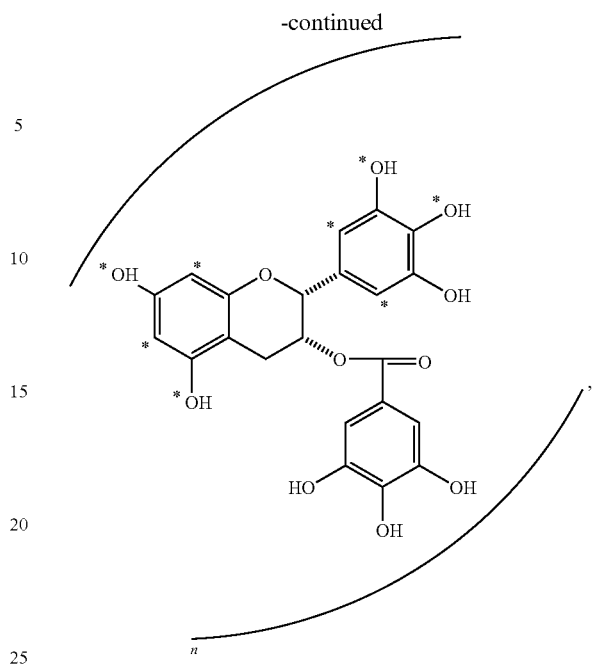

or a pharmaceutically acceptable salt thereof;
wherein:
each repeat unit is independently optionally substituted with one or more substituents;
between one and four —H atoms in each repeat unit attached to the oxygen or carbon at each * are independently replaced by a polymer link; and
each n is independently an integer from 0 to 170 inclusive, wherein the sum of all ns is an integer from 2 to 170 inclusive;
comprising polymerizing the repeat unit in the presence of an oxido-reductase, hydrogen peroxide, and a polymerization solubilizer that includes ethanol and water.

35. A method of treating breast cancer in a subject in need thereof comprising administering to the subject a therapeutically effective amount of a polymer of claim 1.

36. A method of or treating colon cancer in a subject in need thereof comprising administering to the subject a therapeutically effective amount of a polymer of claim 1.

* * * * *